(12) United States Patent
Schobel et al.

(10) Patent No.: US 8,974,826 B2
(45) Date of Patent: *Mar. 10, 2015

(54) NANOPARTICLE FILM DELIVERY SYSTEMS

(75) Inventors: Alexander M. Schobel, Whitehouse Station, NJ (US); Garry L. Myers, Kingsport, TN (US); Keith Joseph Kendall, Bridgewater, NJ (US); Thomas Rademacher, Boars Hill (GB); Jan Mous, Giebenach (CH); Justin N. W. Barry, Pontevedra (ES); Phillip Williams, Botley (GB); Africa Garcia Barrientos, Vizcaya (ES)

(73) Assignees: Monosol RX, LLC, Warren, NJ (US); Midatech Limited, Oxfordshire (GB)

( * ) Notice: Subject to any disclaimer, the term of this patent is extended or adjusted under 35 U.S.C. 154(b) by 26 days.

This patent is subject to a terminal disclaimer.

(21) Appl. No.: 13/157,836

(22) Filed: Jun. 10, 2011

(65) Prior Publication Data
US 2012/0009260 A1 Jan. 12, 2012

Related U.S. Application Data

(60) Provisional application No. 61/353,366, filed on Jun. 10, 2010.

(51) Int. Cl.
*A61K 9/14* (2006.01)
*A61K 38/00* (2006.01)
(Continued)

(52) U.S. Cl.
CPC ............... *A61K 9/0056* (2013.01); *A61K 9/006* (2013.01); *A61K 9/2031* (2013.01);
(Continued)

(58) Field of Classification Search
CPC ................ A61K 9/006; A61K 9/2031; A61K 47/48861; A61K 47/4893; A61K 9/7007; A61K 38/00; A61K 9/0056; B82Y 5/00
USPC .......... 424/484; 264/255; 514/1.1, 10.2, 10.9, 514/11.1, 11.5, 11.6, 11.7, 11.8, 11.9, 12.3, 514/12.7, 12.9, 5.9, 8.5, 8.6, 9.7, 9.9; 977/773, 906

See application file for complete search history.

(56) References Cited

U.S. PATENT DOCUMENTS 307,537 A 11/1884 Foulks
688,446 A 12/1901 Stempel
(Continued)

FOREIGN PATENT DOCUMENTS

DE 2432925 B2 1/1976
DE 2449865 A1 4/1976
(Continued)

OTHER PUBLICATIONS

Bhumkar et al. ("Chitosan Reduced Gold Nanoparticles as Novel Carriers for Transmucosal Delivery of Insulin" in Pharamaceutical Research, vol. 24, No. 8, Aug. 2007).*
(Continued)

*Primary Examiner* — Blessing M Fubara
(74) *Attorney, Agent, or Firm* — Hoffmann & Baron, LLP

(57) ABSTRACT

A therapeutic or bioeffecting film delivery system which includes nanoparticles having actives bound to or associated with the nanoparticles and which when administered allow the active to perform a therapeutic or bioeffecting function.

123 Claims, 26 Drawing Sheets

(51) Int. Cl.
  *A61K 9/00*    (2006.01)
  *A61K 9/20*    (2006.01)
  *A61K 9/70*    (2006.01)
  *A61K 47/48*   (2006.01)
  *B82Y 5/00*    (2011.01)

(52) U.S. Cl.
  CPC ........ *A61K 9/7007* (2013.01); *A61K 47/48861* (2013.01); *A61K 47/4893* (2013.01); *B82Y 5/00* (2013.01); *A61K 38/00* (2013.01); *Y10S 977/906* (2013.01); *Y10S 977/773* (2013.01)
  USPC ............ 424/484; 977/906; 977/773; 514/1.1; 514/10.2

(56) References Cited

U.S. PATENT DOCUMENTS

| | | |
|---|---|---|
| 2,980,554 A | 4/1961 | Gentile et al. |
| 3,007,848 A | 11/1961 | Stroop |
| 3,249,109 A | 5/1966 | Maeth et al. |
| 3,444,858 A | 5/1969 | Russell |
| 3,536,809 A | 10/1970 | Applezweig |
| 3,551,556 A | 12/1970 | Kliment et al. |
| 3,598,122 A | 8/1971 | Zaffaroni |
| 3,632,740 A | 1/1972 | Robinson et al. |
| 3,640,741 A | 2/1972 | Etes |
| 3,641,237 A | 2/1972 | Gould et al. |
| 3,731,683 A | 5/1973 | Zaffaroni |
| 3,753,732 A | 8/1973 | Boroshok |
| 3,814,095 A | 6/1974 | Lubens |
| 3,892,905 A | 7/1975 | Albert |
| 3,911,099 A | 10/1975 | DeFoney et al. |
| 3,972,995 A | 8/1976 | Tsuk et al. |
| 3,996,934 A | 12/1976 | Zaffaroni |
| 4,029,757 A | 6/1977 | Mlodozeniec et al. |
| 4,029,758 A | 6/1977 | Mlodozeniec et al. |
| 4,031,200 A | 6/1977 | Reif |
| 4,123,592 A | 10/1978 | Rainer et al. |
| 4,128,445 A | 12/1978 | Sturzenegger et al. |
| 4,136,145 A | 1/1979 | Fuchs et al. |
| 4,136,162 A | 1/1979 | Fuchs et al. |
| 4,139,627 A | 2/1979 | Lane et al. |
| 4,226,848 A | 10/1980 | Nagai et al. |
| 4,251,400 A | 2/1981 | Columbus |
| 4,292,299 A | 9/1981 | Suzuki et al. |
| 4,294,820 A | 10/1981 | Keith et al. |
| 4,302,465 A | 11/1981 | AF Ekenstam et al. |
| 4,307,075 A | 12/1981 | Martin |
| 4,325,855 A | 4/1982 | Dickmann et al. |
| 4,373,036 A | 2/1983 | Chang et al. |
| 4,406,708 A | 9/1983 | Hesselgren |
| 4,432,975 A | 2/1984 | Libby |
| 4,438,258 A | 3/1984 | Graham |
| 4,460,562 A | 7/1984 | Keith et al. |
| 4,466,973 A | 8/1984 | Rennie |
| 4,503,070 A | 3/1985 | Eby, III |
| 4,515,162 A | 5/1985 | Yamamoto et al. |
| 4,517,173 A | 5/1985 | Kizawa et al. |
| 4,529,601 A | 7/1985 | Broberg et al. |
| 4,529,748 A | 7/1985 | Wienecke |
| 4,562,020 A | 12/1985 | Hijiya et al. |
| 4,569,837 A | 2/1986 | Suzuki et al. |
| 4,593,053 A | 6/1986 | Jevne et al. |
| 4,608,249 A | 8/1986 | Otsuka et al. |
| 4,615,697 A | 10/1986 | Robinson |
| 4,623,394 A | 11/1986 | Nakamura et al. |
| 4,631,837 A | 12/1986 | Magoon |
| 4,652,060 A | 3/1987 | Miyake |
| 4,659,714 A | 4/1987 | Watt-Smith |
| 4,675,009 A | 6/1987 | Hymes et al. |
| 4,695,465 A | 9/1987 | Kigasawa et al. |
| 4,704,119 A | 11/1987 | Shaw et al. |
| 4,713,239 A | 12/1987 | Babaian et al. |
| 4,713,243 A | 12/1987 | Schiraldi et al. |
| 4,722,761 A | 2/1988 | Cartmell et al. |
| 4,740,365 A | 4/1988 | Yukimatsu et al. |
| 4,748,022 A | 5/1988 | Busciglio |
| 4,765,983 A | 8/1988 | Takayanagi et al. |
| 4,772,470 A | 9/1988 | Inoue et al. |
| 4,777,046 A | 10/1988 | Iwakura et al. |
| 4,789,667 A | 12/1988 | Makino et al. |
| 4,849,246 A | 7/1989 | Schmidt |
| 4,860,754 A | 8/1989 | Sharik et al. |
| RE33,093 E | 10/1989 | Schiraldi et al. |
| 4,876,092 A | 10/1989 | Mizobuchi et al. |
| 4,876,970 A | 10/1989 | Bolduc |
| 4,888,354 A | 12/1989 | Chang et al. |
| 4,894,232 A | 1/1990 | Reül et al. |
| 4,900,552 A | 2/1990 | Sanvordeker et al. |
| 4,900,554 A | 2/1990 | Yanagibashi et al. |
| 4,900,556 A | 2/1990 | Wheatley et al. |
| 4,910,247 A | 3/1990 | Haldar et al. |
| 4,915,950 A | 4/1990 | Miranda et al. |
| 4,925,670 A | 5/1990 | Schmidt |
| 4,927,634 A | 5/1990 | Sorrentino et al. |
| 4,927,636 A | 5/1990 | Hijiya et al. |
| 4,937,078 A | 6/1990 | Mezei et al. |
| 4,940,587 A | 7/1990 | Jenkins et al. |
| 4,948,580 A | 8/1990 | Browning |
| 4,958,580 A | 9/1990 | Asaba et al. |
| 4,978,531 A | 12/1990 | Yamazaki et al. |
| 4,981,693 A | 1/1991 | Higashi et al. |
| 4,981,875 A | 1/1991 | Leusner et al. |
| 5,023,082 A | 6/1991 | Friedman et al. |
| 5,024,701 A | 6/1991 | Desmarais |
| 5,028,632 A | 7/1991 | Fuisz |
| 5,045,445 A | 9/1991 | Schultz |
| 5,047,244 A | 9/1991 | Sanvordeker et al. |
| 5,064,717 A | 11/1991 | Suzuki et al. |
| 5,089,307 A | 2/1992 | Ninomiya et al. |
| 5,158,825 A | 10/1992 | Altwirth |
| 5,166,233 A | 11/1992 | Kuroya et al. |
| 5,186,938 A | 2/1993 | Sablotsky et al. |
| 5,229,164 A | 7/1993 | Pins et al. |
| 5,234,957 A | 8/1993 | Mantelle |
| 5,271,940 A | 12/1993 | Cleary et al. |
| 5,272,191 A | 12/1993 | Ibrahim et al. |
| 5,346,701 A | 9/1994 | Heiber et al. |
| 5,393,528 A | 2/1995 | Staab |
| 5,411,945 A | 5/1995 | Ozaki et al. |
| 5,413,792 A | 5/1995 | Ninomiya et al. |
| 5,433,960 A | 7/1995 | Meyers |
| 5,455,043 A | 10/1995 | Fischel-Ghodsian |
| 5,462,749 A | 10/1995 | Rencher |
| 5,472,704 A | 12/1995 | Santus et al. |
| 5,518,902 A | 5/1996 | Ozaki et al. |
| 5,567,431 A | 10/1996 | Vert et al. |
| 5,605,696 A | 2/1997 | Eury et al. |
| 5,620,757 A | 4/1997 | Ninomiya et al. |
| 5,629,003 A | 5/1997 | Horstmann et al. |
| 5,681,873 A | 10/1997 | Norton et al. |
| 5,700,478 A | 12/1997 | Biegajski et al. |
| 5,700,479 A | 12/1997 | Lundgren |
| 5,766,332 A | 6/1998 | Graves et al. |
| 5,766,620 A | 6/1998 | Heiber et al. |
| 5,766,839 A | 6/1998 | Johnson et al. |
| 5,800,832 A | 9/1998 | Tapolsky et al. |
| 5,806,284 A | 9/1998 | Gifford |
| 5,900,247 A | 5/1999 | Rault et al. |
| 5,948,430 A | 9/1999 | Zerbe et al. |
| 6,072,100 A | 6/2000 | Mooney et al. |
| 6,153,210 A | 11/2000 | Roberts et al. |
| 6,177,096 B1 | 1/2001 | Zerbe et al. |
| 6,231,957 B1 | 5/2001 | Zerbe et al. |
| 6,284,264 B1 | 9/2001 | Zerbe et al. |
| 6,375,963 B1 | 4/2002 | Repka et al. |
| 6,503,532 B1 | 1/2003 | Murty et al. |
| 6,800,329 B2 | 10/2004 | Horstmann et al. |
| 6,824,829 B2 | 11/2004 | Berry et al. |
| 7,005,142 B2 | 2/2006 | Leon |
| 7,279,457 B2 | 10/2007 | Pohl et al. |
| 7,579,019 B2 | 8/2009 | Tapolsky et al. |
| 8,425,915 B2 * | 4/2013 | Rademacher et al. ..... 424/194.1 |
| 2001/0006677 A1 | 7/2001 | McGinity et al. |

(56) References Cited

U.S. PATENT DOCUMENTS

| | | |
|---|---|---|
| 2001/0022964 A1 | 9/2001 | Leung et al. |
| 2001/0046511 A1 | 11/2001 | Zerbe et al. |
| 2003/0107149 A1 | 6/2003 | Yang et al. |
| 2004/0096569 A1 | 5/2004 | Barkalow et al. |
| 2004/0191302 A1 | 9/2004 | Davidson |
| 2005/0048102 A1 | 3/2005 | Tapolsky et al. |
| 2005/0192309 A1 | 9/2005 | Palermo et al. |
| 2006/0210610 A1 | 9/2006 | Davidson et al. |
| 2007/0087036 A1 | 4/2007 | Durshlag et al. |
| 2007/0148097 A1 | 6/2007 | Finn et al. |
| 2008/0090753 A1 | 4/2008 | Pohl et al. |
| 2008/0096800 A1 | 4/2008 | Pohl et al. |
| 2008/0248999 A1 | 10/2008 | Steiner |

FOREIGN PATENT DOCUMENTS

| | | |
|---|---|---|
| DE | 3630603 C2 | 3/1988 |
| EP | 0219762 B1 | 12/1990 |
| EP | 0259749 B1 | 8/1991 |
| EP | 0200508 B1 | 10/1991 |
| EP | 0241178 B1 | 1/1992 |
| EP | 0273069 B1 | 10/1992 |
| EP | 0250187 B1 | 9/1993 |
| EP | 0452446 B1 | 12/1993 |
| EP | 0381194 B1 | 8/1994 |
| EP | 0440462 B1 | 12/1994 |
| EP | 0514691 B1 | 3/1996 |
| EP | 0598606 B1 | 6/1999 |
| EP | 0949925 B1 | 10/1999 |
| EP | 1110546 A1 | 6/2001 |
| EP | 1897543 A1 | 3/2008 |
| EP | 2 305 310 A1 | 4/2011 |
| JP | 62126950 | 6/1987 |
| JP | 02265444 | 10/1990 |
| JP | 05147140 | 6/1993 |
| JP | 07322812 | 12/1995 |
| JP | 2001279100 | 10/2001 |
| WO | 9105540 A1 | 5/1991 |
| WO | 9215289 A1 | 9/1992 |
| WO | 9505416 A2 | 2/1995 |
| WO | 9518046 A1 | 7/1995 |
| WO | 9534294 A1 | 12/1995 |
| WO | 9749386 A1 | 12/1997 |
| WO | 0018365 A2 | 4/2000 |
| WO | 0042992 A2 | 7/2000 |
| WO | 0170194 A1 | 9/2001 |
| WO | 0191721 A2 | 12/2001 |
| WO | 03030881 A1 | 4/2003 |
| WO | 03030883 A1 | 4/2003 |
| WO | 03057170 A2 | 7/2003 |
| WO | 03086345 A1 | 10/2003 |
| WO | 2009048945 A1 | 4/2004 |
| WO | 2004056314 A2 | 7/2004 |
| WO | 2006/037979 A2 | 4/2006 |
| WO | WO 2006037979 A2 * | 4/2006 |
| WO | 2007/015105 A2 | 2/2007 |
| WO | WO 2007015105 A2 * | 2/2007 |
| WO | WO 2007/036946 A1 * | 5/2007 |
| WO | 2008011194 A2 | 1/2008 |
| WO | 2008124522 A2 | 10/2008 |
| WO | 2009048959 A1 | 4/2009 |
| WO | WO 2009048945 A1 * | 4/2009 |

OTHER PUBLICATIONS

International Search Report for International Application No. PCT/GB2011/000882 dated Oct. 13, 2011.
Bhumkar et al., Chitosan Reduced Gold Nanoparticles as Novel Carriers for Transmucosal Delivery of Insulin, Pharmaceutical Research, vol. 24, No. 8, pp. 1415-1426, Aug. 2007.
Joshi et al., Gold Nanoparticles as Carriers for Efficient Transmucosal Insulin Delivery, Langmuir: The ACS Journal of Surfaces and Colloids, American Chemical Society, pp. 300-305, (2006).
Ojeda et al., Preparation of multifunctional glyconanoparticles as a platform for potential carbohydrate-based anticancer vaccines, Carbohydrate Research 342 pp. 448-459, (2007).
Peh and Wong, Polymeric Films as Vehicle for Buccal Delivery: Swelling, Mechanical, and Bioadhesive Properties, J Pharm Pharmaceut Sci (www.ualberta.ca/~csps) 2 (2):53-61, 1999.
Bodmeier. Pharmaceutical Research, vol. 6, No. 8, 1989.
Lazaridou et al., "Thermophysical proprties of chitosan, chitosan-starch and chitosan-pullulan films near the glass transition," Carbohydrate Polymers 48: 179-190 (2002).
Repka et al., "Bioadhesive Properties of hydroxypropylcellulose topical films produced by hot melt extrusion," Journal of Controlled Release, 70: 341-351 (2001).
Repka et al., "Influence of Vitamin E TPGS on the properties of hydrophilic films produced by hot melt extrusion", International Journal of Pharmaceutics 202: 63-70 (2000).

* cited by examiner

NANOPARTICLE FILM DELIVERY SYSTEMS

The subject matter of this application was made by or on behalf of MonoSol Rx, LLC and Midatech Limited pursuant to a joint research agreement. The joint research agreement was in effect before the date the present invention was made, and the invention was made as a result of activities undertaken within the scope of the joint research agreement.

FIELD OF THE INVENTION

The present invention relates to film delivery systems comprising nanoparticles, particularly for use in medicine, and includes methods and systems for treatment of disorders of blood glucose regulation.

BACKGROUND TO THE INVENTION

The present invention is directed at compositions, delivery systems, products and methods of making and administering such compositions, delivery systems and products made therefrom for the treatment of mammals and particularly humans.

Delivery of certain pharmaceuticals, biologically active agents, cosmaceuticals, nutraceuticals and other actives using film is described in U.S. Pat. Nos. 7,357,891, 7,425,292 and 7,666,337, among others. However, films which are intended for ingestion are not particularly suitable for actives which get destroyed, inactivated in the GI tract, or are simply not well absorbed through such administration. Many biological agents, such as insulin, are particularly susceptible to destruction when ingested and are thus normally given by injection.

There is a need for a film delivery system which overcomes the difficulties associated with oral delivery of the active to the circulatory system without exposure to the gastrointestinal tract. More particularly, there is need for overcoming the difficulties associated with, effective oral delivery of biologicals, such as certain peptides, through for example buccal administration.

BRIEF DESCRIPTION OF THE INVENTION

The present invention overcomes the aforementioned difficulties by providing a film delivery system which facilitates vectoral transport of the active-carrying component, through for example buccal administration, thus allowing the active-carrying component to become delivered into the circulatory system without exposure to the gastrointestinal tract of the patient. The present invention also addresses the problem of providing a suitable active-carrying component for delivery of active agents such as peptides, i.e., a component which is linked to, bound to, associated with or otherwise coupled to an active.

The present invention provides a film delivery system particularly useful for, although not limited to, oral delivery. In particular, this film delivery system of the present invention, although not limited to a particular use, is especially well suited for buccal, sublingual, and other mucosal tissue, as well as organ tissue use. Film products made from the delivery system incorporate water soluble and/or water swellable polymers which form at least one matrix, desirably along with a suitable solvent, and further incorporate nanoparticles which as described herein, include a metal core, a corona of ligands and an active attached to one or more ligands. This delivery system is especially useful for delivery of actives which are not well suited for delivery through the GI tract.

In one aspect of the invention, there is provided a therapeutic or bioaffecting film delivery system which includes:
(a) one or more film matrices including at least one polymer;
(b) a plurality of nanoparticles incorporated in at least one of said film matrices, said nanoparticles including:
  (i) a core which includes a metal; and
  (ii) a corona including a plurality of ligands covalently linked to the core, wherein at least one of said ligands includes a carbohydrate moiety; and
  (iii) wherein at least one peptide is bound to the corona.

In another aspect of the invention there is provided an insulin-containing film delivery system including:
(a) one or more film matrices including at least one polymer;
(b) a plurality of nanoparticles incorporated in at least one of said film matrices, said nanoparticles including:
  (i) a core including a gold;
  (ii) a plurality of ligands covalently attached to the core and forming a corona around the core, wherein the ligands comprise 2'-thioethyl-α-D-galactopyranoside and 1-amino-17-mercapto-3,6,9,12,15-pentaoxa-heptadecanol each bonded to the core via their respective sulphur atoms, and wherein the nanoparticles have an average of at least five insulin monomers bound per nanoparticle core.

In yet another aspect of the invention there is provided a process for making a film having a substantially uniform distribution of components, including the steps of:
(a) forming a flowable polymer matrix including a water-soluble or water swellable polymer, a solvent and an active-carrying component, said active-carrying component including a plurality of nanoparticles including:
  (i) a core including a metal;
  (ii) a corona including a plurality of ligands covalently linked to the core, wherein at least one of said ligands comprises a carbohydrate moiety; and
  (iii) a peptide bound to the corona;
said matrix having a uniform distribution of said active-carrying component;
(b) casting said flowable polymer matrix;
(c) evaporating at least a portion of said solvent from said flowable polymer matrix to form a visco-elastic film within about 10 minutes or fewer to maintain said uniform distribution of said active-carrying component by locking-in or substantially preventing migration of said active-carrying component within said visco-elastic film; and
(d) forming a resulting film from said visco-elastic film, wherein said resulting film has a water content of 10% or less and said uniform distribution of active-carrying component by said locking-in or substantially preventing migration of said active-carrying component is maintained. A further step may be added for forming additional layers of film disposed over the initial layer.

In still another aspect of the invention there is provided a process for making a film having a substantially uniform distribution of components, including the steps of:
(a) forming a masterbatch pre-mix including a solvent and a polymer selected from the group of water-soluble polymers, water-swellable polymers and combinations thereof;
(b) adding an active-carrying component to a pre-determined amount of said masterbatch pre-mix to form a flowable polymer matrix, said active-carrying component including a plurality of nanoparticles including:

(i) a core including a metal;
(ii) a corona including a plurality of ligands covalently linked to the core, wherein at least one of said ligands includes a carbohydrate moiety; and
(iii) a peptide bound to the corona; said matrix having a uniform distribution of said active-carrying component;

(c) casting said flowable polymer matrix;
(d) evaporating at least a portion of said solvent from said flowable polymer matrix to form a visco-elastic film within about 10 minutes or fewer to maintain said uniform distribution of said active-carrying component by locking-in or substantially preventing migration of said active-carrying component within said visco-elastic film; and
(e) forming a resulting film from said visco-elastic film, wherein said resulting film has a water content of 10% or less and said uniform distribution of active-carrying component by said locking-in or substantially preventing migration of said active-carrying component is maintained.

In yet another aspect of the invention, there is provided an article of manufacture including at least one film including;
(a) one or more film matrices including at least one polymer;
(b) a plurality of nanoparticles incorporated in at least one of said film matrices, said nanoparticles including:
(i) a core including a metal;
(ii) a corona including a plurality of ligands covalently linked to the core, wherein at least one of said ligands includes a carbohydrate moiety; and
(iii) a peptide bound to the corona; and
said at least one film has a water content of about 10% or less by weight of the at least one film and a variance per unit volume of the plurality of nanoparticles or peptide content per unit volume of no greater than about 10% or less by weight of the at least one film.

There is further provided an article of manufacture including:
at least one film delivery system as defined in any one of the inventive embodiments herein;
a container for housing the at least one film delivery system of film; and
optionally, an insert and/or a label.

The present invention includes the combination of the aspects and preferred features described except where such a combination is clearly impermissible or is stated to be expressly avoided. These and further aspects and embodiments of the invention are described in further detail below and with reference to the accompanying examples and figures.

DETAILED DESCRIPTION OF THE INVENTION

Figure 1:
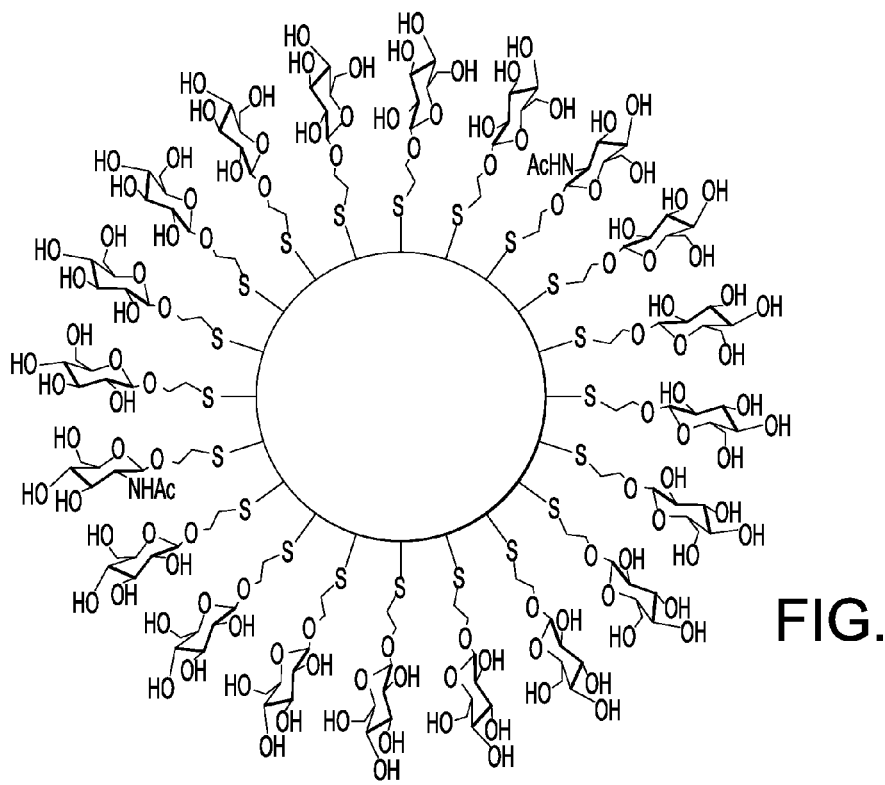
FIG. 1 shows a schematic representation of nanoparticles having a plurality of ligands in the ratio 9:1 of GlcC2:GlcNAc "NP-GlcC2(9) GlcNAc(1)"

In describing the present invention, the following terms will be employed, and are intended to be defined as indicated below.

As used herein, "nanoparticle" refers to a particle having a nanomeric scale, and is not intended to convey any specific shape limitation. In particular, "nanoparticle" encompasses nanospheres, nanotubes, nanoboxes, nanoclusters, nanorods and the like. In certain embodiments the nanoparticles and/or nanoparticle cores contemplated herein have a generally polyhedral or spherical geometry.

Nanoparticles comprising a plurality of carbohydrate-containing ligands have been described in, for example, WO 2002/032404, WO 2004/108165, WO 2005/116226, WO 2006/037979, WO 2007/015105, WO 2007/122388, WO 2005/091704 (the entire contents of each of which is expressly incorporated herein by reference) and such nanoparticles may find use in accordance with the present invention. Moreover, gold-coated nanoparticles comprising a magnetic core of iron oxide ferrites (having the formula $XFe_2O_4$, where X=Fe, Mn or Co) functionalised with organic compounds (e.g. via a thiol-gold bond) are described in unpublished European patent application No. EP09382185.8 filed 25 Sep. 2009 (the entire contents of which is expressly incorporated herein by reference) and are specifically contemplated for use as nanoparticles/nanoparticle cores in accordance with the present invention.

As used herein, "corona" refers to a layer or coating, which may partially or completely cover the exposed surface of the nanoparticle core. The corona includes a plurality of ligands which include at least one carbohydrate moiety. Thus, the corona may be considered to be an organic layer that surrounds or partially surrounds the metallic core. In certain embodiments the corona provides and/or participates in passivating the core of the nanoparticle. Thus, in certain cases the corona may include a sufficiently complete coating layer substantially to stabilise the metal-containing core. However, it is specifically contemplated herein that certain nanoparticles having cores, e.g., that include a metal oxide-containing inner core coated with a noble metal may include a corona that only partially coats the core surface.

As used herein, "peptide" is intended to encompass any sequence of amino acids and specifically includes peptides, polypeptides proteins (including proteins having secondary, tertiary and/or quaternary structure) and fragments thereof. The expression "peptide bound to" is specifically intended to encompass a part (but may include the whole) of the amino acid sequence of the peptide forming a bonding interaction with one or more parts (such as a chemical group or moiety) of one or more of the plurality of ligands of the nanoparticle.

In certain embodiments the peptide may have a molecular weight of <500 kDa, <100 kDa, <50 kDa, such as up to 20 kDa.

As used herein, the terms "active-carrying component" or "active-containing component" are used interchangeably and are intended to encompass a component which is linked to, coupled to, bound to or otherwise intimately associated with, either physically and/or chemically, an active, and particularly a pharmaceutical or biological agent, for the purpose of delivering the active to the patient.

The term "film" includes delivery systems of any thickness, including films, sheets, discs, wafers, and the like, in any shape, including rectangular, square, or other desired shape. The film may be in the form of a continuous roll of film or may be sized to a desired length and width. The films described herein may be any desired thickness and size suitable for the intended use. For example, a film of the present invention may be sized such that it may be placed into the oral cavity of the user or adhered to mucosal or organ tissue. For example, some films may have a relatively thin thickness of from about 0.1 to about 10 mils, while others may have a somewhat thicker thickness of from about 10 to about 30 mils. For some films, the thickness may be even larger, i.e., greater than about 30 mils. It will be understood, of course, that the thickness of the film may be limited due to the formulation used, and thicker films may require longer drying times or different manufacturing techniques.

Further, thicker films may desirably be formed through lamination of thinner films. In addition, the term "film" includes single-layer compositions as well as multi-layer compositions, such as laminated films, coatings on films and the like. For example, two or more films may be separately formed and then laminated together using, for example, heat and/or solvent to form a thicker film. Additionally, multiple layers of film may be made by coating a first film with additional film layers, without necessarily the need for lamination steps. Multiple layers of film made be added to form structures of various thicknesses and also to allow for different functions and properties of the different layers. The composition, regardless of thickness, maintains a uniform distribution of components through the application of controlled drying of the film to provide a final film which in its dried form has uniformity of active-carrying component throughout the film, as described herein. The films of the present invention will not vary in active-carrying component content of more than 10% by weight in any given volume of film. For example, unit doses of equal or random sizes will contain substantially the same amount by weight of active-carrying component, with no more than a variation of 10% by weight between the doses. Film structures of the present invention may also include a pouch or region of drug between two films.

The nanoparticles described herein may be dispersed throughout the film, or may be deposited onto one or more surfaces of the film. In either way, the amount of nanoparticles per unit area is desirably substantially uniform throughout the film. It is desired that the films of the present invention include a uniformity of component distribution throughout the volume of a given film. Such uniformity includes a substantially uniform amount of nanoparticles per unit volume of the film and/or a substantially uniform amount of pharmaceutical or biological active (for example, a peptide) associated with the nanoparticles per unit volume of the film, whether the nanoparticles are within the matrix of the film or coated, laminated, deposited or stabilized on one or more surfaces thereof. When such films are cut into individual units, the amount of nanoparticles in the unit can be known with a great deal of accuracy.

Uniformity of components throughout the film, i.e. uniformity of content, is beneficial in administering an accurate and effective dose to a user. Various methods of forming uniform films, as well as various additives and fillers, may be used, including those methods and materials described in U.S. Pat. Nos. 7,425,292, 7,357,891, and 7,666,337, which are herein incorporated by reference in their entireties. In some particularly desirable embodiments, the amount of active-carrying component, or the amount of active per se, per unit volume does not vary more than about 10%, as discussed above. Thus a large sheet of film may be made and equally sized dosage units cut therefrom and the amount of active-carrying component or active per se in each dosage unit will not vary more than 10% by weight between units.

Accordingly, in one aspect the present invention provides a therapeutic or bioaffecting film delivery system which includes:
  (a) one or more film matrices including at least one polymer;
  (b) a plurality of nanoparticles incorporated in at least one of said film matrices, said nanoparticles including:
    (i) a core which includes a metal;
    (ii) a corona which includes a plurality of ligands covalently linked to the core, wherein at least one of said ligands includes a carbohydrate moiety; and
    (iii) at least one peptide bound to the corona.

The term "bound" is intended to include a physical and/or a chemical association between two components. This term includes any form of chemical linkage, e.g., covalent, ionic, hydrogen bonding or intermolecular forces, such as van der Waals forces or electrostatic forces. The term includes physical coupling or linking. This physical and or chemical association may be intended to be reversible, i.e., the component may be separated or disassociated, one from the other, e.g., to release the active component from the carrier component.

The term "mucous membrane" or "mucosal tissue" is meant to include, without limitation, the membrane lining that all body passages have that communicate with the exterior, such as the respiratory, genitourinary, and alimentary tracts, and having cells and associated glands that secrete mucus. The term "organ tissue" is intended to include any grouping of tissues which form a distinct structure and function in an animal or human body, excluding the outermost, epidermis layer of the skin. For example, the heart, kidney and liver are examples of organ tissue.

One or more peptides may be reversibly bound to the corona. In particular it is specifically contemplated that the peptide may be bound to a part of the nanoparticle non-covalently. Without wishing to be bound by any theory, it is presently believed that a peptide may participate in one or more reversible binding interactions with one or more ligands that provide the corona of the nanoparticle. In particular, a portion of the sequence of amino acids may participate in hydrogen bonding, Van der Waals forces and/or electrostatic interactions with one or more ligands (e.g. interacting with one or more functional groups of an exposed ligand). The peptide binding may involve adsorption, absorption or other direct or indirect interaction with one or more ligands of the nanoparticle.

As described herein with reference to certain embodiments of the present invention, one or more peptides may be bound such that at least a fraction or portion of the bound peptide is released from the nanoparticle upon contacting the nanoparticle with a physiological solution. As described herein the peptide may be bound to the nanoparticle in a manner such that the peptide is stabilised (e.g. thermostabilised) while bound, but is releasable and available in a form that is biologically active (for example, releasable such that the peptide is detectable by ELISA and/or capable of exerting at least one biological action in an in vitro or in vivo system that is characteristic of the free peptide). In particular, when the peptide includes (human) insulin, the peptide may be bound to the nanoparticle such that a suspension of the insulin-bound nanoparticles gives a positive result in an ELISA for (human) insulin and/or exerts an effect on blood glucose levels in a mammalian subject following administration thereto.

A variety of release kinetics are contemplated for dissociation of bound peptide molecule(s) from the nanoparticle, including bi- or multi-phase release (such as an initial fast release followed by a slower subsequent release phase). For example, the release may include dissociation of bound peptide molecules from the nanoparticle rapidly within seconds or minutes followed by further sustained release over a period of at least 2, 4, 6, 8 or more hours. Such release kinetics may be advantageous in certain circumstances, e.g. where sustained action is desired, in comparison with, e.g., an injection of free peptide.

The peptide (including without limitation polypeptide, protein, or fragment thereof) may be selected from the group consisting of: insulin, GLP-1, IGF1, IGF2, relaxin, INSL5, INSL6, INSL7, pancreatic polypeptide (PP), peptide tyrosine tyrosine (PTT), neuropeptide Y, oxytocin, vasopressin, GnRH, TRH, CRH, GHRH/somatostatin, FSH, LH, TSH, CGA, prolactin, ClIP, ACTH, MSH, endorphins, lipotropin, GH, calcitonin, PTH, inhibin, relaxin, hCG, HPL, glucagons, somatostatin, melatonin, thymosin, thmulin, gastrin, ghrelin, thymopoietin, CCK, GIP secretin, motin VIP, enteroglucagon, leptin, adiponectin, resistin, osteocalcin, renin, EPO, calicitrol, ANP, BNP, chemokines, cytokines, adipokines and biologically active analogs thereof. In certain embodiments the peptide is capable of stimulating a reduction in blood glucose levels in a mammalian subject. Thus, in some cases in accordance with the present invention the peptide may include monomeric and/or dimeric human insulin. Furthermore, the at least one peptide may comprise a combination of two or more peptides specified above, e.g. insulin and GLP-1.

In certain cases in accordance with the present invention there may be at least 1, at least 2, at least 3, at least 4, at least 5, at least 10 or more peptide molecules bound per core on average. There may be a single type of peptide or two or more different peptides. Where a combination of two different peptides are bound to a nanoparticle, the different peptides may in some cases be present in a ratio of 1:10 to 10:1, such as 1:2 to 2:1. Thus, complementary combinations of peptides that are advantageously co-administered are specifically contemplated.

As used herein the term "carbohydrate"" is intended to include compounds of the general formula $C_n(H_2O)_m$ where n=m and n is greater than 3. Also, included within the definition of carbohydrate are carbohydrate analogues/mimetics that are not included in the general formula $C_n(H_2O)_m$. The carbohydrate analogues/mimetics include but are not limited to pseudo-sugars (carba-sugars), amino-sugars, imino-sugars and inositols. Amino-sugars include polyhydroxylated piperidines, pyrrolidines, pyrrolizidines and indolizidines.

As described herein the nanoparticle in accordance with the present invention includes a plurality of ligands covalently linked to a metal-containing core. The ligands may be the same or different. In particular embodiments, the plurality of ligands may include a first class of ligands including at least one carbohydrate moiety and a second class of non-carbohydrate ligands. As used herein the at least one ligand including carbohydrate moiety will generally include one or more sugar groups, such as a monosaccharide, a disaccharide and/or a polysaccharide and/or one or more pseudo-sugar groups (such as pseudo sugar selected from: a carba-sugar, an amino-sugar, an imino-sugar, an inositol, a polyhydroxylated piperidine, a pyrrolidine, a pyrrolizidine and an indolizidine). The ligands are covalently linked to the core of the nanoparticle. Therefore, the term "carbohydrate moiety" is to be understood to include chemical derivatives of carbohydrates such as glycosides wherein the ligand includes a sugar group or pseudo-sugar group (such as pseudo sugar selected from: a carba-sugar, an amino-sugar, an imino-sugar, an inositol, a polyhydroxylated piperidine, a pyrrolidine, a pyrrolizidine and an indolizidine) attached to a non-sugar atom or molecule. In particular cases, the ligand including a carbohydrate moiety in accordance with the present invention may include a glycoside of galactose, glucose, glucosamine, N-acetylglucosamine, mannose, fucose and/or lactose, e.g. the carbohydrate moiety may include a galactopyranoside and/or a glucopyranoside. The carbohydrate-containing ligand may be covalently linked to the core via a linker selected from sulphur-containing linkers, amino-containing linkers and phosphate-containing linkers. Combinations of linkers off of the core may also be used. The linker may in some cases include an alkyl chain of at least two carbons.

The ligand linked to the core includes one or more carbohydrate (saccharide) groups, e.g. including a polysaccharide, an oligosaccharide or a single saccharide group. The ligand may also be a glycanoconjugate such as a glycolipid or a glycoprotein. In addition to the carbohydrate group, the ligand may additionally include one or more of a peptide group, a protein domain, a nucleic acid molecule (e.g. a DNA/RNA segment) and/or a fluorescent probe.

In certain cases the particles may have more than one species of ligand immobilised thereon, e.g. 2, 3, 4, 5, 10, 20 or 100 different ligands. Alternatively or additionally a plurality of different types of particles can be employed together.

In certain cases, the mean number of ligands linked to an individual metallic core of the particle is at least 5, at least 10 or at least 20 ligands. The number may be in the range 10 to 10,000 such as 10 to 1,000, more particularly 20 to 500 or 44 to 106 ligands per core.

Preferably, substantially all of the ligands are attached covalently to the core of the particles. Protocols for carrying this out are known in the art (see, e.g. WO 2002/032404, WO 2004/108165, WO 2005/116226, WO 2006/037979, WO 2007/015105, WO 2007/122388, WO 2005/091704). This may be carried out by reacting ligands with reductive end groups with a noble metal such as gold under reducing conditions. An exemplary method of producing the particles employs thiol derivatised carbohydrate moieties to couple the ligands to particles. Thus, the ligand is derivatised as a protected disulphide. Conveniently, the disulphide protected ligand in methanol can be added to an aqueous solution of tetrachloroauric acid. A preferred reducing agent is sodium borohydride. In certain embodiments, the nanoparticles are soluble in organic solvents and in water and physiological solutions. The present inventors have found that the nanoparticles as described herein are suitable for therapeutic applications, and may be non-toxic, soluble and/or excreted in the urine.

In certain cases in accordance with the present invention, the at least one ligand comprising a carbohydrate moiety is selected from the group of: 2'-thioethyl-α-D-galactopyranoside, 2'-thioethyl-β-D-glucopyranoside, 2'-thioethyl-2-acetamido-2-deoxy-α-D-glucopyranoside, 5'-thiopentanyl-2-deoxy-2-imidazolacetamido-α,β-D-glucopyranoside and 2'-thioethyl-α-D-glucopyranoside, and wherein said at least one ligand comprising a carbohydrate moiety is covalently linked to the core via the thiol sulphur.

Additionally or alternatively, the plurality of ligands may include an amine group. Thus, a ligand comprising a carbohydrate group may include an amine group (e.g. as part of the carbohydrate, such as a glucosamine, and/or as a constituent group of a non-carbohydrate part of the ligand. Moreover, where the plurality of ligands includes at least one non-carbohydrate ligand, the non-carbohydrate group may include an amine group. The at least one non-carbohydrate ligand may include 1-amino-17-mercapto-3,6,9,12,15-pentaoxa-heptadecanol covalently linked to the core via the thiol sulphur.

In accordance with certain embodiments of the present invention, the plurality of ligands may include said at least one ligand including a carbohydrate moiety and said at least one non-carbohydrate ligand wherein the said ligands are different and are present on the nanoparticle in a ratio of 1:40 to 40:1, such as a ratio of 1:10 to 10:1, more particularly a ratio of 1:2 to 2:1.

The nanoparticle "core" includes a metal. Suitable cores are described in, e.g., WO 2002/032404, WO 2004/108165, WO 2005/116226, WO 2006/037979, WO 2007/015105, WO 2007/122388, WO 2005/091704 (the entire contents of each of which is expressly incorporated herein by reference) and such nanoparticle cores may find use in accordance with the present invention. Moreover, gold-coated nanoparticles including a magnetic core of iron oxide ferrites (having the formula $XFe_2O_4$, where X=Fe, Mn or Co) are described in unpublished European patent application No. EP09382185.8 filed 25 Sep. 2009 (the entire contents of which is expressly incorporated herein by reference) and may find use in accordance with the present invention.

In some cases in accordance with the present invention the nanoparticle core includes a metal selected from the group of: Au, Ag, Cu, Pt, Pd, Fe, Co, Gd, Zn or any combination thereof. The core may include a passive metal selected from the group of: Au, Ag, Pt, Pd and Cu, or any combination thereof. In certain embodiments a specific combination of metals may be employed, such as a combination of metals selected from the group of: Au/Fe, Au/Ag, Au/Cu, Au/Ag/Cu, Au/Pt, Au/Pd, Au/Ag/Cu/Pd, Au/Gd, Au/Fe/Cu, Au/Fe/Gd, Au/Fe/Cu/Gd.

In some cases in accordance with the present invention the nanoparticle core may be magnetic. The core may include an NMR active atom, such as a metal selected from the group of: $Mn^{2+}$, $Gd^{3+}$, $Eu^{2+}$, $Cu^{2+}$, $V^{2+}$, $Co^{2+}$, $Ni^{2+}$, $Fe^{2+}$, $Fe^{3+}$ and lanthanides$^{3+}$.

In some cases in accordance with the present invention the nanoparticle core may include a semiconductor, such as that selected from the group of: cadmium selenide, cadmium sulphide, cadmium tellurium and zinc sulphide.

In some cases in accordance with the present invention the nanoparticle core may include a metal oxide coated with a metal selected from the group of: Au, Ag, Cu, Pt, Pd and Zn, or any combination thereof. The metal oxide may advantageously be of the formula $XFe_2O_4$, where X is a metal selected from the group of: Fe, Mn and Co.

In some cases in accordance with the present invention the nanoparticle core may have an average diameter in the range of about 0.5 nm to about 50 nm, such as about 1 nm to about 10 nm, more specifically about 1.5 nm to about 2 nm.

In accordance with the present invention said at least one peptide may comprise at least two, three, four, five or more different species of peptide. In particular, the nanoparticle may comprise insulin and GLP-1 bound to the corona of the same nanoparticle. The presence of more than one species of peptide bound to the nanoparticle may be preferred in certain settings (e.g. certain clinical settings) as compared with binding of a single species of peptide. In particular, combinations of peptides may be carried on a nanoparticle such that the peptides perform mutually beneficial functions and/or act in concert, such as in a synergistic fashion. The presence of more than one species may be used for the purpose of treating one or more conditions and for one or more therapeutic indications.

The nanoparticle of the invention may comprise a component having a divalent state, such as a metal or compound having a divalent state, or an oxide or salt thereof. For example, metals or metal complexes having the ability to exist in a divalent state are particularly useful. Such a component may be in the divalent state as added or may be transformed into a divalent state after addition. Oxides and salts of the divalent component are also useful and may be added directly or formed in situ subsequent to addition. Among the useful salts of the divalent component include halide salts, such as chloride, iodide, bromide and fluoride. Such divalent components may include, for example, divalent metals such as zinc, magnesium, copper, nickel, cobalt, cadmium, or calcium, and their oxides and salts thereof. The component is desirably present in an amount sufficient to produce a stabilizing effect, and is desirably present in an amount of about 0.5 to 2.0 equivalents to the core metal (i.e., gold), or optionally about 0.75 to 1.5 equivalents to the core metal (i.e., gold).

The divalent component may in some cases be present in the corona of the nanoparticle. It is specifically contemplated herein that the divalent component may be included in the nanoparticle, including in the corona of the nanoparticle as a result of inclusion of zinc in the process of synthesis of the nanoparticle. Additionally or alternatively, the divalent component may be added after synthesis of the nanoparticle. In some cases in accordance with the present invention, the divalent component, such as zinc may be selected from: $Zn^{2+}$ and ZnO. For example, the zinc may be in the form of $ZnCl_2$.

Preparing a Film Delivery System

The Delivery system of the present invention may be a film as defined herein. As discussed herein, a flowable film-forming matrix is prepared to be uniform in content in accordance with the teachings of the present invention. Uniformity of content is desirably maintained as the flowable matrix is formed into a film and dried. The drying process of the present invention may use several factors to produce uniformity within the film, while maintaining the active component at a safe temperature, i.e., at temperatures and/or conditions where the active won't substantially degrade, or become less potent or substantially inactive. First, the films of the present invention have an extremely short heat history, usually only on the order of minutes, so that total temperature exposure is minimized to the extent possible. The films are controllably dried to prevent aggregation and migration of components, as well as preventing heat build up within. The films may be dried from the bottom or a combination of top and bottom drying. Desirably, the top surface of the wet film is not dried in a manner which causes skinning prior to drying the thickness of the film to the desired final water content level, which as will be described later herein, is about 10% by weight or less of the total film composition.

In any drying method, however, it is desirable to rapidly form an active-immobilizing visco-elastic mass of the film within the first ten (10) minutes to fifteen (15) minutes of drying, more desirably within the first four (4) to six (6) minutes of drying and most desirably within the first four (4) minutes of drying to create a uniform distribution of said active by locking-in or substantially preventing migration of said active. For example, the active may be a component of the plurality of nano-particles referred to herein. Due to the short heat exposure and evaporative cooling, the film components such as drug, sensitive biologicals or volatile actives remain unaffected by high temperatures during the drying process, and small-scale particles of active agent are maintained in a non-aggregated fashion. In contrast, skinning on the top surface traps liquid carrier molecules of increased energy within the film, thereby causing the temperature within the film to rise and exposing active components to high, potentially deleterious temperatures.

Second, thermal mixing occurs within the film due to controlled drying and absence of surface skinning. Thermal mixing occurs via convection currents in the film. As heat is applied to the bottom of the film, the liquid near the bottom increases in temperature, expands, and becomes less dense. As such, this hotter liquid rises and cooler liquid takes its place. While rising, the hotter liquid mixes with the cooler liquid and shares thermal energy with it, i.e., transfers heat. As the cycle repeats, thermal energy is spread throughout the film.

Robust thermal mixing achieved by the controlled drying process of the present invention produces uniform heat diffusion throughout the film. In the absence of such thermal mixing, "hot spots" may develop. Pockets of heat in the film result in the formation of particle aggregates or danger areas within the film and subsequent non-uniformity. The formation of such aggregates or agglomerations is undesirable because it leads to non-uniform films in which the active may be randomly distributed. Such uneven distribution may lead to large differences in the amount of active per film unit, dosage or volume, which is problematic from a potency, safety and efficacy perspective.

Furthermore, thermal mixing helps to maintain a lower overall temperature inside the film. Although the film surfaces may be exposed to a temperature above that at which the active component degrades, the film interior may not reach this temperature. Due to this temperature differential, the active does not degrade.

For instance, the films of the present invention desirably are dried for ten (10) minutes or less. Drying the films at 80° C. for ten (10) minutes produces a temperature differential between the atmosphere and the film matrix of about 5° C. This means that after ten (10) minutes of drying, the temperature of the inside of the film is 5° C. less than the outside exposure temperature. In many cases, however, drying times of less than ten (10) minutes are sufficient, such as four (4) to six (6) minutes. Drying for four (4) minutes may be accompanied by a temperature differential of about 30° C., and drying for six (6) minutes may be accompanied by a differential of about 25° C. Due to such large temperature differentials, the films may be dried at efficient, high air temperatures without causing heat sensitive actives to degrade, and without causing the matrix to reach a temperature where the active becomes substantially unstable, substantially degrades or becomes less active.

After mechanical mixing, the film may be placed on a conveyor for continued thermal mixing during the drying process. At the outset of the drying process, the film preferably is heated from the bottom as it travels via conveyor. Heat may be supplied to the film by a heating mechanism, such as, but not limited to, a dryer. As the film is heated, the liquid carrier, or volatile, begins to evaporate. Thermal mixing also initiates as hotter liquid rises and cooler liquid takes its place. Because no skin forms on the top surface of the film, the volatile liquid continues to evaporate and thermal mixing continues to distribute thermal energy throughout the film.

Once a sufficient amount of the volatile liquid has evaporated, thermal mixing has produced uniform heat diffusion throughout the film. The components desirably are locked into a uniform distribution throughout the film. It may be desired to form a visco-elastic solid rapidly, for example within the first ten (10) minutes or less, desirably within the first six (6) minutes or less, and most desirably within the first 0.5 minutes to four (4) minutes. Although minor amounts of liquid carrier, i.e., water, may remain subsequent to formation of the visco-elastic film, the film may be dried further without affecting the desired heterogeneity of the film, if desired. Further drying forms the final film, by desirably removing solvent from the visco-elastic solid such that less than ten percent (10%) of solvent remains, and more desirably less than eight percent (8%) of solvent remains, and most desirably less than six percent (6%) of the solvent remains in the final film.

While the air temperatures for drying may be about 50° C. to about 160° C., the temperatures of the film matrix are generally less than the boiling temperature of the water in the matrix, desirably about 90° C. or less, and most desirably about 80° C. or less. In other words, the air temperatures used for drying may optionally be greater than the actual temperatures which the matrix experience.

Furthermore, active-containing particles or particulates, for example, the nanoparticles referred to herein, may be added to the film-forming composition or material after the composition or material is cast into a film. For example, such particles may be added to the film prior to the drying of the film. Active-containing particles may be controllably metered to the film and disposed onto the film through a suitable technique, such as through the use of a doctor blade, which is a device which marginally or softly touches the surface of the film and controllably disposes the particles onto the film surface. Other suitable, but non-limiting, techniques include the use of an additional roller to place the active-containing particles on the film surface, spraying or depositing the particles onto the film surface, adding the active-containing particles by either simple (applied to dry backing film) or dual slot die extrusion (backing film and particles formed simultaneously) and the like. The active-containing particles may be placed on either or both of the opposed film surfaces, i.e., the top and/or bottom film surfaces by deposition techniques. Deposition techniques would include the ability to accurately meter the amount of active-containing particles onto the surface of the film. In some embodiments, the active-containing particles may be dispersed in a fluid medium and the dispersion deposited on the film, such as in a coating layer. Desirably, the particles are securably disposed onto the film, such as being embedded into the film. Moreover, such particles are desirably not fully encased or fully embedded into the film, but remain exposed to the surface of the film, such as in the case where the particles are partially embedded or partially encased.

Monitoring and control of the thickness of the film also contributes to the production of a uniform film by providing a film of uniform thickness. The thickness of the film may be monitored with gauges such as Gamma or Beta Gauges. A gauge may be coupled to another gauge at the end of the drying apparatus, i.e. drying oven or tunnel, to communicate through feedback loops to control and adjust the opening in the coating apparatus, resulting in control of uniform film thickness. Alternatively, the thickness of the film can also be controlled by manual measurement during the production process to achieve the desired thickness of the film.

The film products are generally formed by combining a properly selected polymer and polar solvent, as well as any agent or filler as desired. Desirably, the solvent content of the combination is at least about 30% by weight of the total combination. The material formed by this combination is formed into a film, desirably by roll coating, and then dried, desirably by a rapid and controlled drying process to maintain the uniformity of the film, more specifically, a non-self-aggregating uniform heterogeneity. The resulting film will desirably contain about ten percent (10%) by weight or less solvent, more desirably about eight percent (8%) by weight or less solvent, even more desirably about six percent (6%) by weight or less solvent and most desirably about two percent (2%) or less solvent. The solvent may be water, a polar organic solvent including, but not limited to, ethanol, isopropanol, acetone, methylene chloride, or any combination thereof.

Consideration of the above discussed parameters, such as, but not limited to, rheology properties, viscosity, mixing method, casting method and drying method, also impact material selection for the different components of the present invention. Furthermore, such consideration with proper material selection provides the compositions of the present invention, including a pharmaceutical, biological, bioeffecting and/or cosmetic dosage form or film product having no more than a ten percent (10%) by weight variance of an active, e.g. a pharmaceutical, biological, bioeffecting and/or cosmetic active per unit volume, or no more of than a ten percent (10%) variance by weight of an active-carrying component (e.g. nanoparticles) per unit volume of the film product. In other words, the uniformity of the present invention is determined by the presence of no more than a ten percent (10%) by weight of the pharmaceutical, biological, bioeffecting, active-containing component and/or cosmetic variance throughout the matrix. Desirably, the variance is less than five percent (5%) by weight, less than two percent (2%) by weight, less than one percent (1%) by weight, or less than 0.5% by weight. In some embodiments, the film or film delivery system may be divided into individual films of approximately equal size, and the amount of nanoparticles (by weight) does not vary by more than about ten percent between individual films. Desirably, the variance between individual films divided from the same starting film is less than five percent (5%) by weight, less than two percent (2%) by weight, less than one percent (1%) by weight, or less than 0.5% by weight.

Film-Forming Polymers for the Film Delivery System

The film units or dosages of the present invention include at least one water soluble polymer. The films may also include water swellable or water insoluble polymers, if desired.

In some embodiments, the self-supporting film includes a saccharide-based polymer, which is water soluble. For example, the saccharide-based polymer may be cellulose or a cellulose derivative. Specific examples of useful saccharide-based, water soluble polymers include, but are not limited to, polydextrose, pullulan, hydroxypropylmethyl cellulose (HPMC), hydroxyethyl cellulose (HPC), hydroxypropyl cellulose, carboxymethyl cellulose, sodium aginate, xanthan gum, tragancanth gum, guar gum, acacia gum, arabic gum, starch, gelatin, and combinations thereof.

In some preferred embodiments, the saccharide-based polymer may be at least one cellulosic polymer, polydextrose, or combinations thereof. The film may also include non-saccharide-based, water soluble or water insoluble polymers. Examples of non-saccharide based, water soluble polymers include polyethylene oxide, polyvinylpyrrolidone, polyvinyl alcohol, polyethylene glycol, polyacrylic acid, methylmethacrylate copolymer, carboxyvinyl copolymers, and combinations thereof. Specific examples of useful water insoluble polymers include, but are not limited to, ethyl cellulose, hydroxypropyl ethyl cellulose, cellulose acetate phthalate, hydroxypropyl methyl cellulose phthalate and combinations thereof.

In some further preferred embodiments, the polymer may be a combination of hydroxypropylmethyl cellulose and polyethylene oxide. In some other preferred embodiments, the polymer is a combination of polydextrose and polyethylene oxide. In still further preferred embodiments, the polymer is a combination of polydextrose, hydroxy propylmethyl cellulose and polyethylene oxide.

As used herein, the phrase "water soluble polymer" and variants thereof refer to a polymer that is at least partially soluble in water, and desirably fully or predominantly soluble in water, or absorbs water. In some embodiments, the film unit of the present invention is at least partially dissolvable when exposed to a wetting agent. In some other embodiments, the inventive film unit is substantially dissolvable when exposed to a wetting agent.

Polymers that absorb water are often referred to as being water swellable polymers. The materials useful with the present invention may be water soluble or water swellable at room temperature and other temperatures, such as temperatures exceeding room temperature. Moreover, the materials may be water soluble or water swellable at pressures less than atmospheric pressure. Desirably, the water soluble polymers are water soluble or water swellable having at least 20 percent by weight water uptake. Water swellable polymers having a twenty-five (25) or greater percent by weight water uptake are also useful. Films or dosage forms of the present invention formed from such water soluble polymers are desirably sufficiently water soluble to be dissolvable upon contact with bodily fluids.

Other polymers useful for incorporation into the films of the present invention include biodegradable polymers, copolymers, block polymers and combinations thereof. Among the known useful polymers or polymer classes which meet the above criteria are: poly(glycolic acid) (PGA), poly (lactic acid) (PLA), polydioxanoes, polyoxalates, poly($\alpha$-esters), polyanhydrides, polyacetates, polycaprolactones, poly(orthoesters), polyamino acids, polyaminocarbonates, polyurethanes, polycarbonates, polyamides, poly(alkyl cyanoacrylates), and mixtures and copolymers thereof. Additional useful polymers include, stereopolymers of L- and D-lactic acid, copolymers of bis(p-carboxyphenoxy) propane acid and sebacic acid, sebacic acid copolymers, copolymers of caprolactone, poly(lactic acid)/poly(glycolic acid)/polyethyleneglycol copolymers, copolymers of polyurethane and (poly(lactic acid), copolymers of polyurethane and poly(lactic acid), copolymers of $\alpha$-amino acids, copolymers of $\alpha$-amino acids and caproic acid, copolymers of $\alpha$-benzyl glutamate and polyethylene glycol, copolymers of succinate and poly(glycols), polyphosphazene, polyhydroxy-alkanoates and mixtures thereof. Binary and ternary systems are contemplated.

Other specific polymers useful include those marketed under the Medisorb and Biodel trademarks. The Medisorb materials are marketed by the Dupont Company of Wilmington, Del. and are generically identified as a "lactide/glycolide co-polymer" containing "propanoic acid, 2-hydroxy-polymer with hydroxy-polymer with hydroxyacetic acid." Four such polymers include lactide/glycolide 100 L, believed to be 100% lactide having a melting point within the range of 338°-347° F. (170°-175° C.); lactide/glycolide 100 L, believed to be 100% glycolide having a melting point within the range of 437°-455° F. (225°-235° C.); lactide/glycolide 85/15, believed to be 85% lactide and 15% glycolide with a melting point within the range of 338°-347° F. (170°-175° C.); and lactide/glycolide 50/50, believed to be a copolymer of 50% lactide and 50% glycolide with a melting point within the range of 338°-347° F. (170°-175° C.).

The Biodel materials represent a family of various polyanhydrides which differ chemically.

Although a variety of different polymers may be used, it is desired to select polymers to provide a desired viscosity of the mixture prior to drying. For example, if the agent or other components are not soluble in the selected solvent, a polymer that will provide a greater viscosity is desired to assist in maintaining uniformity. On the other hand, if the components are soluble in the solvent, a polymer that provides a lower viscosity may be preferred.

The polymer plays an important role in affecting the viscosity of the film. Viscosity is one property of a liquid that controls the stability of the agent in an emulsion, a colloid or a suspension. Generally the viscosity of the matrix will vary from about 400 cps to about 100,000 cps, preferably from about 800 cps to about 60,000 cps, and most preferably from about 1,000 cps to about 40,000 cps. Desirably, the viscosity of the film-forming matrix will rapidly increase upon initiation of the drying process.

The viscosity may be adjusted based on the selected agent component and/or active-containing component, depending on the other components within the matrix. For example, if the component is not soluble within the selected solvent, a proper viscosity may be selected to prevent the component from settling which would adversely affect the uniformity of the resulting film. The viscosity may be adjusted in different ways. To increase viscosity of the film matrix, the polymer may be chosen of a higher molecular weight or crosslinkers may be added, such as salts of calcium, sodium and potassium. The viscosity may also be adjusted by adjusting the temperature or by adding a viscosity increasing component. Components that will increase the viscosity or stabilize the emulsion/suspension include higher molecular weight polymers and polysaccharides and gums, which include without limitation, alginate, carrageenan, hydroxypropyl methyl cellulose, locust bean gum, guar gum, xanthan gum, dextran, gum arabic, gellan gum and combinations thereof.

It has also been observed that certain polymers which when used alone would ordinarily require a plasticizer to achieve a flexible film, can be combined without a plasticizer and yet achieve flexible films. For example, HPMC and HPC when used in combination provide a flexible, strong film with the appropriate plasticity and elasticity for manufacturing and storage. No additional plasticizer or polyalcohol is needed for flexibility.

Additionally, polyethylene oxide (PEO), when used alone or in combination with a hydrophilic cellulosic polymer and/or polydextrose, achieves flexible, strong films. Additional plasticizers or polyalcohols are not needed for flexibility. Non-limiting examples of suitable cellulosic polymers for combination with PEO include HPC and HPMC. PEO and HPC have essentially no gelation temperature, while HPMC has a gelation temperature of 58-64° C. (Methocel EF available from Dow Chemical Co.). Moreover, these films are sufficiently flexible even when substantially free of organic solvents, which may be removed without compromising film properties. Organic solvents may tend to plasticize the film, so leaving out organic solvents may be useful when this effect is less desirable or is to be controlled by other additives. PEO based films also exhibit good resistance to tearing, little or no curling, and fast dissolution rates when the polymer component contains appropriate levels of PEO.

To achieve the desired film properties, the level and/or molecular weight of PEO in the polymer component may be varied. Modifying the PEO content affects properties such as tear resistance, dissolution rate, and adhesion tendencies. Thus, one method for controlling film properties is to modify the PEO content. For instance, in some embodiments rapid dissolving films are desirable. By modifying the content of the polymer component, the desired dissolution characteristics can be achieved.

In accordance with the present invention, PEO desirably ranges from about 20% to 100% by weight in the polymer component. In some embodiments, the amount of PEO desirably ranges from about 1 mg to about 200 mg. The hydrophilic cellulosic polymer and/or polydextrose ranges from about 0% to about 80% by weight, or in a ratio of up to about 4:1 with the PEO, and desirably in a ratio of about 1:1.

In some embodiments, it may be desirable to vary the PEO levels to promote certain film properties. To obtain films with high tear resistance and fast dissolution rates, levels of about 50% or greater of PEO in the polymer component are desirable. To achieve adhesion prevention, i.e., preventing the film from adhering to the roof of the mouth, PEO levels of about 20% to 75% are desirable. In some embodiments, however, adhesion to the roof of the mouth may be desired, such as for administration to animals or children. In such cases, higher levels of PEO may be employed. More specifically, structural integrity and dissolution of the film can be controlled such that the film can adhere to mucosa and be readily removed, or adhere more firmly and be difficult to remove, depending on the intended use.

The molecular weight of the PEO may also be varied. High molecular weight PEO, such as about 4 million, may be desired to increase mucoadhesion of the film. More desirably, the molecular weight may range from about 100,000 to 900,000, more desirably from about 100,000 to 600,000, and most desirably from about 100,000 to 300,000. In some embodiments, it may be desirable to combine high molecular weight (600,000 to 900,000) with low molecular weight (100,000 to 300,000) PEOs in the polymer component.

For instance, certain film properties, such as fast dissolution rates and high tear resistance, may be attained by combining small amounts of high molecular weight PEOs with larger amounts of lower molecular weight PEOs. Desirably, such compositions contain about 60% or greater levels of the lower molecular weight PEO in the PEO-blend polymer component.

To balance the properties of adhesion prevention, fast dissolution rate, and good tear resistance, desirable film compositions may include about 50% to 75% low molecular weight PEO, optionally combined with a small amount of a higher molecular weight PEO, with the remainder of the polymer component containing a hydrophilic cellulosic polymer (HPC or HPMC) and/or polydextrose.

In some embodiments the film may include polyvinyl alcohol (PVA), alone or in combination with at least one additional polymer Examples of an additional polymer include a cellulosic polymer, starch, polyvinyl pyrrolidone (PVP), polyethylene oxide (PEO), an alginate, a pectin, or combinations thereof. PVA can be used in the films to improve film strength and/or to vary and slow dissolution times. The films are especially useful for the delivery of cosmetics, nutraceuticals, biologics, pharmaceuticals and bioeffecting agents. In a preferred embodiment, the film includes PVA without any added plasticizers. For example, the film can include both PVA, which provides strength to the film and PEO, which provides flexibility to the film and nay obviate the need for a plasticizer.

PVA can be used in varying amounts depending upon the product application and characteristics desired. For example, in general, a larger amount of PVA will increase film strength and increase dissolution time. For films that require high active dosing, PVA can be used effectively at minimum amount of 0.5, preferably 1%, more preferably 5%, by weight of the film, to improve film strength. The PVA an be effectively used at a maximum amount, for example, 80%, preferably 50%, more preferably 25% by weight of the film. For slowing dissolution time, PVA can be used at levels as high as 80%. A film containing an active can be coated on one or both surfaces with a PVA containing layer to modify the dissolution of the film and the release of an active from the film.

High loading of actives can decrease the strength and flexibility of the film. Including PVA in the film either alone or in combination with at least one other polymer can increase the tensile strength of the film. Also, drug particles or taste-masked or coated or modified release drug particles may have a larger particle size, which can make loading of these particles into the film difficult. PVA can increase the viscosity of the film solution to allow improved drug loading.

Controlled Release Films

The term "controlled release" is intended to mean the release of the components at a pre-selected or desired rate. For example, in embodiments where the film includes nanoparticles within the body of the film, it may be desirable to control its release from the film. This rate will vary depending upon the application. Desirable rates include fast or immediate release profiles as well as delayed, sustained or sequential release. Combinations of release patterns, such as initial spiked release followed by lower levels of sustained release of active are contemplated. Pulsed releases of the agent are also contemplated.

Dissolvable films generally fall into three main classes: fast dissolving, moderate dissolving and slow dissolving. Films of the present invention are dissolvable in the presence of liquid, such as in the oral cavity of the user or when mixed with a liquid, such as water. Fast dissolving films generally dissolve in about 1 second to about 30 seconds. Moderate dissolving films generally dissolve in about 1 to about 30 minutes, and slow dissolving films generally dissolve in more than 30 minutes, e.g., up to about 60 minutes or more. Fast dissolving films may consist of low molecular weight hydrophilic polymers (i.e., polymers having a molecular weight between about 1,000 to 200,000). In contrast, slow dissolving films generally have high molecular weight polymers (i.e., having a molecular weight in the millions).

Moderate dissolving films tend to fall in between the fast and slow dissolving films. Moderate dissolving films dissolve rather quickly, and can also have a good level of mucoadhesion. Moderate films are also flexible, quickly wettable, and are typically non-irritating to the user. For oral-dissolving films, moderate dissolving films are preferred, since such films provide a quick enough dissolution rate (between about 1 minute and about 30 minutes), while providing an acceptable mucoadhesion level such that the film is not easily removable once it is placed in the oral cavity of the user.

The polymers that are chosen for the films of the present invention may also be chosen to allow for controlled disintegration of the components. This may be achieved by providing a substantially water insoluble film that incorporates nanoparticles that will be released from the film over time.

This may be accomplished by incorporating a variety of different soluble or insoluble polymers and may also include biodegradable polymers in combination. Alternatively, coated controlled release agent particles may be incorporated into a readily soluble film matrix to achieve the controlled release property of the nanoparticles. The polymers used for preparing the film matrix may be water-soluble, partially water-soluble, water swellable or a combination of polymers which may be soluble, partially soluble and/or swellable.

In some embodiments a combination of a sustained release (or slow dissolving) film layer may be combined with a layer of fast dissolving film. The active or active-containing component, such as the insulin and/or GLP-1 nanoparticles described herein, may be in either layer or both. In one embodiment, the active or active-containing component is in a fast dissolving (or fast release) film layer and a slower, sustained release layer may be laminated or otherwise attached thereto. The fast release layer may be intended to be against a mucosal or organ tissue surface as defined herein) and the slow, sustained release layer may be an exclusive layer which covers and protects the fast dissolving layer, as well as adhering the total film unit to the mucosal or organ tissue (as defined herein) site, e.g., as in a buccal application.

The convenience of administering a single dose of a medication which releases components in a controlled fashion over an extended period of time, as opposed to the administration of a number of single doses at regular intervals has long been recognized in the pharmaceutical arts. The advantage to the patient and clinician in having consistent and uniform levels of medication delivered to the body over an extended period of time are likewise recognized.

Optional Components

A variety of other components and fillers may also be added to the films of the present invention. These may include, without limitation, surfactants; plasticizers which assist in compatibilizing the components within the mixture; polyalcohols; anti-foaming agents, such as silicone-containing compounds, which promote a smoother film surface by releasing oxygen from the film; and thermo-setting gels such as pectin, carageenan, and gelatin, which help in maintaining the dispersion of components.

The variety of additives that can be incorporated into the inventive compositions may provide a variety of different functions. Examples of classes of additives include excipients, lubricants, buffering agents, stabilizers, blowing agents, pigments, coloring agents, fillers, bulking agents, fragrances, release modifiers, adjuvants, plasticizers, flow accelerators, mold release agents, polyols, granulating agents, diluents, binders, buffers, absorbents, glidants, adhesives, anti-adherents, acidulants, softeners, resins, demulcents, solvents, surfactants, emulsifiers, elastomers and mixtures thereof. These additives may be added with the active ingredient(s).

Useful additives include, for example, gelatin, vegetable proteins such as sunflower protein, soybean proteins, cotton seed proteins, peanut proteins, grape seed proteins, whey proteins, whey protein isolates, blood proteins, egg proteins, acrylated proteins, water soluble polysaccharides such as alginates, carrageenans, guar gum, agar-agar, xanthan gum, gellan gum, gum arabic and related gums (gum ghatti, gum karaya, gum tragancanth), pectin, water soluble derivatives of cellulose: alkylcelluloses hydroxyalkylcelluloses and hydroxyalkylalkylcelluloses, such as methylcelulose, hydroxymethylcellulose, hydroxyethylcellulose, hydroxypropylcellulose, hydroxyethylmethylcellulose, hydroxypropylmethylcellulose, hydroxybutylmethylcellulose, cellulose esters and hydroxyalkylcellulose esters such as cellulose acetate phthalate (CAP), hydroxypropylmethylcellulose (HPMC); carboxyalkylcelluloses, carboxyalkylalkylcelluloses, carboxyalkylcellulose esters such as carboxymethylcellulose and their alkali metal salts; water soluble synthetic polymers such as polyacrylic acids and polyacrylic acid esters, polymethacrylic acids and polymethacrylic acid esters, polyvinylacetates, polyvinylalcohols, polyvinylacetatephthalates (PVAP), polyvinylpyrrolidone (PVP), PVY/vinyl acetate copolymer, and polycrotonic acids; also suitable are phthalated gelatin, gelatin succinate, crosslinked gelatin, shellac, water soluble chemical derivatives of starch, cationically modified acrylates and methacrylates possessing, for example, a tertiary or quaternary amino group, such as the diethylaminoethyl group, which may be quaternized if desired; and other similar polymers.

Such extenders may optionally be added in any desired amount desirably within the range of up to about 80%, desirably about 3% to 50% and more desirably within the range of 3% to 20% based on the weight of all components.

Further additives may be glidants and opacifiers, such as the oxides of magnesium aluminum, silicon, titanium, etc. desirably in a concentration range of about 0.02% to about 3% by weight and desirably about 0.02% to about 1% based on the weight of all components.

Further examples of additives are plasticizers which include polyalkylene oxides, such as polyethylene glycols, polypropylene glycols, polyethylene-propylene glycols, organic plasticizers with low molecular weights, such as glycerol, glycerol monoacetate, diacetate or triacetate, triacetin, polysorbate, cetyl alcohol, propylene glycol, sorbitol, sodium diethylsulfosuccinate, triethyl citrate, tributyl citrate, and the like, added in concentrations ranging from about 0.5% to about 30%, and desirably ranging from about 0.5% to about 20% based on the weight of the polymer.

There may further be added compounds to improve the texture of the film composition such as animal or vegetable fats, desirably in their hydrogenated form, especially those which are solid at room temperature. These fats desirably have a melting point of 50° C. or higher. Preferred are triglycerides with $C_{12}$-, $C_{14}$-, $C_{16}$-, $C_{18}$-, $C_{20}$- and $C_{22}$-fatty acids. These fats can be added alone without adding extenders or plasticizers and can be advantageously added alone or together with mono- and/or di-glycerides or phosphatides, especially lecithin. The mono- and di-glycerides are desirably derived from the types of fats described above, i.e. with $C_{12}$-, $C_{14}$-, $C_{16}$-, $C_{18}$-, $C_{20}$- and $C_{22}$-fatty acids.

The total amounts used of the fats, mono-, di-glycerides and/or lecithins are up to about five percent (5%) and preferably within the range of about 0.5% to about two percent (2%) by weight of the total composition It is further useful to add silicon dioxide, calcium silicate, or titanium dioxide in a concentration of about 0.02% to about 1% by weight of the total composition. These compounds act as opacifiers and flow agents.

These additives are to be used in amounts sufficient to achieve their intended purpose. Generally, the combination of certain of these additives will alter the overall release profile of the active ingredient and can be used to modify, i.e. impede or accelerate the release.

Lecithin is one surface active agent for use in the present invention. Lecithin can be included in the feedstock in an amount of from about 0.25% to about 2.00% by weight. Other surface active agents, i.e. surfactants, include, but are not limited to, cetyl alcohol, sodium lauryl sulfate, the Spans™ and Tweens™ which are commercially available from ICI Americas, Inc. Ethoxylated oils, including ethoxylated castor oils, such as Cremophor® EL which is commercially available from BASF, are also useful. Carbowax™ is yet another modifier which is very useful in the present invention. Tweens™ or combinations of surface active agents may be used to achieve the desired hydrophilic-lipophilic balance ("HLB"). The present invention, however, does not require the use of a surfactant and films or film-forming compositions of the present invention may be essentially free of a surfactant while still providing the desirable uniformity features of the present invention.

As additional modifiers which enhance the procedure and product of the present invention are identified, Applicants intend to include all such additional modifiers within the scope of the invention claimed herein.

Other ingredients include binders which contribute to the ease of formation and general quality of the films. Non-limiting examples of binders include starches, pregelatinize starches, gelatin, polyvinylpyrrolidone, methylcellulose, sodium carboxymethylcellulose, ethylcellulose, polyacrylamides, polyvinyloxoazolidone, and polyvinylalcohols.

Films of the present invention, particularly films useful for oral ingestion by a user, may further include one or more taste-enhancing agents, such as flavors and/or sweeteners. Suitable flavors and sweeteners include those set forth in U.S. Pat. No. 7,425,292, the entire contents of which are incorporated by reference herein.

Further potential additives include solubility enhancing agents, such as substances that form inclusion compounds with active components. Such agents may be useful in improving the properties of very insoluble and/or unstable actives. In general, these substances are doughnut-shaped molecules with hydrophobic internal cavities and hydrophilic exteriors. Insoluble and/or instable actives may fit within the hydrophobic cavity, thereby producing an inclusion complex, which is soluble in water. Accordingly, the formation of the inclusion complex permits very insoluble and/or instable actives to be dissolved in water. A particularly desirable example of such agents are cyclodextrins, which are cyclic carbohydrates derived from starch. Other similar substances, however, are considered well within the scope of the present invention.

The various embodiments of the invention may include penetration and permeation enhancers. Among such useful enhancers are included medium chain mono- and diacylglycerol fatty acid derivative, such as glycerol laurate, and mixtures thereof; synthetic and natural surfactants and mixtures thereof; medium chain fatty acids and salts and esters thereof, including mono-, di- and triglycerides such as sodium caprylate and sodium caprate and mixtures thereof; bile salts; chelating agents, such as EDTA; detergents; cylodextrins, enamine derivatives, phospholipids, lecithins, cetomacrogels, sodium salicylate, sodium-5-methoxysalicyclic acid; glycerol and polyethylene glycol estess such as those sold under the name Labrasol; zonula occludens toxin; and alkyl glycosides. Additionally, combinations of penetration and permeation enhancers from different classes are also useful.

Additional permeation enhancers include, polysorbate 80, phosphatidylcholine, nmethylpiperazine, sodium salicylate, melittin, and palmitoyl carnitine chloride (pcc). 23-lauryl ether, aprotinin, azone, benzalkonium chloride, cetylpyridinium chloride, cetyltrimethylammonium bromide, cyclodextrin, dextran sulfate, lauric acid, lauric acid/propylene glycol, lysophosphatidylcholine, menthol, methoxysalicylate, methyloleate, oleic acid, phosphatidylcholine, polyoxyethylene, sodium edta, sodium glycocholate, sodium taurocholate, sodium lauryl sulfate, sodium salicylate, sodium glycodeoxycholate, sodium taurodeoxycholate, sulfoxides, and combinations thereof.

Additional permeation and/or penetration enhancers include dimethylsulfoxide, decylmethylsulfoxide, alkylsulfoxides: alkanols, such as ethanol, propanol, butanol, pentanol, hexanol, octanolnonanol, decanol, 2-butanol, 2-pentanol, benzyl alcohol; fatty alcohol acids and their corresponding alcohols, such as caprylic, decyl, lauryl, 2-lauryl, myristly, cetyl, stearyl oleyl, linoleyl, linolenyll alcohol; linear carboxylic acids such as: valeric, heptanoic, pelagonic, caproic, capric, lauric, Myristic, stearic, oleic, caprylic; Branched carboxylic acids: such as isovaleric, neopentanoic, neoheptanoic, neononanoic, trimethyl hexanoic, neodecanoic, isostearic; fatty acid esters, such as aliphatic-isopropyl n-butyrate, isopropyl n-hexanoate, isopropyl n-decanoate, isopropyl myristate, isopropyl palmitate, octyldodecyl myristate; alkyl esters such as ethyl acetate, butyl acetate, methyl acetate, methylvalerate, methylpropionate, diethyl sebacate, ethyl oleate; propylene glycol, polyethylene glycol, ethylene glycol, diethylene glycol, triethylene glycol, dipropylene glycol, glycerol, propanediol, butanediol, pentanediol, hexanetriol, urea, dimethylacetamide, diethyltoluamide, dimethylformamide, dimethyloctamide, dimethyldecamide; biodegradable cyclic urea, such as 1-alkyl-4-imidazolin-2-one; pyrrolidone derivatives, such as 1-methyl-2-pyrrolidone, 2-pyrrolidone, 1-lauryl-2-pyrrolidone, 1-methyl-4-carboxy-2-pyrrolidone, 1-hexyl-4-carboxy-2-pyrrolidone, 1-lauryl-4-carboxy-2pyrrolidone, 1-methyl1-4methoxycarbonyl-2-pyrrolidone, 1-hexyl-4-methoxycarbonyl-2pyrrolidone, 1-lauryl-4-methoxycarbonyl-2-pyrrolidone, N-cyclohexylpyrrolidone, N-dimethylaminopropylpyrrolidone, N-cocoalkypyrrolidone, N-tallowalkylpyrrolidone; biodegradable pyrrolidone derivatives such as the fatty acid esters of N-(2-hydroxyethyl)-2-pyrrolidone; cyclic amides such as 1-dodecylazacycloheptane-2-one (Azone), 1-geranylazacycloheptan-2-one, 1 farnesylazacycloheptan-2-one, 1-teranylgeranylazacycloheptan-2-one, 1-(3,7-dimethyloctyl)azacycloheptan-2-one, 1-(3,7,11-trimethyldodecyl)azacyclohaptan-2-one, 1-geranylazacyclohexane-2-one, 1-geranylazacyclopentan-2.5-dione, 1-farnesylazacyclopentan-2-one; hexamethylenelauramide and its derivatives; diethanolamine, triethanolamine; anionic surfactants such as sodium laurate, sodium lauryl sulphate; cationic surfactants such as cetyltrimethyl ammonium bromide, tetradecyltrimethylammonium bromide, benzalkonium chloride, octadecyltrimethylammonium chloride, cetylpyridinium chloride, dodecyltrimethylammonium chloride, hexadecyltrimethylammonium chloride; nonionic surfactants including block copolymers of polyoxyethylene/polyoxypropylene/polyoxyethylene (such as those sold under the tradenames Poloxamer 231, 182, and 184), polyoxyethylene dodecyl ethers (sold under the tradename Brij 30_), polyoxyethylene monooleyl ethers (sold under the tradenames Brij 93, 96 and 99), sorbitan fatty acid esters such as those sold under the tradenames Span (20, 40, 60, 80, 85), sorbitan monosterates such as those sold under the tradenames Tween (20, 40, 60, 80), polyethylene glycol monosterates such as those sold under the tradenames Myrj (45, 51, 52), and propylene glycol dicaprylate/dicaprate sold under the tradenames Miglyol 840 and others; bile salts such as sodium cholate, sodium salts of taurocholic, glycholic and desoxycholic acids; lecithin; hydrocarbons such as D-Limonene, a-pinene, B-carene; alcohols such as a-terpineol, terpinen-4-ol, carvol; ketones such as carvone, pulegonee, piperitone, menthone; oxides such as cyclohexene ocide, limonene oxide, a-pinene oxice, cyclopentene oxide, 1,8-cineole; oils such as Ylang ylang, anise, chenopodium, eucalyptus; N-heptane, N-octane, N-nonane, N-decane, N-undecane, N-dodecane, N-tridecane, N-tetradecane, N-hexadecane; salicylic acid and salicylates (including their methyl, ethyl, and propyl glycol derivatives); citric and succinic acid.

As previously stated, combinations of penetration and permeation enhancers from different classes are also useful.

Combinations of alcohols and other permeation enhancers are useful. For example ethanol and isopropanol may be used as a combination. These alcohols may further be used in combination with other permeation and/or penetration enhancers described herein as mixtures or solutions. For example, non-limitin useful combinations include ethanol in combination with one or more components selected from cyclic monoterpenes, propylene glycol dicaprylate/decaprate (sold under the tradename Miglyol 840), Ethyl acetate, oleic acid, 1-menthol, urea, glycerides, triesters of glycerin and aliphatic acids such as tricaprylin (sold under the tradename Panasate 800), propylene glycol, urea, water: and isopropanol in combination with components such as polyoxyethylene sorbitan monooleate (sold under the tradename Tween 80), isopropyl myristate, isopropyl myristate, lauric acid, lauryl alcohol and Na lauryl sulphate.

The permeation enhancers promote and/or enhance the absorption of the active. Enzyme inhibitors may also be employed to protect sensitive biological active agents from being destroyed prior to absorption. The permeation enhancers may be used in various effective amounts in the film depending upon the specific formulation and active. Generally, permeation enhancers may be present in amounts of about 15% to about 25%, used more desirably in amounts of 0.01% to about 15%, by weight of the total film composition.

Forming the Film

The films of the present invention may be formed into a film strip or a sheet prior to drying. After the desired components are combined to form a multi-component matrix, including the polymer, water, and nanoparticles, as well as any other component as desired, the combination is formed into a sheet or film, by any method known in the art such as coating, spreading, casting or drawing the multi-component matrix. If a multi-layered film is desired, this may be accomplished by co-extruding more than one combination of components which may be of the same or different composition. A multi-layered film may also be achieved by coating, spreading, or casting a combination onto an already formed film layer.

A number of techniques may be employed in the mixing stage to prevent bubble inclusions in the final film. To provide a composition mixture with substantially no air bubble formation in the final product, anti-foaming or surface-tension reducing agents are employed. Additionally, the speed of the mixture is desirably controlled to prevent cavitation of the mixture in a manner which pulls air into the mix. Finally, air bubble reduction can further be achieved by allowing the mix to stand for a sufficient time for bubbles to escape prior to drying the film. Desirably, the inventive process first forms a masterbatch of film-forming components without active ingredients or volatile materials. In one embodiment, the active(s) are combined with smaller mixes of the masterbatch just prior to casting. Thus, the masterbatch pre-mix can be allowed to stand for a longer time without concern for instability of the active agent or other ingredients.

Although a variety of different film-forming techniques may be used, it is desirable to select a method that will provide a flexible film, such as reverse roll coating. The flexibility of the film allows for the sheets of film to be rolled and transported for storage or prior to being cut into individual dosage forms. Desirably, the films will also be self-supporting or, in other words, able to maintain their integrity and structure in the absence of a separate support. Furthermore, the films of the present invention may be selected of materials that are edible or ingestible.

Casting or Depositing the Film Composition

The invention uses processes for making self-supporting films having a substantially uniform distribution of components. The self supporting film is particularly useful for delivery of actives as discussed herein. The processes for making the film are designed to maintain the compositional uniformity of components distributed throughout the film, which is particularly necessary when actives, such as pharmaceutical actives, are incorporated into the film. In the pharmaceutical context, it is essential that the film is compositionally uniform so that it can be divided into individual film dosage units, each dosage unit having the appropriate amount of active when administered, such that regulatory approval can be secured.

The process may further include the preliminary steps of forming a masterbatch premix of an edible water-soluble polymer and water; optionally deaerating the premix (such as by mixing); feeding a predetermining amount of the premix to at least one mixer; adding the nanoparticles to the mixer; and mixing the components to achieve a uniform distribution thereof. Thereafter, the wet film is formed and dried.

Coating or casting methods are particularly useful for the purpose of forming the films of the present invention. Specific examples include reverse roll coating, gravure coating, immersion or dip coating, metering rod or meyer bar coating, slot die or extrusion coating, gap or knife over roll coating, air knife coating, curtain coating, or combinations thereof, especially when a multi-layered film is desired.

Roll coating, or more specifically reverse roll coating, is particularly desired when forming films in accordance with the present invention. This procedure provides excellent control and uniformity of the resulting films, which is desired in the present invention. In this procedure, the coating material is measured onto the applicator roller by the precision setting of the gap between the upper metering roller and the application roller below it. The coating is transferred from the application roller to the substrate as it passes around the support roller adjacent to the application roller. Both three roll and four roll processes are common.

The gravure coating process relies on an engraved roller running in a coating bath, which fills the engraved dots or lines of the roller with the coating material. The excess coating on the roller is wiped off by a doctor blade and the coating is then deposited onto the substrate as it passes between the engraved roller and a pressure roller.

Offset Gravure is common, where the coating is deposited on an intermediate roller before transfer to the substrate.

In the simple process of immersion or dip coating, the substrate is dipped into a bath of the coating, which is normally of a low viscosity to enable the coating to run back into the bath as the substrate emerges.

In the metering rod coating process, an excess of the coating is deposited onto the substrate as it passes over the bath roller. The wire-wound metering rod, sometimes known as a Meyer Bar, allows the desired quantity of the coating to remain on the substrate. The quantity is determined by the diameter of the wire used on the rod.

In the slot die process, the coating is squeezed out by gravity or under pressure through a slot and onto the substrate. If the coating is 100% solids, the process is termed "Extrusion" and in this case, the line speed is frequently much faster than the speed of the extrusion. This enables coatings to be considerably thinner than the width of the slot.

The gap or knife over roll process relies on a coating being applied to the substrate which then passes through a "gap" between a "knife" and a support roller. As the coating and substrate pass through, the excess is scraped off.

Air knife coating is where the coating is applied to the substrate and the excess is "blown off" by a powerful jet from the air knife. This procedure is useful for aqueous coatings.

In the curtain coating process, a bath with a slot in the base allows a continuous curtain of the coating to fall into the gap between two conveyors. The object to be coated is passed along the conveyor at a controlled speed and so receives the coating on its upper face. In some embodiments, the active-containing particles may be deposited by a micro-drop deposition technique onto a discrete unit dose of the film. In some embodiments the active-containing component or particles may be printed onto the surface of a film already formed, to form a discrete printed layer of active thereon.

Drying the Film

The drying step also be a contributing factor with regard to maintaining the uniformity of the film composition. A controlled drying process is particularly important when, in the absence of a viscosity increasing composition or a composition in which the viscosity is controlled, for example by the selection of the polymer, the components within the film may have an increased tendency to aggregate or conglomerate.

An alternative method of forming a film with an accurate dosage, that would not necessitate the controlled drying process, would be to cast the films on a predetermined well. With this method, although the components may aggregate, this will not result in the migration of the active to an adjacent dosage form, since each well may define the dosage unit per se.

One process used to make the films is described in U.S. Pat. No. 7,425,292, which is incorporated in its entirety herein by reference. In this process, the films are prepared by rapidly forming a visco-elastic film by applying hot air currents to the film to prevent flow migration and intermolecular forces from creating aggregates or conglomerates thereby maintaining compositional uniform distribution of components in the film; and further drying the visco-elastic film to form a self-supporting film.

The wet film forming matrix first may be fed onto the top side of a surface prior to the application of hot air currents. The wet film is desirably formed from a deaerated matrix within a time period before the active contained therein degrades. The process may further include a step of dividing the dried film into individual dosage units of equal dimensions and compositional make-up. There may be hot air currents applied to the top surface, if desired. In such embodiments, it may be desired that hot air currents be applied to the bottom surface of the film at a higher velocity than to the top surface of the film during drying. Hot air currents applied to dry the top of the films are preferably less than that which would cause surface rippling or skinning. The air current velocity is controlled such that it does not supply a sheer stress sufficient to overcome the inherent viscosity of the film forming matrix and therefore does not disturb the top surface of the film. This permits the film to sufficiently thicken in viscosity to lock-in volumetric uniformity while permitting evaporation of water through the non-skinned surface.

When a controlled or rapid drying process is used, liquid carriers are removed from the film in a manner such that the uniformity, or more specifically, the non-self-aggregating uniform heterogeneity, that is obtained in the wet film is maintained.

Desirably, the film is rapidly dried, such that a solid, visco-elastic structure is initially formed and the contents of the film are "locked in". This can take place within the first few minutes, e.g. about the first 0.5 to about 4.0 minutes of the drying process. It may be desired to limit the amount of top air flow during this initial drying stage. Controlling the drying in this manner prevents the destruction and reformation of the film's top surface, which results from conventional drying methods. This is accomplished by forming the film and placing it on the top side of a surface having top and bottom sides. Then, heat is initially applied to the bottom side of the film to provide the necessary energy to evaporate or otherwise remove the liquid carrier. The films dried in this manner dry more quickly and evenly as compared to air-dried films, or those dried by conventional drying means. In contrast to an air-dried film that dries first at the top and edges, the films dried by applying heat to the bottom dry simultaneously at the center as well as at the edges. This also prevents settling of ingredients that occurs with films dried by conventional means.

The temperature of the film forming matrix during drying is desirably about 100° C. or less, desirably about 90° C. or less, and most desirably about 80° C. or less. The air temperature may be substantially greater than the film matrix temperature provided that no substantial deleterious effects are imparted on the film matrix or the active or active-containing component or particles. It may be desired to dry the film such that the temperature within the film is less than the boiling point of any solvent or solvents that are within the film forming matrix. Further, it is desirable that the temperature within the film forming matrix is maintained below the degradation temperature of any actives contained within the film. It is noted, however, that the temperature outside of the film may be above the temperature within the film, and in some instances may be substantially higher than the temperature within the film.

Another method of controlling the drying process, which may be used alone or in combination with other controlled methods as disclosed above includes controlling and modifying the humidity within the drying apparatus where the film is being dried. In this manner, the premature drying of the top surface of the film may be avoided.

Another method of drying tracks that previously set forth by Magoon, which is based on an interesting property of water. Although water transmits energy by conduction and convection both within and to its surroundings, water only radiates energy within and to water. Therefore, the apparatus of Magoon includes a surface onto which the fruit pulp is placed that is transparent to infrared radiation. The underside of the surface is in contact with a temperature controlled water bath. The water bath temperature is desirably controlled at a temperature slightly below the boiling temperature of water. When the wet fruit pulp is placed on the surface of the apparatus, this creates a "refractance window." This means that infrared energy is permitted to radiate through the surface only to the area on the surface occupied by the fruit pulp, and only until the fruit pulp is dry. The apparatus of Magoon provides the films of the present invention with an efficient drying time reducing the instance of aggregation of the components of the film.

The objective of the drying processes described herein is to provide a method of drying the films that avoids complications, such as the noted "rippling" effect, that are associated with conventional drying methods and which initially dry the upper surface of the film, trapping moisture inside. In conventional oven drying methods, as the moisture trapped inside subsequently evaporates, the top surface is altered by being ripped open and then reformed.

These complications are avoided by the present drying methods, and a uniform film is provided by drying the bottom surface of the film first or otherwise preventing the formation of polymer film formation (skin) on the top surface of the film prior to drying the depth of the film. This may be achieved by applying heat as described above, or alternatively by the introduction of radiation (such as controlled microwaves) to evaporate the water or other polar solvent within the film. In some embodiments, the film is rapidly dried so as to form a visco-elastic structure within the first fifteen (15) minutes of drying, desirably within the first ten (10) minutes of drying, and more particularly within the first four (4) minutes of drying. Desirably, the film is dried at such a rapid rate that any components, including the nanoparticles, do not undesirably move or aggregate together. By rapidly drying the wet matrix, a substantial number of the nanoparticles do not have time to agglomerate.

Yet alternatively, drying may be achieved by using balanced fluid flow, such as balanced air flow, where the bottom and top air flows are controlled to provide a uniform film. In such a case, the air flow directed at the top of the film should not create a condition which would cause movement of particles present in the wet film, due to forces generated by the air currents, that is, any top air flow that is present during this drying stage should be insufficient to overcome the inherent viscosity of the film surface. Additionally, any air currents directed at the bottom of the film should desirably be controlled such that the film does not lift up due to forces from the air. Uncontrolled air currents, either above or below the film, can create non-uniformity in the final film products. The humidity level of the area surrounding the top surface may also be appropriately adjusted to prevent premature closure or skinning of the polymer surface.

The present invention yields exceptionally uniform film products when attention is paid to reducing the movement and/or aggregation of the compositional components. By avoiding the introduction of and eliminating excessive air in the mixing process, selecting polymers and solvents to provide a controllable viscosity and by controllably drying the film in a rapid manner to maintain uniformity by locking-in the active-containing components, such films result. Various drying methods include those set forth in U.S. Pat. Nos. 7,425,292 and 7,357,891, which are herein incorporated by reference in their entireties.

The films may initially have a thickness of about 500 μm to about 1,500 μm, or about 20 mils to about 60 mils, and when dried have a thickness from about 3 μm to about 250 μm, or about 0.1 mils to about 10 mils. In some embodiments, the film product has a thickness of greater than 0.1 mils. In some other embodiments, the film product has a thickness of about 10 mils or fewer. In some further embodiments, the film product has a thickness of about 0.5 mils to about 5 mils. Desirably, the dried films will have a thickness of about 2 mils to about 8 mils, and more desirably, from about 3 mils to about 6 mils.

Extruding the Film Composition

In alternative embodiments, the film products of the present invention may be formed by extrusion rather than casting or deposition methods. Extrusion is particularly useful for film compositions containing polyethylene oxide-based polymer components, as discussed below. For instance, a single screw extrusion process may be employed in accordance with the present invention. According to such an extrusion process, pressure builds in the polymer melt so that it may be extruded through a die or injected into a mold.

It may be particularly desirable to employ extrusion methods for forming film compositions containing PEO polymer components. These compositions contain PEO or PEO blends in the polymer component, and may be essentially free of added plasticizers, and/or surfactants, and polyalcohols.

The compositions may be extruded as a sheet at processing temperatures of less than about 90° C. Extrusion may proceed by squeezing the film composition through rollers or a die to obtain a uniform matrix. The extruded film composition then is cooled by any mechanism known to those of ordinary skill in the art. For example, chill rollers, air cooling beds, or water cooling beds may be employed. The cooling step is particularly desirable for film compositions containing PEO polymer components because PEO tends to hold heat. The thus formed sheets can be formed into various shapes, as desired.

Uses of Films

The films of the present invention are well suited for many uses. The high degree of uniformity of the components of the film makes them particularly well suited for incorporating pharmaceuticals. Furthermore, the polymers used in construction of the films may be chosen to allow for a range of disintegration times for the films. A variation or extension in the time over which a film will disintegrate may achieve control over the rate that the active is released, which may allow for a sustained release delivery system. In addition, the films may be used for the administration of nanoparticles to skin and other body surfaces, including those with mucous membranes and organ tissue (as defined herein).

The films may be used to administer nanoparticles through oral, or any other administration desired. Administration may be accomplished by preparing the film as described above, introducing the film to a mucosal or tissue surface of a mammal, and wetting the film if necessary, for example. If desired, this film may be prepared and adhered to a second or support layer from which it is removed prior to use, i.e. application to the skin. An adhesive may be used to attach the film to the support or backing material, which may be any of those known in the art, and is preferably not water soluble. If an adhesive is used, it will desirably be an adhesive that does not alter the properties of the active. Mucoadhesive compositions are also useful. The film compositions in many cases serve as mucoadhesives themselves.

The films of the present invention take advantage of the films' tendency to dissolve quickly when wetted, i.e., through contact with a wetting agent such as water or saliva. The nanoparticles may be introduced to a liquid by preparing a film in accordance with the present invention, introducing it to a liquid, and allowing the film to dissolve. This may be used to prepare a liquid dosage form of the nanoparticles, which may then be administered to the user.

The following is presented by way of example and is not to be construed as a limitation to the scope of the claims.

EXAMPLES

Example 1

Preparation of Ligands

Preparation of 2-thio-ethyl-α-D-galactoside (α-galactose C2SH)

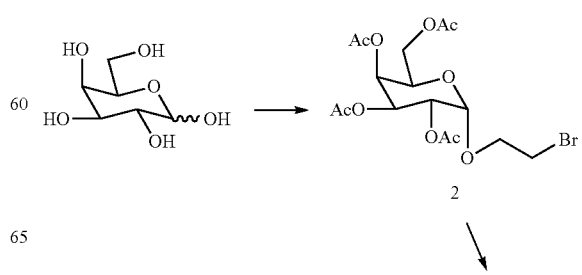

-continued

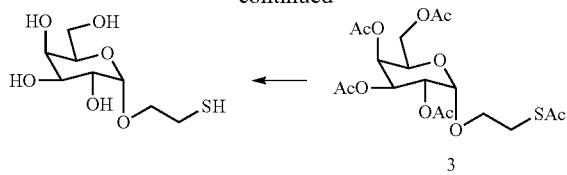

To a suspension of galactose (3 g, 16.65 mmol) in 2-bromoethanol (30 ml), acid resin Amberlite 120-H is added to reach pH 2. The reaction is stirred for 16 hours at 50-60° C. The reaction mixture is filtered and washed with MeOH. Triethylamine is added to reach pH 8. The crude of the reaction is concentrated and co evaporated 3 times with toluene. The reaction mixture is dissolved pyridine (75 mL) and Ac2O (35 mL) and a catalytic amount of DMAP are added at 0° C. and stirred for 3 h at rt. The mixture is diluted with AcOEt and washed with 1. $H_2O$; 2. HCl (10%) 3. $NaHCO_3$ dis 4. $H_2O$. The organic layer is collected and dried over anhydrous $Na_2SO_4$. TLC (Hexane:AcOEt 3:1, 2 elutions) shows a major product (desired) and a lower Rf minority. The product is purified by flash chromatography using the mixture hexane:ethyl acetate 6:1 as eluyent and the 2-bromoethyl-alpha-galactoside (2) is obtained.

The product of the previous reaction, 2 is dissolved in 27 ml of 2-butanone. To this solution, a catalytic amount of tetrabutylammonium iodide and 4 equivalents of potassium thioacetate are added. The resulting suspension is stirred for 2 hours at room temperature. Throughout this period the reaction is tested by TLC (hexane-AcOEt 2:1, 2 elutions) for the disappearance of the starting material. The mixture is diluted with 20 ml of AcOEt and washed with a saturated NaCl solution. The organic phase is dried, filtered and evaporated under vacuum. The product is purified in hexane/AcOEt 2:1→1:1 to obtain the acetylthio-alpha-galactoside 3.

The new product of the reaction, 3 is dissolved in a mixture dichloromethane-methanol 2:1. To this mixture a solution of 1N sodium methoxide (1 equivalent) is added and stirred for 1 hour at room temperature. Amberlite IR-120H resin is added to achieve pH 5-6. The resulting mixture is then filtered and concentrated to dryness to obtain the final product (α-galactose C2SH).

Preparation of Amino-Thiol Linker

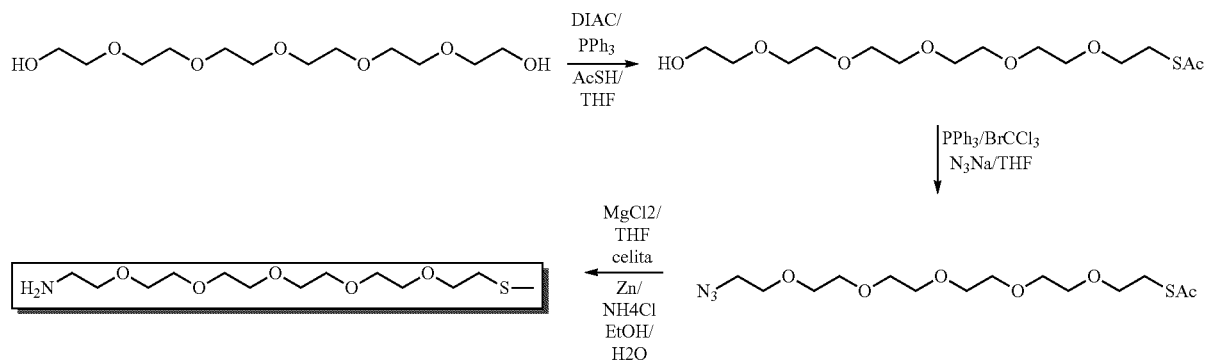

To a solution of $PPh_3$ (3 g, 11.4 mmol) in 20 ml dry THF, DIAC (2.3 g, 11.4 mmol) is added. The mixture is allowed to stir at 0° C. 15 min until the appearance of a white product. To this mixture a solution of hexaethyleneglycol (1.45 mL, 5.7 mmol) and HSAc (610 μl, 8.55 mmol) in dry THF (20 mL) is added dropwise (addition funnel). After 15 min the products begin to appear on TLC at Rf 0.2. The solution is concentrated in an evaporator. The crude of the reaction is dissolved in 50 ml of dichloromethane and washed with a solution of $K_2CO_3$ 10%. The organic phase is dried over anhydrous $Na_2SO_4$, filtered and concentrated under vacuum. Flash chromatography of the crude using AcOEt:Hexane 1:1, AcOEt and finally DCM:MeOH 4:1 as eluyent gave the acetyl-thio-hexaethyleneglycol derivative.

The reaction product is dissolved in 5 ml of DMF and $PPh_3$ (2.25 g, 8.55 mmol), $NaN_3$ (0.741 g, 11.4 mmol) and $BrCl_3C$ (0.845 ml, 8.55 mmol) are added and the solution subsequently stirred for 40 min at room temperature. The resulting product has a higher Rf than the starting product when performing TLC (DCM:MeOH 25:1). The reaction mixture is diluted with 100 ml of diethylether and washed three times with $H_2O$. The organic phase is dried over anhydrous $Na_2SO_4$, filtered and evaporated under vacuum. The product is purified by flash chromatography using the mixture of eluyents DMC/MeOH 200:1 and DCM/MeOH 40:1 to obtain the azido-acetylthio-hexaethyleneglycol derivative.

To remove the triphenyl phosphine oxide, the reaction product is dissolved in 10 ml of THF and 0.5 g of $MgCl_2$ is added to this solution. The reaction is stirred for 2 h at 80° C. until a white precipitate appears and then is filtered through celite. The product is dissolved in a mixture of ethanol:$H_2O$ 3:1 and added Zn dust (0.45 g, 6.84 mmol) and $NH_4Cl$ (0.6 g, 11.4 mmol). The reaction was stirred at reflux for 1 h until the presence of starting material is no longer detectable by TLC (DCM/MeOH 25:1). The reaction is filtered through celite and the solvent is evaporated. The crude de reaction is diluted with AcOEt and extract with 5 ml $H_2O$. The aqueous phase is evaporated to dryness to obtain the amino-thiol-hexaethylenglycol product.

Example 2

Preparation of Mixed Gold Nanoparticles

Beta-glucose C2 derivative 1, N-acetylglucosamine C2 derivative 2, alpha-galactose C2 derivative 3, alpha-glucose C2 derivative 4, glucosamine C5 derivative 5 and hexaethyleneglycol amine linker 6 were taken from Midatech Biogune stock. N-(3-Dimethylaminopropyl)-N'-ethylcarbodiimide hydrochloride (EDC.HCl), $HAuCl_4$, $NaBH_4$ were purchased from Sigma-Aldrich Chemical Company. Imidazole-4-acetic acid monohydrochloride was purchased from Alfa Aesar.

Company High quality MeOH and Nanopure water (18.1 mΩ) were used for all experiments and solutions.

Nomenclature of the Ligands

GlcC2

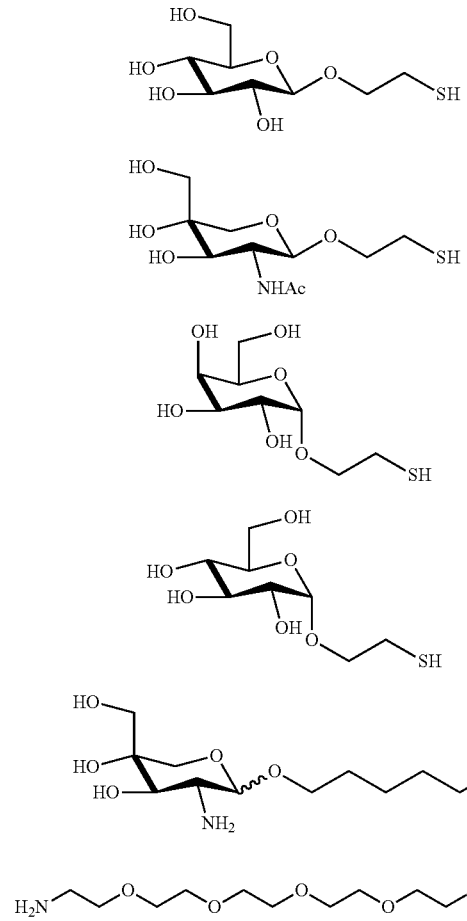

2"-thioethyl-β-D-glucopyranoside (beta)
GlcNHAcC2

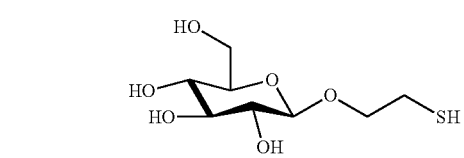

2"-thioethyl-2-acetamido-2-deoxy-β-D-glucopyranoside (beta)

GlcNH2-IAA-C5

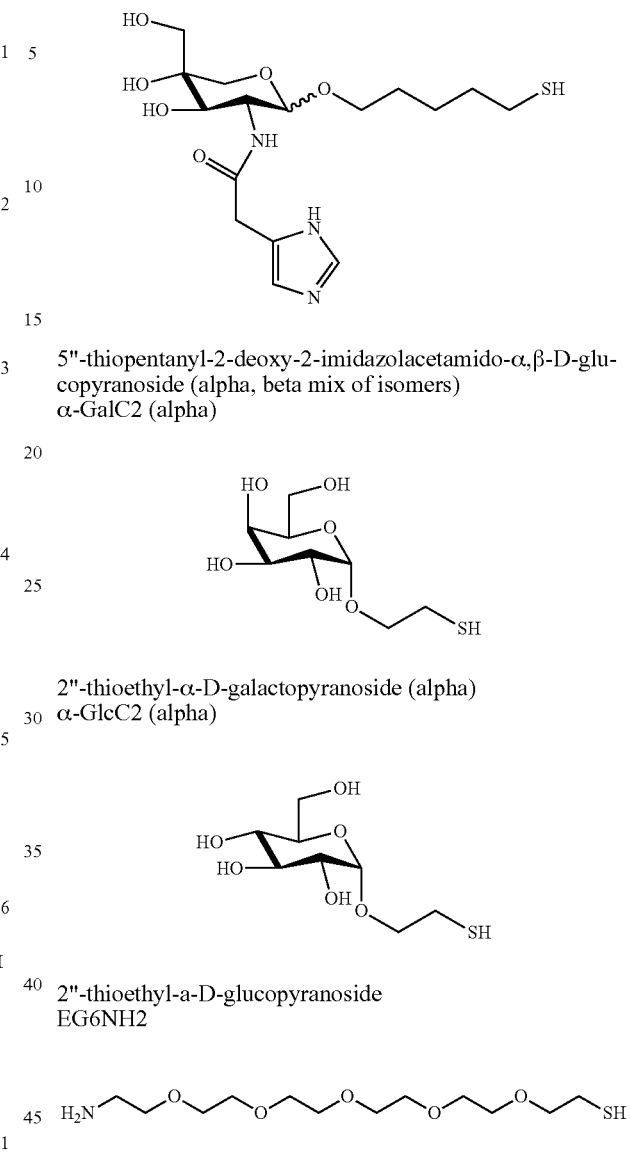

5"-thiopentanyl-2-deoxy-2-imidazolacetamido-α,β-D-glucopyranoside (alpha, beta mix of isomers)
α-GalC2 (alpha)

2"-thioethyl-α-D-galactopyranoside (alpha)
α-GlcC2 (alpha)

2"-thioethyl-a-D-glucopyranoside
EG6NH2

1-amino-17-mercapto-3,6,9,12,15-pentaoxa-heptadecanol or 1-amino-6-mercapto-hexaethylenglycol (vulgar name)

Preparation of Nanoparticles (NP) Having a Plurality of Ligands
NP-GlcC2(9)GlcNAc(1)

To a solution of 1 (21.6 mg, 90 μmmol) and 2 (2.8 mg, 10 μmmol) in MeOH (8.3 mL) a 0.025M aqueous solution of HAuCl$_4$ (1.33 mL, 33 μmmol) was added. The solution was shaken during 30 seconds and then an aqueous solution of NaBH$_4$ 1N (0.67 mL, 0.67 mmol) was added in several portions (134 μL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.) The process was repeated three times, washing with 2 mL of water. The residue was dissolved in 7 mL of water. An aliquot was freeze dried for quantitation. [NP]=0.8 mg/mL.

Without wishing to be bound by any theory, a schematic representation of the resulting nanoparticles having a plurality of ligands in the ratio 9:1 of GlcC2:GlcNAc "NP-GlcC2(9)GlcNAc(1)" is shown in FIG. 1.

NP-GlcC2(4)GlcNAc(1)

To a solution of 1 (19.2 mg, 80 μmmol) and 2 (5.6 mg, 20 μmmol) in MeOH (8.3 mL) a 0.025M aqueous solution of $HAuCl_4$ (1.33 mL, 33 μmmol) was added. The solution was shaken during 30 seconds and then an aqueous solution of $NaBH_4$ 1N (0.67 mL, 0.67 mmol) was added in several portions (134 μL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.) The process was repeated three times, washing with 2 mL of water. The residue was dissolved in 7 mL of water. An aliquot was freeze dried for quantitation. [NP]=0.8 mg/mL.

Figure 2:
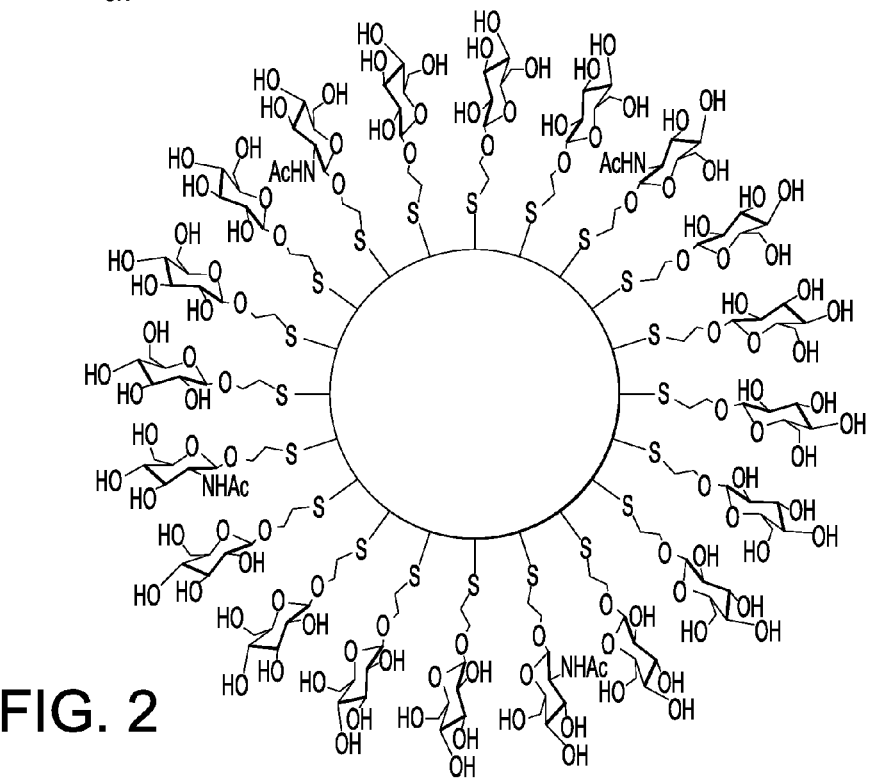
FIG. 2 shows a schematic representation of nanoparticles having a plurality of ligands in the ratio 4:1 of GlcC2:GlcNAc "NP-GlcC2(4) GlcNAc(1)"

Without wishing to be bound by any theory, a schematic representation of the resulting nanoparticles having a plurality of ligands in the ratio 4:1 of GlcC2:GlcNAc "NP-GlcC2(4)GlcNAc(1)" is shown in FIG. 2.

NP-GlcC2(1)GlcNAc(1)

To a solution of 1 (12 mg, 50 μmmol) and 2 (14 mg, 50 μmmol) in MeOH (8.3 mL) a 0.025M aqueous solution of $HAuCl_4$ (1.33 mL, 33 μmmol) was added. The solution was shaken during 30 seconds and then an aqueous solution of $NaBH_4$ 1N (0.67 mL, 0.67 mmol) was added in several portions (134 μL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.) The process was repeated three times, washing with 2 mL of water. The residue was dissolved in 7 mL of water. An aliquot was freeze dried for quantitation. [NP]=0.9 mg/mL.

Figure 3:
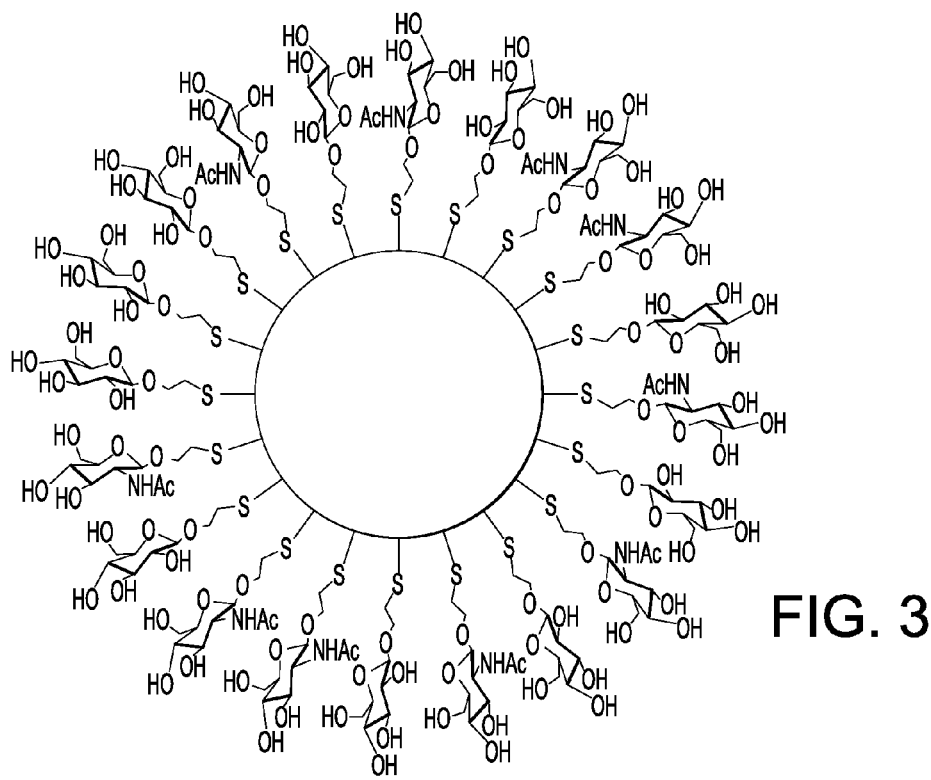
FIG. 3 shows a schematic representation of nanoparticles having a plurality of ligands in the ratio 1:1 of GlcC2:GlcNAc "NP-GlcC2(1) GlcNAc(1)"

Without wishing to be bound by any theory, a schematic representation of the resulting nanoparticles having a plurality of ligands in the ratio 1:1 of GlcC2:GlcNAc "NP-GlcC2(1)GlcNAc(1)" is shown in FIG. 3.

NP-GlcC2(1)GlcNAc(9)

To a solution of 1 (2.4 mg, 10 μmmol) and 2 (25.3 mg, 90 μmmol) in MeOH (8.3 mL) a 0.025M aqueous solution of $HAuCl_4$ (1.33 mL, 33 μmmol) was added. The solution was shaken during 30 seconds and then an aqueous solution of $NaBH_4$ 1N (0.67 mL, 0.67 mmol) was added in several portions (134 μL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.) The process was repeated three times, washing with 2 mL of water. The residue was dissolved in 7 mL of water. An aliquot was freeze dried for quantitation. [NP]=0.8 mg/mL.

Figure 4:
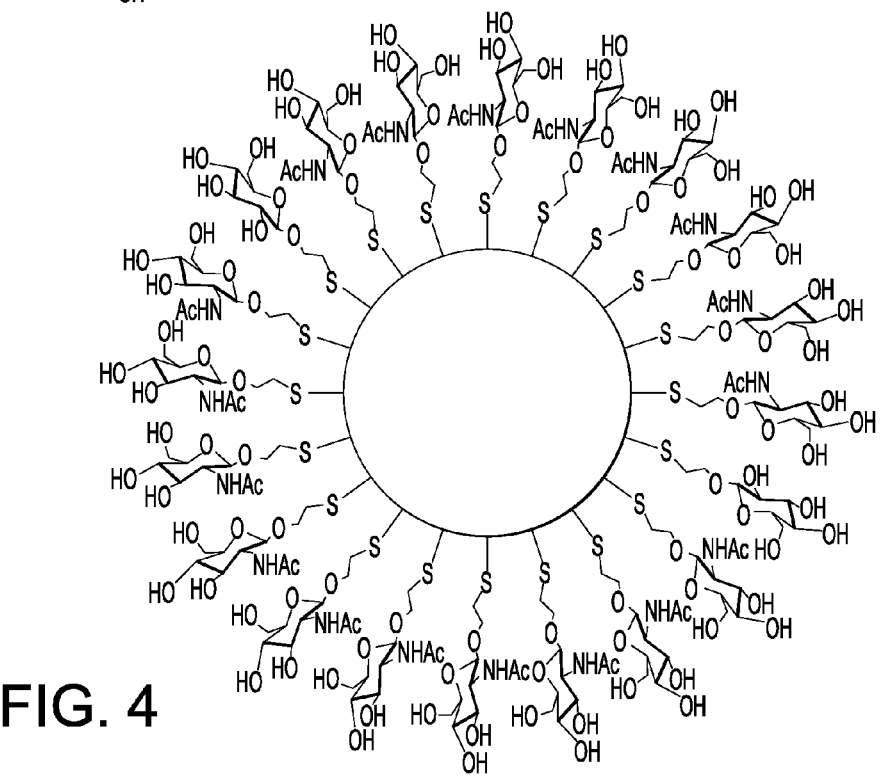
FIG. 4 shows a schematic representation of nanoparticles having a plurality of ligands in the ratio 1:9 of GlcC2:GlcNAc "NP-GlcC2(1)GlcNAc(9)"

Without wishing to be bound by any theory, a schematic representation of the resulting nanoparticles having a plurality of ligands in the ratio 1:9 of GlcC2:GlcNAc "NP-GlcC2(1)GlcNAc(9)" is shown in FIG. 4.

NP-GlcC2(1)alpha-Gal(1)

To a solution of 1 (12 mg, 50 μmmol) and 3 (12 mg, 50 μmmol) in MeOH (8.3 mL) a 0.025M aqueous solution of $HAuCl_4$ (1.33 mL, 33 μmmol) was added. The solution was shaken during 30 seconds and then an aqueous solution of $NaBH_4$ 1N (0.67 mL, 0.67 mmol) was added in several portions (134 μL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.) The process was repeated three times, washing with 2 mL of water. The residue was dissolved in 7 mL of water. An aliquot was freeze dried for quantitation. [NP]=0.7 mg/mL.

Figure 5:
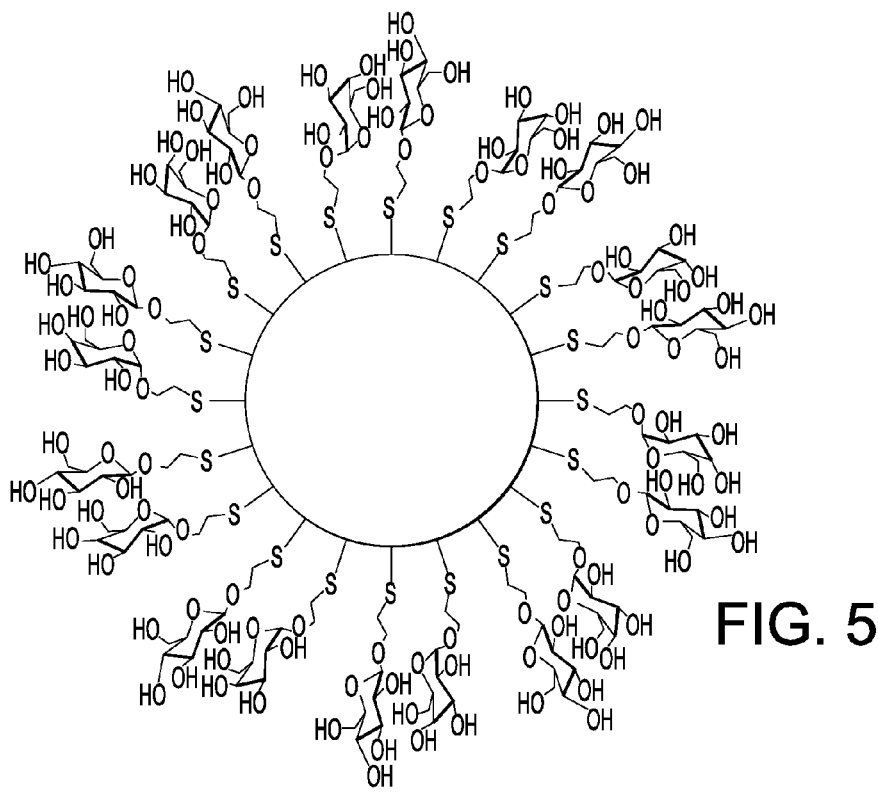
FIG. 5 shows a schematic representation of nanoparticles having a plurality of ligands in the ratio 1:1 of GlcC2:alpha-Gal "NP-GlcC2(1)alpha-Gal(1)"

Without wishing to be bound by any theory, a schematic representation of the resulting nanoparticles having a plurality of ligands in the ratio 1:1 of GlcC2:alpha-Gal "NP-GlcC2(1)alpha-Gal(1)" is shown in FIG. 5.

NP-betaGlcC2(1)EG6NH2(1)

To a solution of 1 (12 mg, 50 μmmol) and 6 (14.85 mg, 50 μmmol) in MeOH (8.3 mL) a 0.025M aqueous solution of $HAuCl_4$ (1.33 mL, 33 μmmol) was added. The solution was shaken during 30 seconds and then an aqueous solution of $NaBH_4$ 1N (0.67 mL, 0.67 mmol) was added in several portions (134 μL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.) The process was repeated three times, washing with 2 mL of water. The residue was dissolved in 7 mL of water. An aliquot was freeze dried for quantitation. [NP]=0.9 mg/mL.

Figure 6:
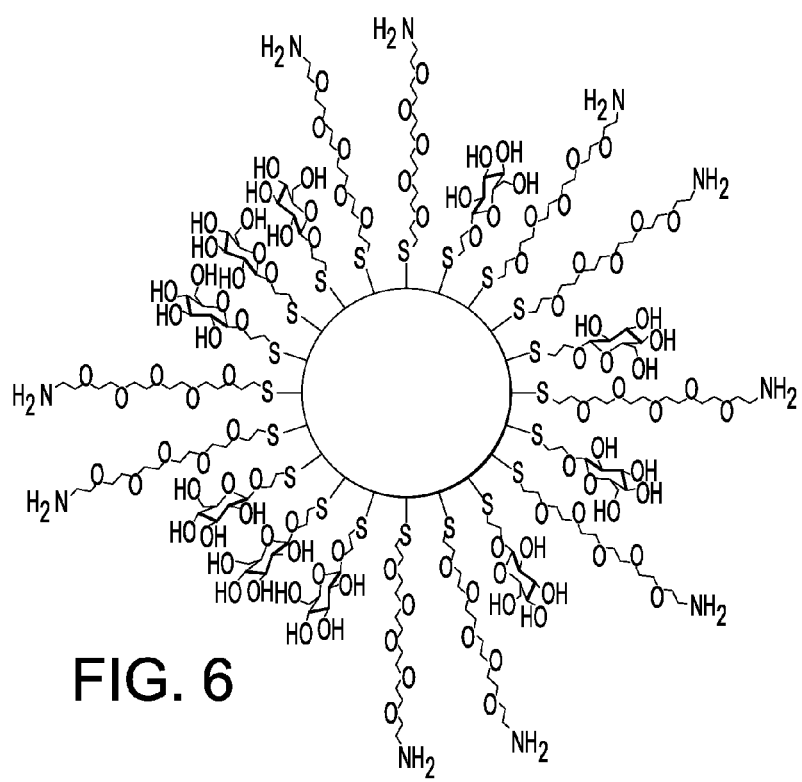
FIG. 6 shows a schematic representation of nanoparticles having a plurality of ligands in the ratio 1:1 of betaGlcC2:EG6NH2 "NP-betaGlcC2(1)EG6NH2(1)"

Without wishing to be bound by any theory, a schematic representation of the resulting nanoparticles having a plurality of ligands in the ratio 1:1 of betaGlcC2:EG6NH2 "NP-betaGlcC2(1)EG6NH2(1)" is shown in FIG. 6.

NP-GlcNHAc(1) EG6NH2(1)

To a solution of 2 (14 mg, 50 μmmol) and 6 (14.85 mg, 50 μmmol) in MeOH (8.3 mL) a 0.025M aqueous solution of $HAuCl_4$ (1.33 mL, 33 μmmol) was added. The solution was shaken during 30 seconds and then an aqueous solution of $NaBH_4$ 1N (0.67 mL, 0.67 mmol) was added in several portions (134 μL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.) The process was repeated three times, washing with 2 mL of water. The residue was dissolved in 6 mL of water. An aliquot was freeze dried for quantitation. [NP]=0.6 mg/mL.

Figure 7:
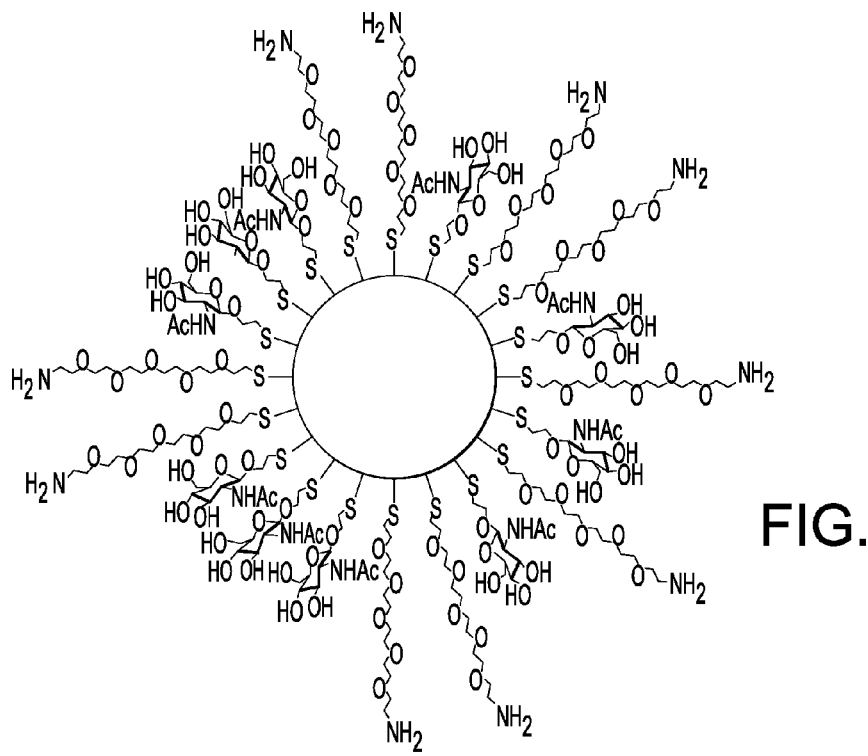
FIG. 7 shows a schematic representation of nanoparticles having a plurality of ligands in the ratio 1:1 of GlcNHAc:EG6NH2 "NP-GlcNHAc(1) EG6NH2(1)"

Without wishing to be bound by any theory, a schematic representation of the resulting nanoparticles having a plurality of ligands in the ratio 1:1 of GlcNHAc:EG6NH2 "NP-GlcNHAc(1)EG6NH2(1)" is shown in FIG. 7.

NP-alpha-Glc(1)EG6NH2(1)

To a solution of 4 (12 mg, 50 μmmol) and 6 (14.85 mg, 50 μmmol) in MeOH (8.3 mL) a 0.025M aqueous solution of $HAuCl_4$ (1.33 mL, 33 μmmol) was added. The solution was shaken during 30 seconds and then an aqueous solution of $NaBH_4$ 1N (0.67 mL, 0.67 mmol) was added in several portions (134 μL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.) The process was repeated three times, washing with 2 mL of water. The residue was dissolved in 4 mL of water. An aliquot was freeze dried for quantitation. [NP]=0.8 mg/mL.

Figure 8:
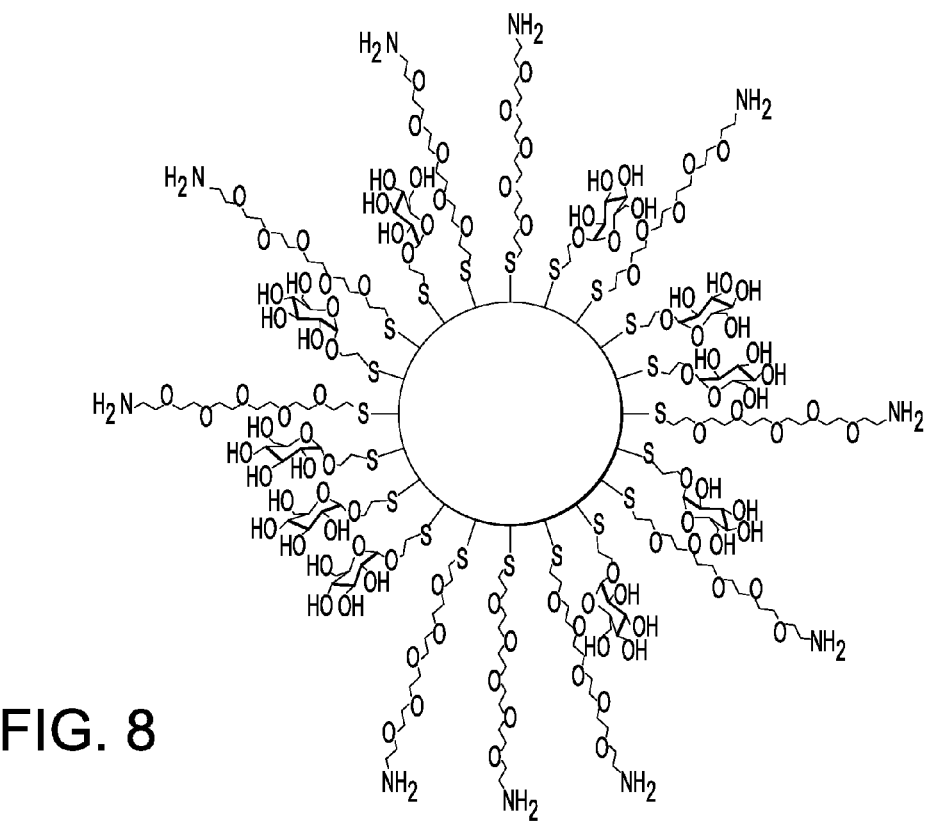
FIG. 8 shows a schematic representation of nanoparticles having a plurality of ligands in the ratio 1:1 of alpha-Glc:EG6NH2 "NP-alpha-Glc(1)EG6NH2(1)"

Without wishing to be bound by any theory, a schematic representation of the resulting nanoparticles having a plurality of ligands in the ratio 1:1 of alpha-Glc:EG6NH2 "NP-alpha-Glc(1)EG6NH2(1)" is shown in FIG. 8.

NP-alpha-Glc

To a solution of 4 (24 mg, 100 μmmol) in MeOH (8.3 mL) a 0.025M aqueous solution of $HAuCl_4$ (1.33 mL, 33 μmmol) was added. The solution was shaken during 30 seconds and then an aqueous solution of $NaBH_4$ 1N (0.67 mL, 0.67 mmol) was added in several portions (134 μL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.). The process was repeated three times, washing with 2 mL of water. The residue was dissolved in 5 mL of water. An aliquot was freeze dried for quantitation. [NP]=1.0 mg/mL.

Figure 9:
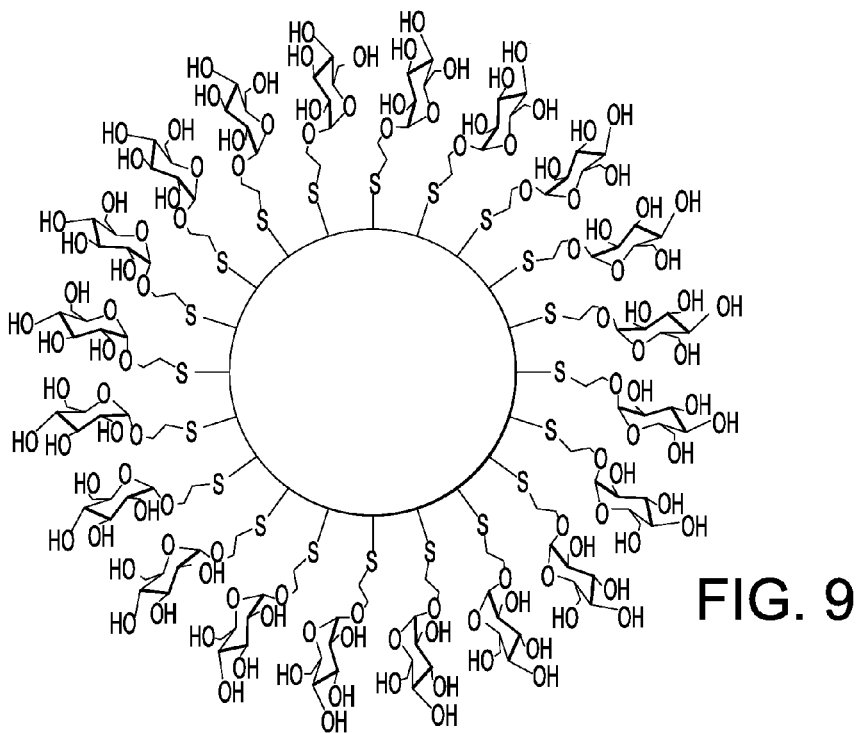
FIG. 9 shows a schematic representation of nanoparticles having a plurality of ligands of alpha-Glc "NP-alpha-Glc"

Without wishing to be bound by any theory, a schematic representation of the resulting nanoparticles having a plurality of ligands of alpha-Glc "NP-alpha-Glc" is shown in FIG. 9.

NP-GlcC2(1)GlcNH IAA(1)

To a solution of 1 (12 mg, 50 μmmol) and 5 (12 mg, 50 μmmol) in MeOH (8.3 mL) a 0.025M aqueous solution of $HAuCl_4$ (1.33 mL, 33 μmmol) was added. The solution was shaken during 30 seconds and then an aqueous solution of $NaBH_4$ 1N (0.67 mL, 0.67 mmol) was added in several portions (134 μL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.) The process was repeated three times, washing with 2 mL of water. The residue was dissolved in 8 mL of 100 mM MES and treated with EDC (153 mg, 0.8 mmol) and imidazole-4-acetic acid monohydrochloride (81 mg, 0.5 mmol) for 14 hours. The mixture was and purified by centrifugal filtering (10 KDa AMICON 4 mL, 4500 g, 15 min, 15° C.). The process was repeated three times, washing with 2 mL of water. The residue was dissolved in 4 mL of water. An aliquot was freeze dried for quantitation. [NP]=0.9 mg/mL.

Figure 10:
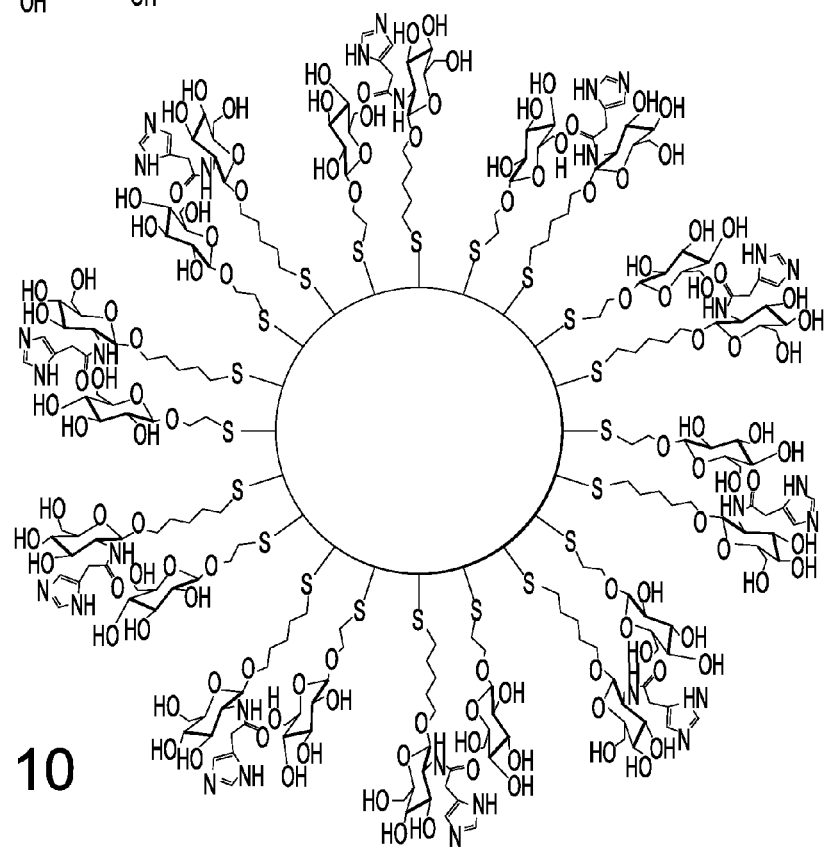
FIG. 10 shows a schematic representation of nanoparticles having a plurality of ligands in the ratio 1:1 of GlcC2:GlcNH_IAA "NP-GlcC2(1) GlcNH_IAA(1)"

Without wishing to be bound by any theory, a schematic representation of the resulting nanoparticles having a plurality of ligands in the ratio 1:1 of GlcC2:GlcNH_IAA "NP-GlcC2(1)GlcNH_IAA(1)" is shown in FIG. 10.

NP-alpha-Gal(1)EG6NH2(1)

Preparation of amine alpha-gal gold nanoparticles Batch MI-NP-10-AMINE-GAL: To a mix of amine-mercapto hexaethylenglycol linker 6 and alpha-galactose ligand 3 in a ratio 1:1 (0.58 mmol, 3 eq.) in MeOH (49 mL) was added an aqueous solution of gold salt (7.86 mL, 0.19 mmol, 0.025M). The reaction was stirred during 30 seconds and then, an aqueous solution of $NaBH_4$ (1N) was added in several portions (4.32 mL, 4.32 mmol). The reaction was shaken for 100 minutes at 900 rpm. After this time, the suspension was centrifuged 1 minute at 14000 rpm. The supernatant is removed and the precipitated was dissolved in 2 mL of water. Then, 2 mL of the suspension were introduced in two filters (AMICON, 10 KDa, 4 mL) and were centrifuged 5 minutes at 4500 g. The residue in the filter was washed twice more with water. The final residue was dissolved in 80 mL of water.

Figure 11:
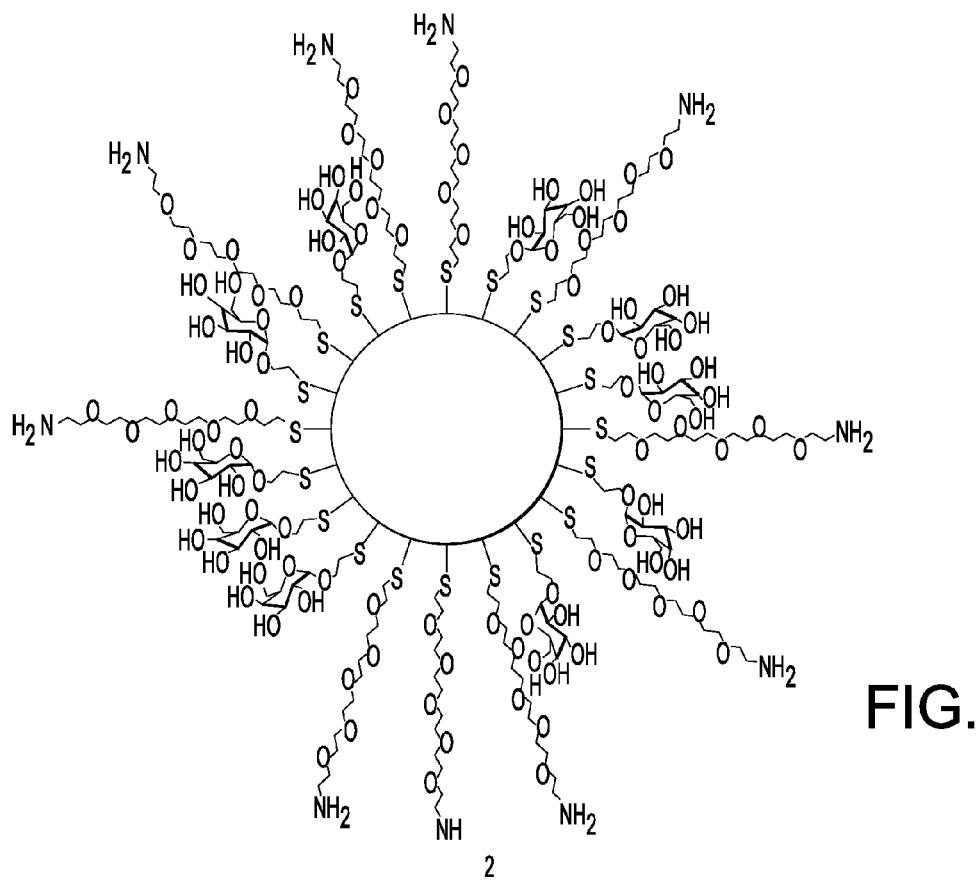
FIG. 11 shows a schematic representation of nanoparticles having a plurality of ligands in the ratio 1:1 of alpha-Gal:EG6NH2 "NP-alpha-Gal(1)EG6NH2(1)". In certain examples, the NP-alpha-Gal(1)EG6NH2(1) nanoparticles are referred to herein as batch NP10.

Without wishing to be bound by any theory, a schematic representation of the resulting nanoparticles having a plurality of ligands in the ratio 1:1 of alpha-Gal:EG6NH2 "NP-alpha-Gal(1)EG6NH2(1)" is shown in FIG. 11.

For the preparation of gold NPs manufacture was under laminar flow cabinet. All glass and plastic material (such as eppendorfs, vials and bottles) and solvent (water, HAc) were first sterilized in an autoclave. All other disposables (such as tips and filters) came pre-sterilized.

Example 3

Insulin Binding to Nanoparticles

The following method details how the binding of insulin to alphaGal(1) EG6NH2(1) NPs was performed. The method used fixed insulin and variable NP levels, lower/different levels of NP were used for the other NP samples tested, but with this exception the method was the same for all NPs tested.

Preparation of insulin stock solution; weight 20 mg human insulin into a clean glass vial and add 8.7 ml 10 mM HCl mix gently insulin will dissolve completely, then pH back to 7.5 by adding 1.3 ml 100 mM Tris base, the solution will go cloudy briefly as the insulin passes through its isoelectric point, check the pH is 7.5 and store capped at 4° C., this is the 2 mg/ml insulin stock solution.

Add variable amounts of alphaGal(1) EG6NH2(1) NPs to an eppendorf or suitably sized vessel, for example; 15, 30, 60, 120, 240 and 480 nmoles gold content of NP, make up to a total volume of 200 μl with water, then add 50 μl of human insulin (2 mg/ml in tris HCl pH7.5—see above for preparation of insulin stock solution). Mix gently and leave at room temp for 2 h, follow with a 2 minute bench spin (2000 rpm) to bring down the aggregate. A standard tube which has just 200 μl water and 50 μl insulin should be performed to give the maximum supernatant value, as should a blank i.e. 50 μl Tris HCl pH7.5+200 μl water. If high accuracy is required a sample containing a known amount of alphaGal(1) EG6NH2 (1) NP i.e. 10 μg gold content is made up to 200 μl with water, and 50 μl of the insulin buffer added (Tris HCl pH7.5), this can be used to correct for the slight positive result the alphaGal(1) EG6NH2(1) NP gives in the BCA assay see below*.

Assay the supernatants, 20 μl in triplicate by standard micro BCA assay (Pierce kit 23235), this will give data showing how much insulin remains in supernatant. By subtracting this value from the value for the insulin only standard calculate the amount of NP bound insulin, it can also be expressed as a percent if required. The data obtained here shows the amount of alphaGal(1) EG6NH2(1)-NP that if required to maximally bind the 100 μg of insulin used, these conditions can be scaled up to produce the amount alphaGal(1) EG6NH2 (1)-NP-insulin required.

*The data can be correcting for the slight interference of the free alphaGal(1) EG6NH2(1)-NP in the BCA assay. To do this perform a gold analysis on all the final samples and calculate how much gold remains in the various supernatants, higher levels will be seen in samples with an excess of NP to insulin. Use the BCA value for the 10 μg gold content NP to correct relative to the gold content seen, as demonstrated by the following example:

If the 10 μg gold content NP without insulin gives 0.5 by BCA and 40 μg Au test NP supernatant gives BCA of 1.25, and also shows gold content of 5 μg, that means 0.25 of BCA value (50% of 0.5) is actually due to the free NP, hence corrected value for 40 μg gold test NP supernatant should be 1.00 not 1.25. This is a simplified, illustrative example, the correction factor will be minimal where the gold content in the supernatant is low.

Figure 12:
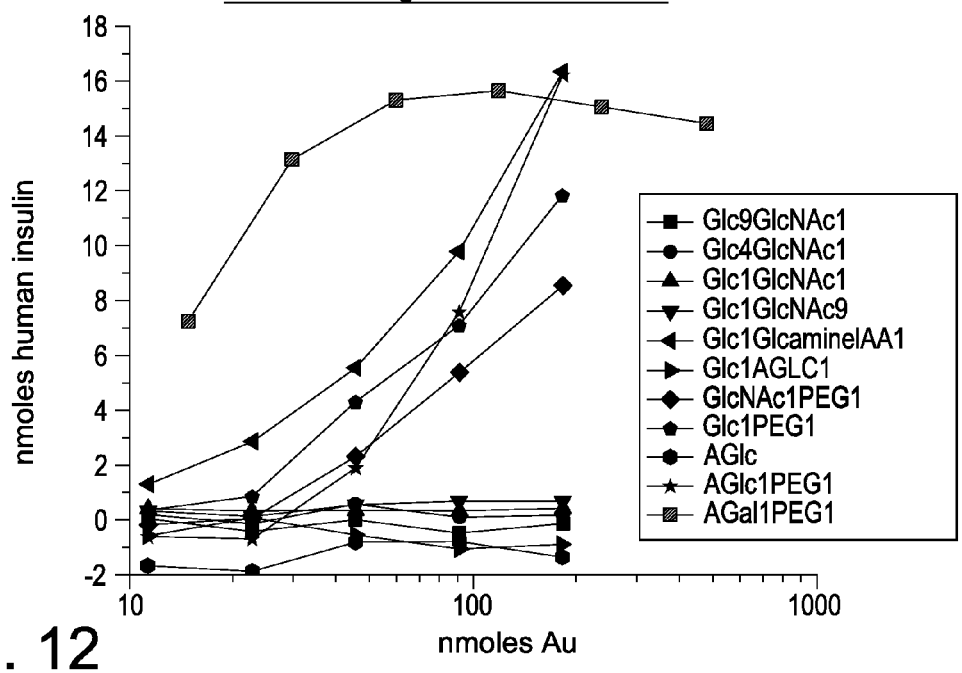
FIG. 12 shows insulin binding curves of human insulin bound (in nmoles) per amount of gold (in nmoles) for 11 different nanoparticle coronal compositions.

The amount of human insulin bound (in nmoles) per amount of gold (in nmoles) is shown in FIG. 12, wherein:

Glc=2'-thioethyl-β-D-glucopyranoside;

GlcNAc=2'-thioethyl-2-acetamido-2-deoxy-β-D-glucopyranoside;

GlcamineIAA=5'-thiopentanyl-2-deoxy-2-imidazolacetamido-α,β-D-glucopyranoside (alpha, beta mix of isomers);

AGal=2'-thioethyl-α-D-galactopyranoside;

EG6NH2=1-amino-17-mercapto-3,6,9,12,15-pentaoxa-heptadecanol;

AGlc=2'-thioethyl-α-D-glucopyranoside; and

The numbers in the legend refer to the ligand stiochiometry.

As can be seen by reference to FIG. 12, a relatively high degree of insulin binding was obtained using nanoparticles having a corona of AGal and EG6NH2 in approximately 1:1 ratio. Insulin binding was also exhibited by nanoparticles having any of the following corona compositions:

AGal: EG6NH2 1:1 (Trace 11 FIG. 12)

Glc:GlcamineIAA 1:1 (Trace 10 FIG. 12)

AGlc: EG6NH2 1:1 (Trace 8 FIG. 12)

BGlc: EG6NH2 1:1 (Trace 6 FIG. 12)

GlcNAc: EG6NH2 1:1 (Trace 7 FIG. 12).

Example 4

Characterisation of Nanoparticles

I) Characterization of Insulin Gold Nanoparticles Batch MI-NP-10-Ins (NP-alpha-Gal(1)EG6NH2(1))

a) Gold content: The gold content was determined using a method based on the formation of a coloured complex between ethopropazine and the gold after complete oxidation to Au(III). The absorbance of the sample is measured at 513 nm and quantitatively compared to similar solutions having a known amount of gold.

The gold content was determined to be (batch # NP10): 262.5±56.3 mg/L.

Figure 13:
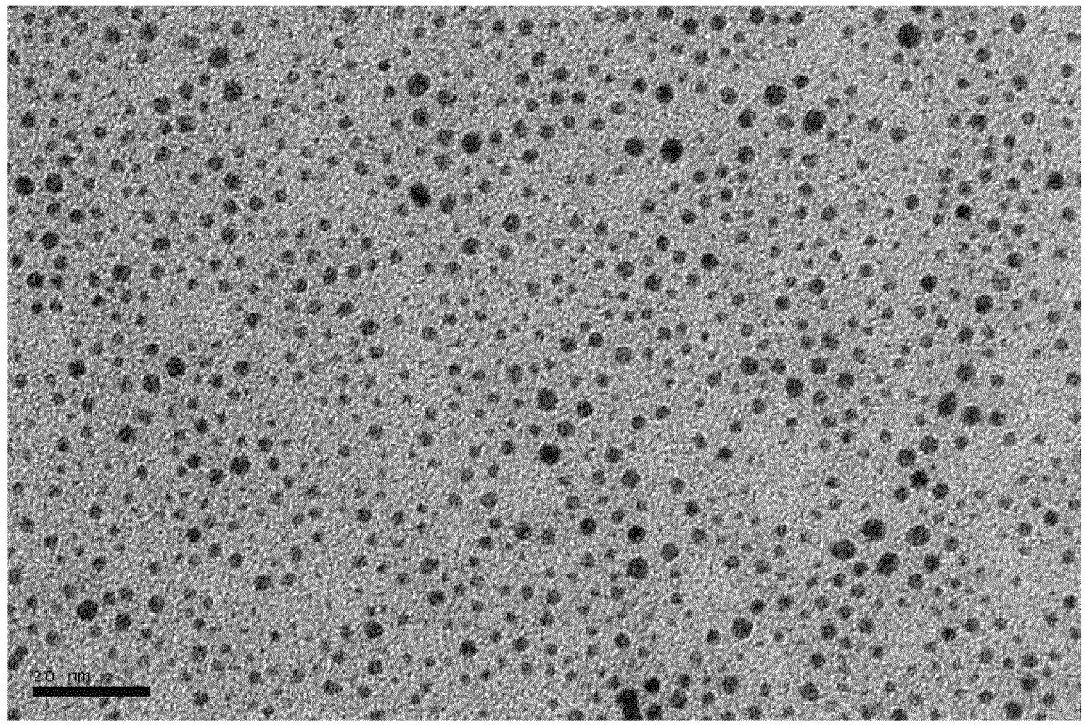
FIG. 13 shows a transmission electron microscopy (TEM) image NP-alpha-Gal(1)EG6NH2(1) nanoparticles {batch # NP10}.

TEM: a transmission electron microscopy (TEM) image of the nanoparticle suspension is shown in FIG. 13.

The sample was determined to have the following size characteristics for the gold core:

Count=783

Mean (diameter)=2.323 nm±0.716 nm

Min.=1.002 nm

Max.=4.859 nm

Mode=2.104 nm b) Size distribution by Dynamic Light Scattering: number and volume distributions were determined by dynamic light scattering (DLS) for MI-NP-10 amine-gal (i.e. NP-alpha-Gal(1)EG6NH2(1) nanoparticles), and are shown in FIGS. 14 A and B, respectively.

Figure 14A:
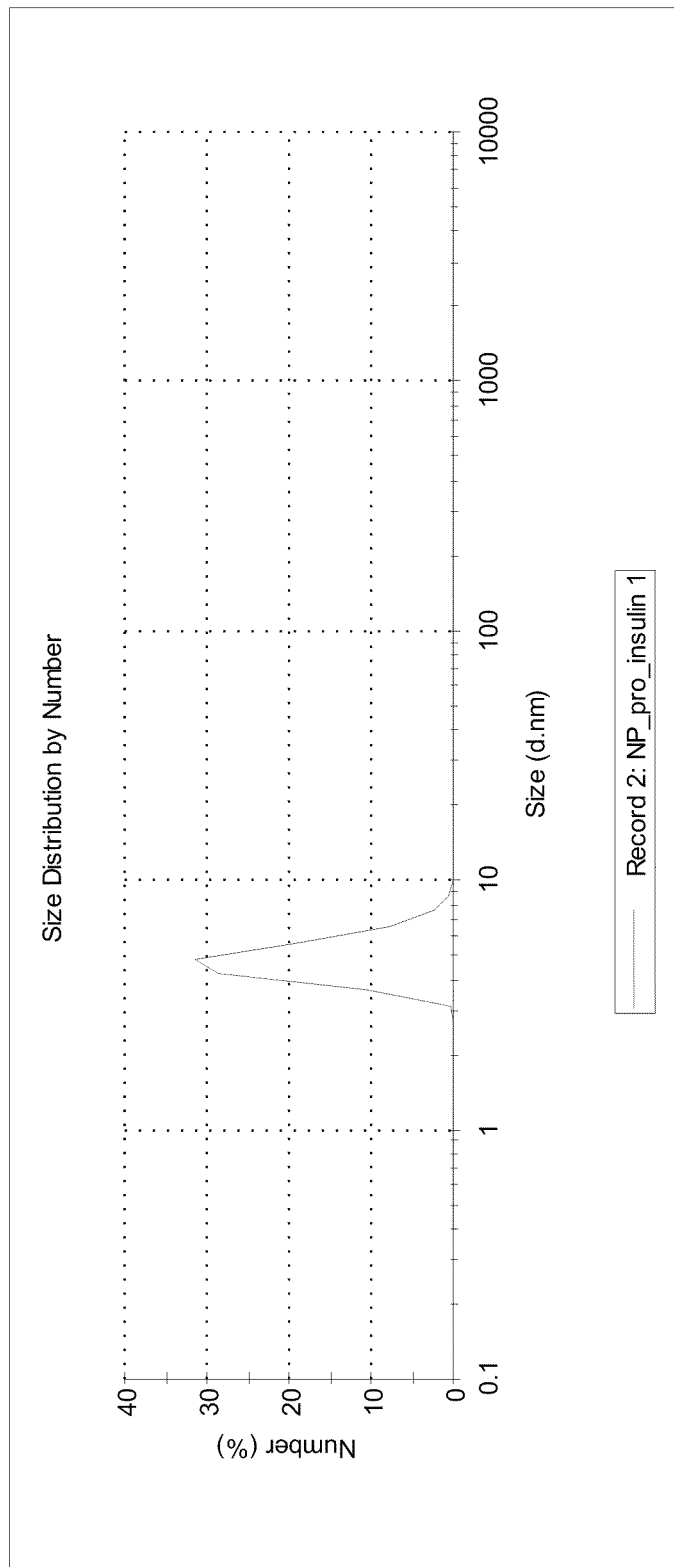
FIG. 14 shows size distribution plots determined by dynamic light scattering (DLS) for MI-NP-10 amine-gal (i.e. NP-alpha-Gal(1)EG6NH2(1) nanoparticles) by, A) number and B) volume.

The peak value for the peak shown in FIG. 14A is as follows:

Peak 1 4.875 nm

Figure 14B:
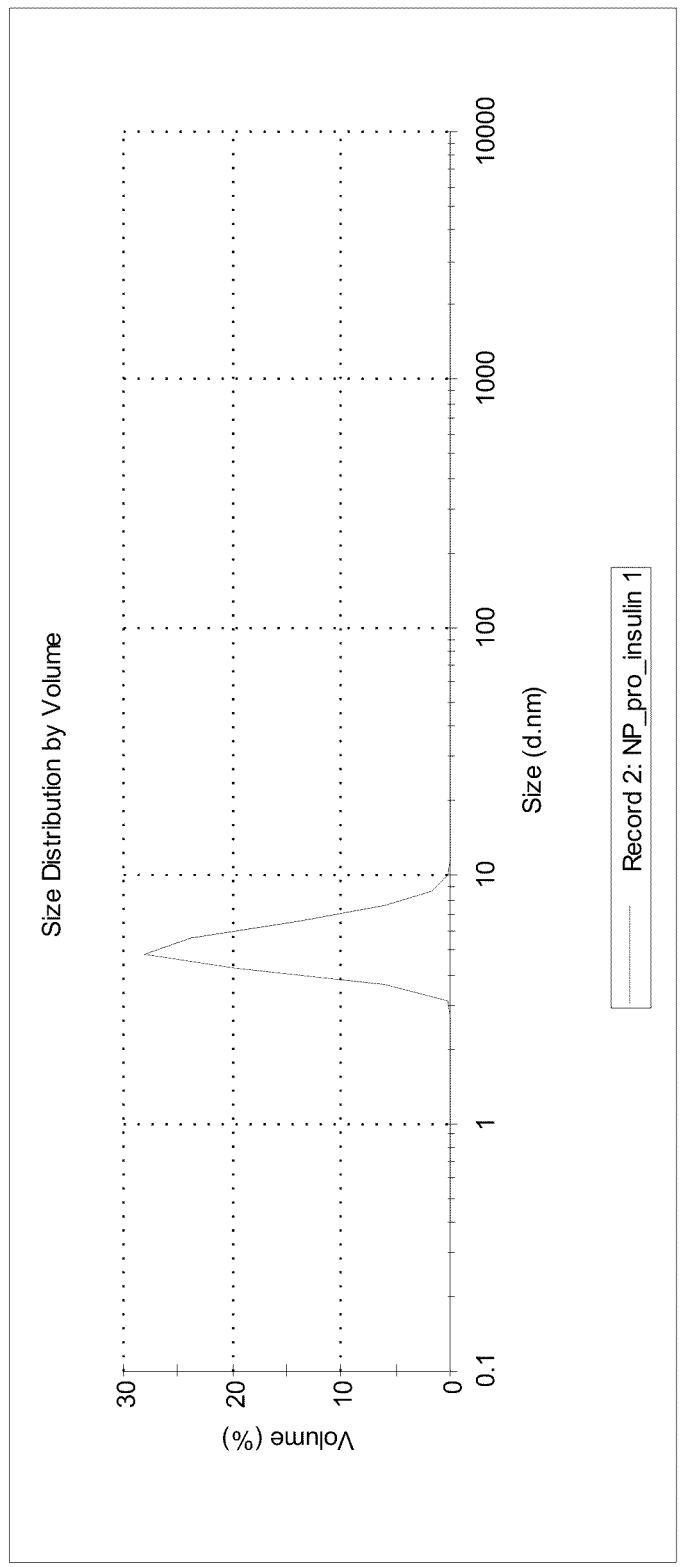

The peak value for the peak shown in FIG. 14B is as follows:

Peak 1 5.289 nm

II) Final Preparation of Insulin Gold Nanoparticles Batch MI-NP-10-INS.

A solution of gold nanoparticles MI-NP-10 (13.041 mg gold) was made up to 49.68 mL of water. To the final solution was added acetic acid to obtain a pH=4.6. Then, 55.7 mg of human insulin in 27.85 mL of Tris.HCl pH 7.5 was added. The suspension was left 24 hours and after this time, was centrifuged 1 minute at 4500 g. The supernatant was removed and stored for further insulin and gold content analysis. The precipitate was resuspended in 3.220 mL of water to get a final insulin concentration of 500 units insulin/mL.

The size distribution of the insulin-gold nanoparticles was determined by DLS analysis. The insulin content was determined by BCA standard assay.

** The final preparation of insulin gold NP was manufactured under laminar flow cabinet. All glass and plastic material (such as eppendorfs and bottles) and solvent (such as water, TrisHCl and HAc) used were sterilized in an autoclave. All other disposables (such as tips and filters) came pre-sterilized.

Characterisation:

a) Size distribution by Dynamic Light Scattering is shown by number and volume in FIG. 15 A, and B, respectively for MI-NP-10-INS (amine-gal-INSULIN nanoparticles).

Figure 15A:
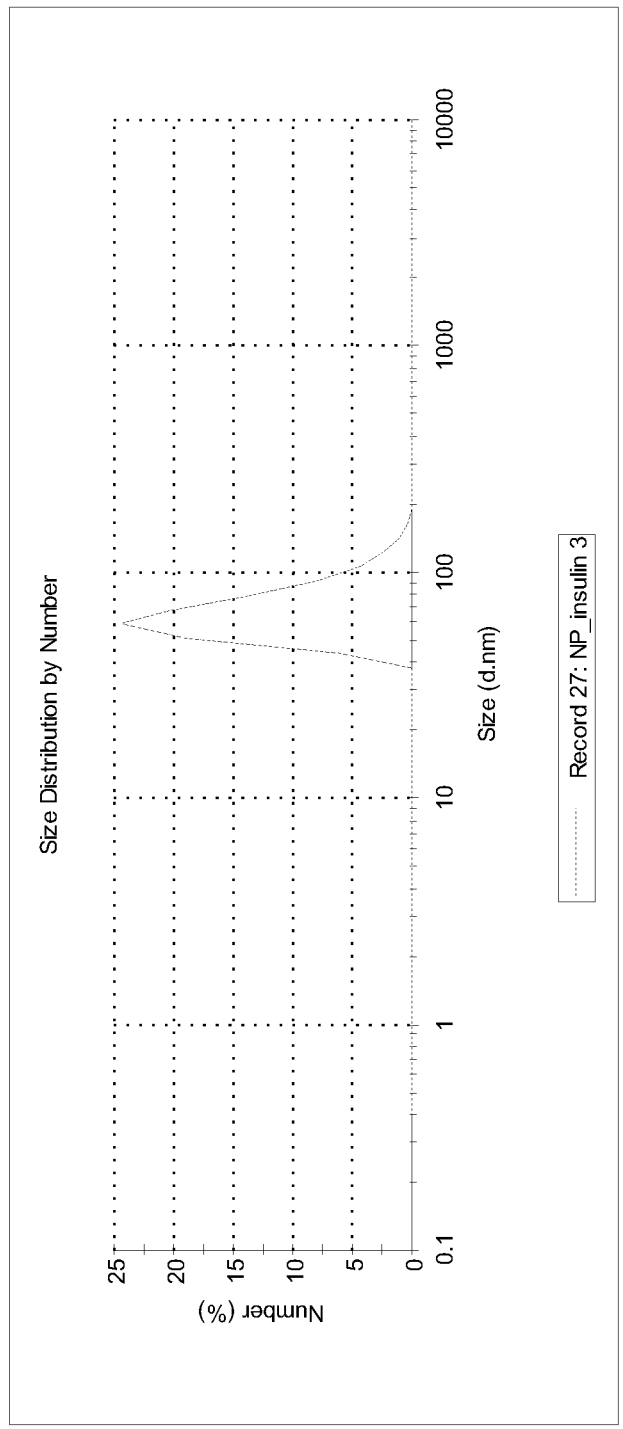
FIG. 15 shows size distribution plots determined by dynamic light scattering (DLS) for insulin bound-MI-NP-10 amine-gal (i.e. NP-alpha-Gal(1)EG6NH2(1) nanoparticles) by A) number and B) volume.

The peak value for the peak shown in FIG. 15A is as follows:

Peak 1 68.46 nm

Figure 15B:
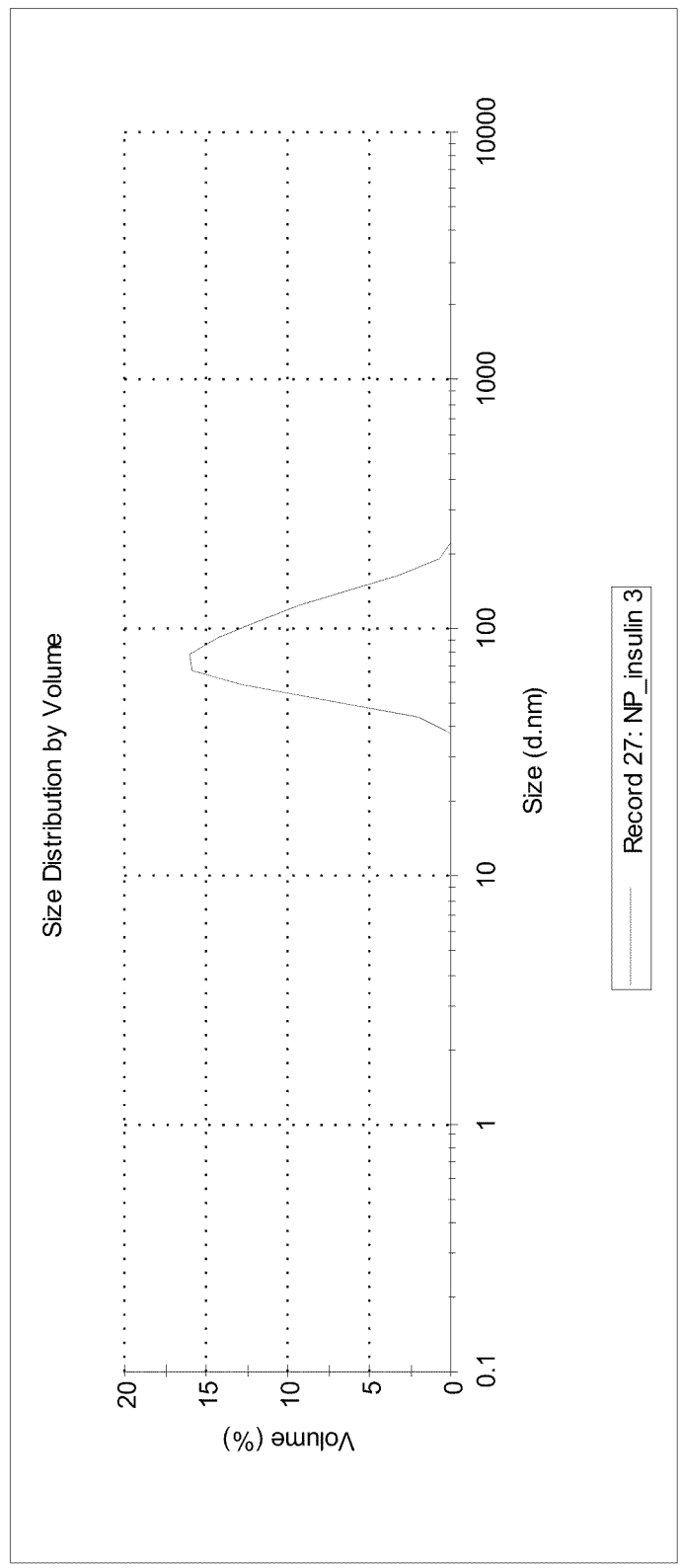

The peak value for the peak shown in FIG. 15B is as follows:

Peak 1 88.38 nm b) Insulin content:

The % of insulin binding to the nanoparticles was determined by the following formula:

$$\% \text{ insulin} = \frac{\text{insulin added} - \text{insulin supernatant}}{\text{insulin added}} \times 100$$

TABLE 2

| | Insulin content | | | |
|---|---|---|---|---|
| Sample | Insulin added (mg) | Insulin supernatant (mg) | Insulin bound (mg) | % insulin bound |
| MI-NP-10 insulin | 55.700 | 1.308 | 54.4 | 97.65 |

Concentration of insulin and gold in NP-insulin nanoparticles:

Insulin: 55.7 mg Insulin

Gold: 13.041 mg of gold

Total volume: 3.23 mL water

Final insulin concentration: 17.25 mg insulin/mL=500 units/mL

Final gold concentration: 4.037 mg Au/mL.

Without wishing to be bound by any theory, the present inventors consider the following:

102 Au atoms/NP, for which the mathematical result is 14 insulin molecules attached to 1 NP. Since geometrical considerations allow space for about 7 insulin molecules on the surface of the nanoparticle, these results suggest that each NP contains 7 insulin dimer units.

Further characterisation of the insulin gold nanoparticles Batch MI-NP-10-INS yielded the following results.

Final insulin concentration: 17.25 mg insulin/mL=500 U/mL, determined by colorimetric bicinchonicic acid assay after calibration against insulin standardized solutions of known concentrations.

Final gold concentration: 4.037 mg Au/mL, determined by colorimetric assay with ethopropazine assay after calibration against gold standardized solutions of known concentrations.

Total volume: 3.23 mL in MilliQ water.

After geometrical considerations, one α-galactose-EG-amine-Au nanoparticle contains a gold core with 102 atoms. Then:

4.037 mg=2.049e-5 moles=1.234e19 atoms=1.21e17 nanoparticles 17.25 mg=2.97e-6 moles=1.789e18 molecules Therefore one α-galactose-EG6NH2-Au nanoparticle is bound to about between 14 and 15 insulin molecules to produce the final nanoparticle.

Results from thermogravimetric analysis:

Without wishing to be bound by any theory, the present inventors consider that for insulin-NP we have 500 ug of dry weight in which 410 ug is decomposed. Therefore the percent organic is 82%. Considering 102 atoms of gold in one α-galactose-EG6NH2-Au nanoparticle, gold weight would be 20091 (18%) and an organic corona 12122. Therefore to have a particle that is 82% organic it must have weight of 111616 that is 91525 organic. Since 12122 of organic is corona that leaves about 79403 of the organic as insulin. Since insulin has MW 5808 then we must have 14 moles insulin per particle.

Figure 16:
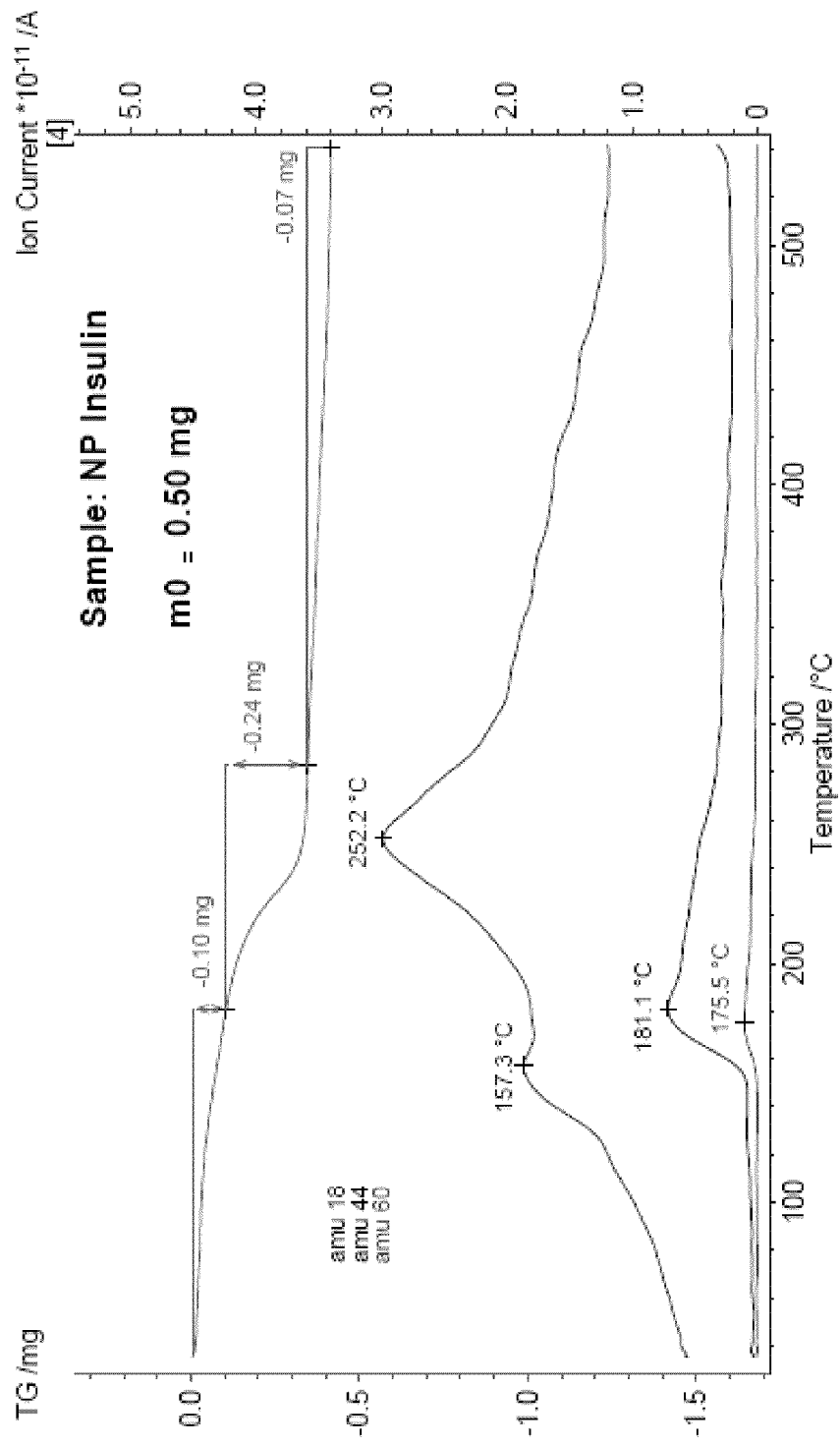
FIG. 16 shows experimental thermogravimetric analysis (TGA) data for α-galactose-EG-amine-Au nanoparticles with temperature peaks indicated {batch # NP10}.

FIG. 16 shows the experimental thermogravimetric analysis (TGA) data.

Example 5

Zn Optimisation of Insulin Binding

Gold nanoparticles (NPs), alphaGal(1) EG6NH2(1) NPs, were prepared as described in Example 2 above. In order to evaluate the influence of Zn on insulin binding to the NPs, a first batch of NPs was synthesised in the absence of Zn. A second batch of NPs was synthesised in the presence of 1.33 equivalents of Zn. A third batch of NPs was synthesised in the absence of Zn, but had 1.33 equivalents of $ZnCl_2$ added to the NPs post-synthesis. The binding of human insulin to the three batches of gold NPs was then measured.

Figure 17:
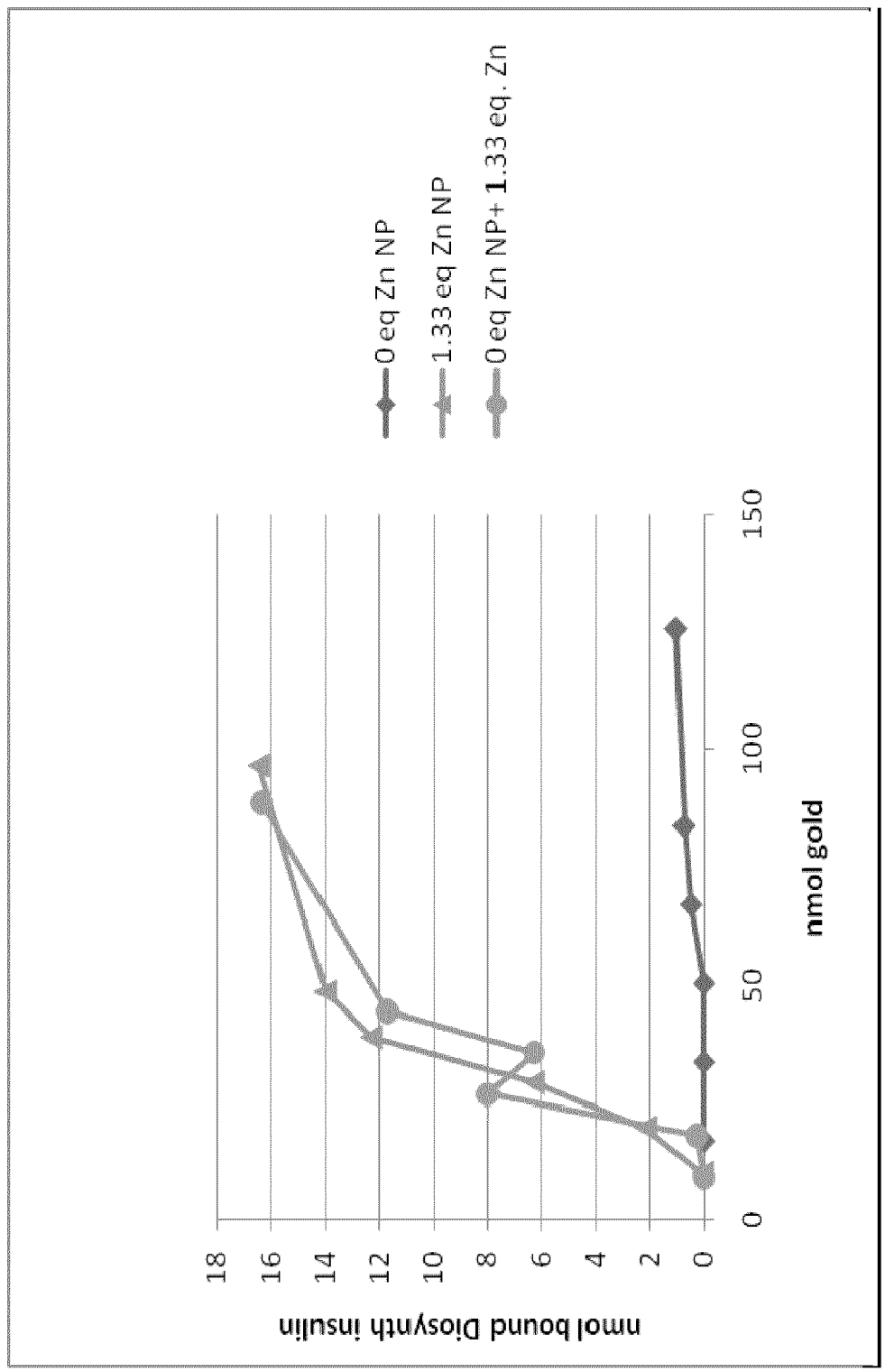
FIG. 17 shows a graph of insulin bound to gold nanoparticles, wherein diamonds indicate nanoparticles in the absence of zinc, triangles indicate nanoparticles synthesized in the presence of 1.33 equivalents of zinc, and circles indicate nanoparticles synthesized in the absence of zinc to which 1.33 equivalents of zinc have been added post-synthesis.

The results are shown in FIG. 17. FIG. 17 displays a Graph showing the amount of fixed 17.2 nmoles of Insulin binding to varying gold NP concentrations. Comparison of NP synthesised without Zn, a NP with synthesised with 1.33 eq, and Zn free NPs with 1.33 eq of ZnCl2.

The graph in FIG. 17 shows that with no zinc present insulin binding is at a very low level. When zinc is present insulin binding is significantly higher up to quantitative. Equivalent insulin binding occurs whether the zinc is present during NP synthesis or whether it is added post synthesis.

Without wishing to be bound by any theory, the present inventors believe that the $Zn^{2+}$ cation provides improved insulin binding to the gold NPs. Other forms of Zn, such as ZnO may also mediate improved insulin binding. In particular, presence of ZnO in gold NP sample that had been stored for a period of months indicates that ZnO can form and may additionally or alternatively to $Zn^{2+}$ cation mediate or facilitate improved insulin binding to the NPs.

The importance of $Zn^{2+}$ in insulin crystallisation, form and function has been reported previously. However, data described herein indicate that insulin bound to NPs, including in the presence of $Zn^{2+}$, is in monomeric or dimeric form rather than the hexameric form more commonly associated with human insulin in the presence of $Zn^{2+}$ (i.e. insulin not bound to NPs). This may present a considerable advantage in relation to the present invention because monomeric or dimeric insulin is preferred in many settings (e.g. clinical settings) as compared with hexameric insulin.

The present inventors have found that binding of GLP-1 to gold NPs (described herein) takes place the presence of Zn (including, but not limited to $Zn^{2+}$ and/or ZnO). GLP-1 binding to gold NPs described herein was to NPs synthesised in the presence of Zn. It is specifically contemplated herein that Zn may be present in GLP-1-bound gold nanoparticle compositions.

Example 6

GLP-1 Binding to Gold Nanoparticles

Figure 18:
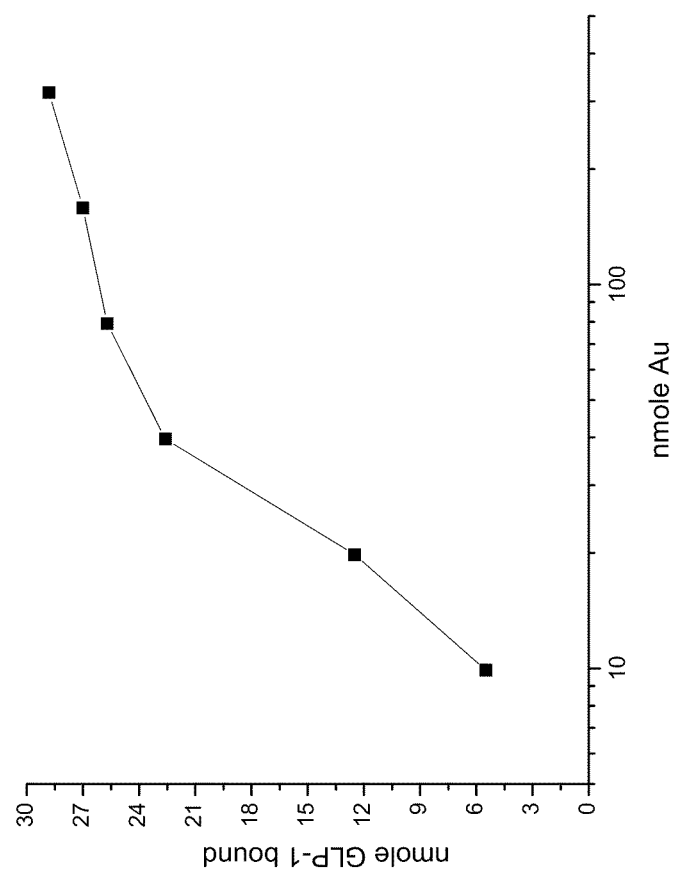
FIG. 18 shows binding of GLP-1 to gold nanoparticles at varying amounts of gold nanoparticles.

Gold nanoparticles (NPs), alphaGal(1) EG6NH2(1) NPs, were prepared as described in Example 2 above. Rather than adding insulin, GLP-1 was added. It was found that GLP-1 binds to the NPs. The binding of a fixed 29.8 nmoles of GLP-1 to varying gold NP concentrations is shown in FIG. 18. These results demonstrate that a peptide other than insulin binds to the nanoparticles of the invention.

Example 7

Figure 19:
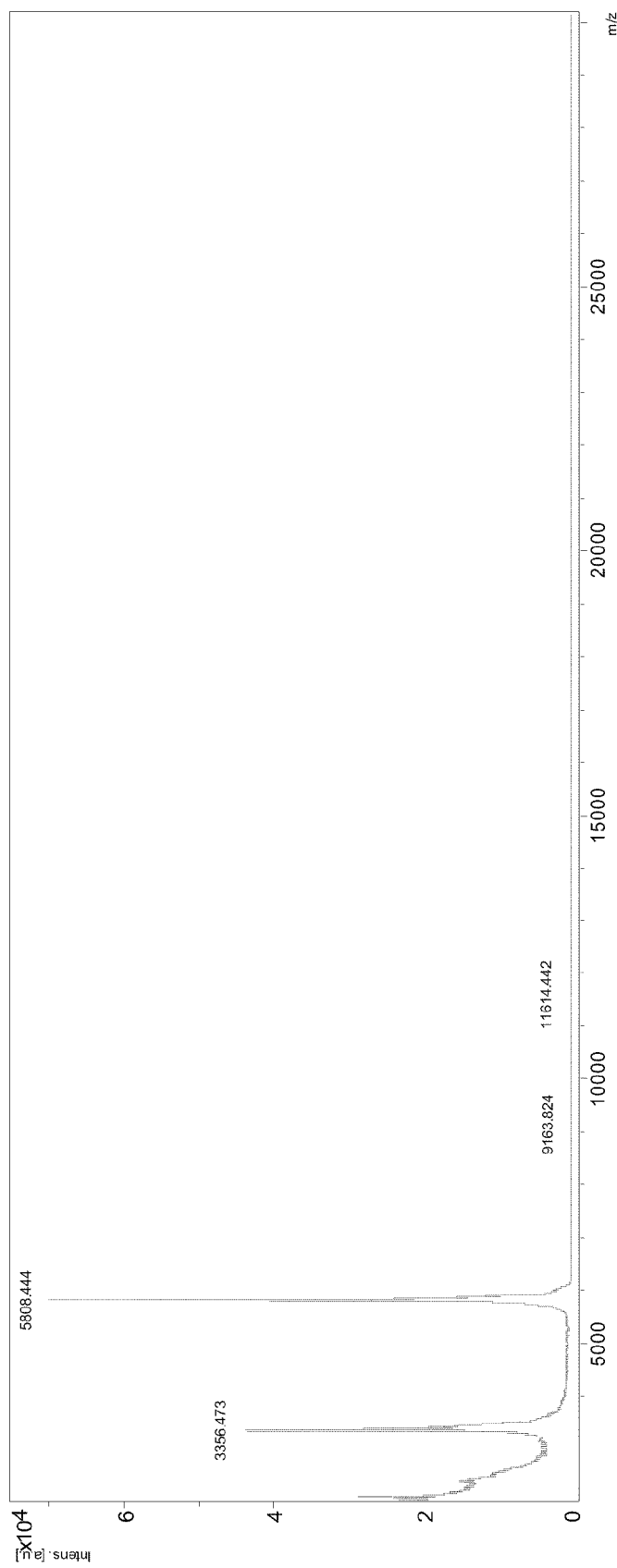
FIG. 19 shows a MALDI trace showing GLP-1 and insulin from a nanoparticle preparation comprising both GLP-1 and insulin.
Figure 20:
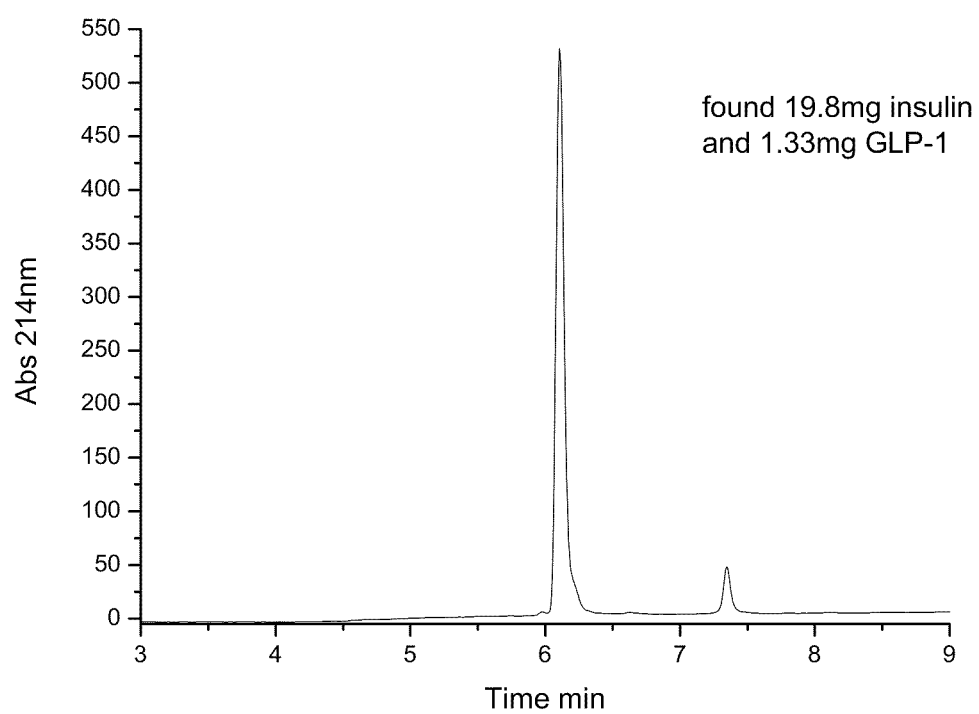
FIG. 20 shows an HPLC trace showing GLP-1 and insulin from a nanoparticle preparation comprising both GLP-1 and insulin.

Nanoparticles Co-Binding More than One Protein: Mixed Insulin/GLP-1 Nanoparticles Gold nanoparticles (NPs), alphaGal(1) EG6NH2(1) NPs, were prepared as described in Example 2 above. Insulin and GLP-1 were both added to the NPs. An aqueous solution of the GLP-1/Insulin NPs was subjected to analysis by MALDI and the results are shown in FIG. 19. The GLP-1/Insulin NPs were subjected to HPLC and the trace is shown in FIG. 20. The HPLC data show that 19.8 mg of insulin was measured and 1.33 mg of GLP-1.

The binding reaction was performed using a mixture of 26.2 mg insulin and 1.8 mg GLP-1. The HPLC data show that the approximate ratio of insulin:GLP-1 is maintained on binding to the nanoparticles.

The MALDI and HPLC data demonstrate the mixed binding of GLP-1 and Insulin to gold nanoparticles. Without wishing to be bound by any theory, the present inventors believe that co-binding of two or more different species of peptide to the nanoparticle of the invention may be preferred in certain settings (e.g. certain clinical settings) as compared with binding of a single species of peptide. In particular, combinations of peptides may be carried on a nanoparticle such that the peptides perform mutually beneficial functions and/or act in concert, such as in a synergistic fashion.

Examples 8-16

Production and Characterisation of Oral Film Incorporating Insulin Nanoparticles (Insulin NP)

Example 8

Insulin Film Strips (0.01 mg) for Assay Measurement and Placebo Strips

The following film composition was prepared and film strips made therefrom. One portion of the film strips (about 50 strips) were used as placebo samples for later testing. Another portion of the film strips contained 0.01 mg insulin nanoparticles (insulin NP), prepared as described herein. The insulin NP-containing strips were tested, as discussed below, to determine the stability of the insulin, i.e., that it remained biologically active, after drying of the film and standby at room temperature for two (2) months.

Film Matrix Composition
1. 4.796 g (7.993%) Polyethylene oxide (PEO) WSR 1105 LEO (Colorcon)
2. 26.977 g (44.961%) PEO WSR N80 LEO (Colorcon)
3. 11.99 g (19.983%) PEO WSR N10 LEO (Dow)
4. 7.993 g of Maltitol syrup (Lycasin 80/55) containing 5.995 g (9.991%) solids and 1.998 g water (Roquette)
5. 5.995 g (9.991%) Natural Glycerin (Spectrum)
6. 4.196 g (6.994%) HPMC E15 (Dow)
7. 0.072 g MED 341 Simethicone Emulsion (Nusil) containing 0.0444 g (0.074%) Simethicone
8. 176.802 g Sterile Water USP (Braun)
(Note: The remaining 0.013% of solids containing nanoparticles and insulin will be added later in the experiment)

Components 1, 4, 5, 7, and 8 were added to a fabricated glass bowl. The bowl was equipped with a variac controlled heating mantel and the heat was turned on. The solution was prepared as described below using the Degussa Dental Multivac Compact.

| | | |
|---|---|---|
| 20 minutes | stirring = 125 rpm | vacuum = 0% |
| Temperature = 67 C. | | |
| 40 minutes | stirring = 125 rpm | vacuum = 0% |
| Temperature = 63 C., cut off heat, and removed heating mantel | | |
| 20 minutes | stirring = 125 rpm | vacuum = 0% |
| Temperature = 35 C. | | |
| Added a blend of Ingredients of 2, 3, and 6 | | |
| Added sterile water to obtain QS | | |
| 20 minutes | stirring = 125 rpm | vacuum = 60% (16 in Hg) |
| 8 minutes | stirring = 100 rpm | vacuum = 80% (23 in Hg) |
| 8 minutes | stirring = 100 rpm | vacuum = 85% (24 in Hg) |
| 8 minutes | stirring = 100 rpm | vacuum = 90% (25 in Hg) |
| 8 minutes | stirring = 100 rpm | vacuum = 95% (26 in Hg) |
| 4 minutes | stirring = 100 rpm | vacuum = 98% (27 in Hg) |
| Added sterile water to obtain QS | | |
| 4 minutes | stirring = 100 rpm | vacuum = 98% (27 in Hg) |
| 4 minutes | stirring = 100 rpm | vacuum = 100% (28 in Hg) |

The solution was cast into 4 sheets of film using the a K-Control Coater with the micrometer wedge bar set at 840 microns onto mylar substrate to obtain placebo samples. The films were dried 25 minutes in an 80° C. convection air oven. The films were dried in accordance with the present invention. The films were dried in a manner where the air flow was sufficiently low such that it did not disturb the top surface or skin-over the surface of the film prior to formation of a visco-elastic matrix, which occurred in about 2-6 minutes and which locked-in the insulin NP in place such that uniformity of content was preserved. The films were cut into 22×26 mm strips which weighted ~94 to 107 mg and had a % moisture of 2.89. Fifty of these placebo strips were sealed individually in RFE-042 pouches and labeled.

119.4 g of the solution containing 29.996 g (99.987% of the solids) were left in the glass bowl after preparing the placebo strips. Then 600 micro liters of a solution containing insulin NP (gold galactose amine nanoparticle bovine insulin) containing 0.003 g (0.01%) insulin and 0.0009 g (0.003%) nanoparticles was added to the bowl. The solution was allowed to stir for 16 minutes at 100 rpm at a vacuum of 100% (28 in Hg) using the Degussa Dental Multivac Compact. The film was cast into six sheets of film using the K-Control Coater with a micrometer setting of 845 microns onto mylar substrate. Two films were dried at 60° C. for 40 minutes, two films were dried at 40° C. for 80 minutes, and two films were dried at room temperature for 19 hours. Drying was again performed to retain and preserve uniformity of content as described herein. The films were cut into 22×26 mm strips which weighed ~94 to 114 mg. The strips were sealed individually in RFE-042 pouches. Fifty strips at each drying condition were obtained. The strips dried at 60° C. and dried at 40° C. were labeled. The strips dried at room temperature were also labeled.

Immunoenzymatic assay measurements using absorbance measurements indicated that the insulin was stable after drying at room temperature, 40° C., and 60° C. After allowing strips dried at 60° C. to stand for 2 months at room temperature, the strips were still biologically active.

Example 9

Insulin Film Strips (1 IU) for First Mice Study and Placebo (Deposition Method of Adding NP-Insulin Solution) (In Situ Solution Method of Adding NP-Insulin)

Objective:

Manufacturing of insulin strips and demonstration of unaffected insulin bio-activity following the manufacturing process by intra-peritoneal (IP) injection in streptozotocin-treated, diabetic mice.

Film Matrix Composition
1. 4.796 g (7.993%) Polyethylene oxide (PEO) WSR 1105 LEO (Colorcon)
2. 26.984 g (44.974%) PEO WSR N80 LEO (Colorcon)
3. 11.99 g (19.983%) PEO WSR N10 LEO (Dow)
4. 7.993 g of Maltitol syrup (Lycasin 80/55) containing 5.995 g (9.991%) solids and 1.998 g water (Roquette)
5. 5.995 g (9.991%) Natural Glycerin (Spectrum)
6. 4.196 g (6.994%) HPMC E15 (Dow)
7. 0.072 g MED 341 Simethicone Emulsion (Nusil) containing 0.0444 g (0.074%) Simethicone
8. 177.982 g Sterile Water USP (Braun)

Components 1, 4, 5, 7, and 8 were added to a fabricated glass bowl. The bowl was equipped with a variac controlled heating mantel and the heat was turned on. The solution was prepared as described below using the Degussa Dental Multivac Compact.

| | | |
|---|---|---|
| 20 minutes | stirring = 125 rpm | vacuum = 0% |
| Temperature = 67 C. | | |
| 40 minutes | stirring = 125 rpm | vacuum = 0% |
| Temperature = 63 C., cut off heat, and removed heating mantel | | |
| 20 minutes | stirring = 125 rpm | vacuum = 0% |
| Temperature = 35 C. | | |
| Added a blend of components of 2, 3, and 6 | | |
| Added sterile water to obtain QS | | |
| 20 minutes | stirring = 125 rpm | vacuum = 60% (16 in Hg) |
| 8 minutes | stirring = 100 rpm | vacuum = 80% (23 in Hg) |
| 8 minutes | stirring = 100 rpm | vacuum = 85% (24 in Hg) |
| 8 minutes | stirring = 100 rpm | vacuum = 90% (25 in Hg) |
| 8 minutes | stirring = 100 rpm | vacuum = 95% (26 in Hg) |
| Added 2% of Span 80 (Spectrum) by weight to the solids to reduce entrapped air | | |
| 8 minutes | stirring = 100 rpm | vacuum = 95% (26 in Hg) |

The solution was cast into four films using the K-Control Coater with the micrometer adjustable wedge bar set at 860 microns onto mylar substrate to obtain placebo samples. The films were dried 25 minutes in an 80 C. convection air oven. Drying was conducted in a controlled manner in accordance with the invention to prevent top disturbance of the top surface and to prevent skimming prior to drying the depth of the film and to develop a visco-elastic matrix within the first six (6) minutes. The formation of the visco-elastic matrix locked-in the insulin NP such that they could not migrate and resulted in uniformity of content in the film and in the unit doses cut therefrom.

The films were cut into 22.2×25.4 mm strips which weighed 93 to 113 mg. Fifty of these placebo strips were sealed individually in RFE-042 pouches and were labeled. Forty of the placebo strips (films) were saved for the below insulin deposition experiment.

Ten micro liters of NP-5-Insulin solution (human insulin) prepared in accordance with the invention were added to each of the forty placebo strips dot by dot using a 5 micro liter pipette. The strips were dried for 2 hours at room temperature, were sealed individually in RFE-042 pouches and were labeled. This demonstrates the feasibility of adding the NP-Insulin solution by the deposition method directly onto the film.

120 g of the original solution were placed in a fabricated glass bowl. Then 2600 micro liters of the NP-5-insulin solution (target was for 3015 micro liters) were added to the bowl. Due to inadequate amount of NP-5-insulin solution, the strip dry target weight was adjusted from 100 mg to 117 mg to obtain 1 IU of insulin per film strip. The solution was deairated with stirring. The solution was cast into 6 film sheets using the K-Control Coater with the micrometer adjustable wedge bar set at 1000 to 1025 microns onto mylar substrate. Two films were dried at 60 C. for 29 to 37 minutes, two films were dried at 80 C. for 28 minutes, and two films were dried at 100 C. for 20 minutes. Drying was conducted in accordance with the invention (as is was for all examples), i.e., controlled drying was performed to develop a viscoelastic matrix and lock-in the insulin NP such that the particles could not migrate and that uniform content was achieved. Air flow was controlled to prevent disturbance of the film surface and premature skinning (prior to drying the depth of the film). Once the viscoelastic matrix was formed, further drying was conducted to ensure the desired water content level was attained. The films were cut into 22.2×25.4 mm strips which weighed 108 to 125 mg. The strips were sealed individually in RFE-042 pouches. Forty to forty two strips at each drying condition were obtained. The strips dried at 60 C. were labeled, the strips dried at 100° C. and were labeled, and the strips dried at 80° C. and were also labeled. This experiment demonstrates the feasibility of adding the NP-Insulin solution in situ with the film solution prior to casting film.

Due to a shortage of mice for the study at, the strips dried at 80° and 100° C. were not tested. Nanoparticles (NP) with human insulin attached were active in lowering blood glucose to normoglycaemic values in diabetic mice. The activity remained at 400 minutes. The data indicates that nanoparticle bound human insulin does not rapidly dissociate from the nanoparticles and provides a continuous delivery of insulin, in contrast to pure insulin which has a short activity span. The strips with NP-5-insulin attached and manufactured at 60° C. were able to reduce blood glucose to normoglycaemic levels. The manufacturing process and temperature did not affect bioactivity of insulin bound to nanoparticle indicating that the insulin is stabilized when bound. The nanoparticle appears to be critical in heat stabilization of the insulin during this process.

Example 10

Insulin Film Strips (1 IU) Slow Dissolving Formula

Film Matrix Composition
1. 1.959 g (7.834%) Polyethylene oxide (PEO) WSR 1105 LEO (Colorcon)
2. 11.017 g (44.067%) PEO WSR N80 LEO (Colorcon)
3. 4.896 g (19.585%) PEO WSR N10 LEO (Dow)
4. 3.264 g Maltitol Syrup (Lycasin 80/55) (Roquette) containing 2.448 g (9.793%) solids and 0.816 g Water
5. 2.448 g (9.793%) Natural Glycerin (Spectrum)
6. 1.714 g (6.854%) HPMC E15 (Dow)
7. 0.03 g MED 341 Simethicone Emulsion (Nusil) containing 0.0185 g (0.074%) Simethicone
8. 0.50 g (2.000%) Span 80 (Spectrum)
9. 71.684 g Sterile Water USP (McGaw)

Components 4, 5, 7, 8, and 9 were added to a fabricated glass bowl. Then component 1 was added slowly to the bowl while stirring with a spatula. The bowl was equipped with a variac controlled heating mantel and the heat was turned on. The solution was prepared as described below using the Degussa Dental Multivac Compact.

| 8 minutes | stirring = 125 rpm | vacuum = 0% |
|---|---|---|
| Temperature = 84 C. | | |
| 40 minutes | stirring = 125 rpm | vacuum = 0% |
| Cut off heat and removed the heating mantel | | |
| Added sterile water to obtain QS | | |
| Added a blend of Ingredients 2, 3, and 6 | | |

-continued

| 20 minutes | stirring = 125 rpm | vacuum = 60% (16 in Hg) |
|---|---|---|
| 20 minutes | stirring = 100 rpm | vacuum = 90% (25 in Hg) |
| 12 minutes | stirring = 100 rpm | vacuum = 95% (27 in Hg) |
| 8 minutes | stirring = 100 rpm | vacuum = 98% (27.5 in Hg) |
| Added sterile water to obtain QS | | |
| 4 minutes | stirring = 100 rpm | vacuum = 100% (28.5 in Hg) |

48.75 g of this solution was added to a fabricated glass bowl. Then 1.25 ml of NP-6-Insulin containing 125 IU insulin (yields 1 IU per strip) were added to the bowl. This solution was stirred for 4 minutes at 100 rpm and vacuum=100% (28.5 in Hg) using the Degussa Dental Multivac Compact. This solution was cast into 2 sheets of film using the K-Control Coater with the micrometer adjustable wedge bar set at 865 microns onto the HDP side of paper substrate. The film sheets were dried in a 60° C. convection air oven for 40 minutes. Drying was conducted in accordance with the invention as described in prior examples to produce uniformity of content in the resultant film and unit doses cut therefrom. The films were cut into 22.2×25.4 mm strips which weighed 93 to 110 mg. The film had a moisture content of 1.92%. Fifty four strips were sealed individually in RFE-042 pouches and were labeled.

Example 11

Insulin Film Strips (1 IU) (Fast Formula Dried at 60° C. and 100° C. for Second Mice Study)

Film Matrix Composition
1. 5.171 g (49.25%) Polyethylene oxide (PEO) WSR N10 LEO (Dow)
2. 2.586 g (24.63%) HPMC E15 (Dow)
3. 1.724 g Maltitol Syrup (Lycasin 80/55) (Roquette) containing 1.293 g (12.31%) solids and 0.431 g Water
4. 1.293 g (12.31%) Natural Glycerin (Spectrum)
5. 0.053 g (0.50%) Span 80 (Spectrum)
6. 0.105 g (1.00%) Titanium Dioxide USP (Brenntag)
7. 3.0 ml of NP-6-insulin containing 300 IU insulin (yields 1 IU per strip (Midatech)
8. 14.069 g Sterile Water USP (McGaw)

Components 3, 4, 5, 6, and 8 were added to a fabricated glass bowl. Then a blend of components 1 and 2 were added to the bowl. The solution was prepared as described below using the Degussa Dental Multivac Compact.

| 40 minutes | stirring = 100 rpm | vacuum = 60% (16 in Hg) |
|---|---|---|
| 40 minutes | stirring = 100 rpm | vacuum = 90% (25 in Hg) |
| 12 minutes | stirring = 100 rpm | vacuum = 95% (27 in Hg) |
| 8 minutes | stirring = 100 rpm | vacuum = 98% (27.5 in Hg) |
| Added sterile water to obtain QS | | |
| 4 minutes | stirring = 100 rpm | vacuum = 100% (28.5 in Hg) |
| Added component 7 | | |
| Added sterile water to obtain QS | | |
| 8 minutes | stirring = 100 rpm | vacuum = 100% (28.5 in Hg) |

The solution was cast into 2 sheets of film using the K-Control Coater with the micrometer adjustable wedge bar set at 440 to 460 microns onto the HDP side of paper substrate. One film was dried 15 minutes at 100° C. in a convection air oven and the other film was dried 30 minutes at 60° C. in a convection air oven. Drying was done in accordance with the invention to produce uniformity of content in the resultant film and unit doses cut therefrom. The films were cut into 0.875×0.5 inch strips which weighed 33 to 39 mg. Fifty five strips were obtained at each drying condition. The strips were sealed individually in RFE-042 pouches. The strips dried at 100° C. and the strips dried at 60° C. were both labeled.

Example 12

Fast Dissolving Film Strips Placebo Formula for Second Mice Study

Film Matrix Composition 1. 18.469 g (49.25%) Polyethylene oxide (PEO) WSR N10 LEO (Dow)
2. 9.236 g (24.63%) HPMC E15 (Dow)
3. 6.155 g Maltitol syrup (Lycasin 80/55) (Roquette) containing 4.616 g (12.31%) solids and 1.539 g Water
4. 4.616 g (12.31%) Natural Glycerin (Spectrum)
5. 0.188 g (0.50%) Span 80
6. 0.375 g (1.00%) Titanium Dioxide USP (Brenntag)
7. 60.961 g Distilled Water Components 3, 4, 5, 6, and 7 were added to a fabricated glass bowl. Then a blend of components 1 and 2 were added to the bowl. The bowl was equipped with a variac controlled heating mantle and the heat was turned on. The solution was prepared as described below using the Degussa Dental Multivac Compact.

| | | |
|---|---|---|
| 12 minutes stirring = 125 rpm | vacuum = 0% | |
| Temperature = 85° C. | | |
| Cut off heat and removed the heating mantel | | |
| 20 minutes stirring = 125 rpm | vacuum = 0% | |
| Added distilled water to obtain QS | | |
| 20 minutes stirring = 125 rpm | vacuum = 60% (16 in Hg) | |
| 20 minutes stirring = 125 rpm | vacuum = 90% (25 in Hg) | |
| 12 minutes stirring = 100 rpm | vacuum = 95% (27 in Hg) | |
| 8 minutes stirring = 100 rpm | vacuum = 98% (27.5 in Hg) | |
| Added sterile water to obtain QS | | |
| 4 minutes stirring = 100 rpm | vacuum = 100% (28.5 in Hg) | |
| Added sterile water to obtain QS | | |
| 8 minutes stirring = 100 rpm | vacuum = 100% (28.5 in Hg) | |

The solution was cast into films using the K-Control Coater with the micrometer adjustable wedge bar set at 440 microns onto mylar substrate. The films were dried 25 minutes in an 80° C. convection air oven. Drying was done in accordance with the invention to produce uniformity of content in the resultant film and unit doses cut therefrom. The film had a moisture content of 4.42%. The films were cut into 0.875×0.5 inch strips which weighed ~35 to 36 mg. The film had adequate tensile strength, had low to moderate tear resistance, and had adequate flexibility when the properties were evaluated subjectively. A 36 mg film strip had a Partial Immersion Dissolution (PID) at 37.2 C. of 5 seconds. (The PID is an in house technique used to give an estimate of the time taken for the film to break when exposed to water with a 2.8 g weight attached.)

Experience from prior research projects has shown that a PID of 5 to 10 seconds corresponds to a dissolution time in the mouth of 1 minute or less.

Sixty of the film strips were sealed in the bulk in foil and were labeled to be used as placebo's for the I IU strips of insulin in the fast formula for the second mice study (prepared in Example 8).

Example 13

Preparation of Slow Dissolving Occlusive Film Strips for the Mini Pig Study

Film Matrix Composition 1. 7.844 g (7.47%) Polyethylene oxide (PEO) WSR 1105 LEO (Colorcon)
2. 53.981 g (51.41%) PEO WSR N80 LEO (Colorcon)
3. 17.011 g Maltitol Syrup (Lycasin 80/55) (Roquette) containing 12.758 g (12.15%) solids and 4.253 g Water
4. 12.758 g (12.15%) Natural Glycerin (Spectrum)
5. 10.805 g (10.29%) HPMC E15 (Dow)
6. 2.10 g (2.00%) Sucralose
7. 4.20 g (4.00%) Peppermint 2303 Flavor (Ungerer)
8. 0.525 g (0.50%) Glyceryl Monooleate (Spectrum)
9. 0.0315 g (0.03%) Blue #1
10. 240.747 g Sterile Water (Braun)

Components 3, 4, 8, and 10 were added to a fabricated glass bowl. Then component 1 was added to the bowl while stirring with a spatula. The bowl was equipped with a variac controlled heating mantel and the heat was turned on. The solution was prepared as described below using the Degussa Dental Multavac Compact.

| | | |
|---|---|---|
| 20 minutes stirring = 150 rpm | vacuum = 0% | |
| 40 minutes stirring = 150 rpm | vacuum = 0% | |
| Cut off heat and removed heating mantel | | |
| Added a blend of components 2, 5, 6, and 9 | | |
| Added sterile water to obtain QS | | |
| 20 minutes stirring = 125 rpm | vacuum = 60% (17 in Hg) | |
| 20 minutes stirring = 100 rpm | vacuum = 90% (26 in Hg) | |
| 12 minutes stirring = 100 rpm | vacuum = 95% (27 in Hg) | |
| 8 minutes stirring = 100 rpm | vacuum = 98% (28 in Hg) | |
| Added sterile water to obtain QS | | |
| Added component 7 | | |
| 8 minutes stirring = 100 rpm | vacuum = 100% (28.5 in Hg) | |

The solution was cast into film using the K-Control Coater with the micrometer adjustable wedge bar set at 900 microns onto the non glossy HDPE side of 6330L paper substrate. The film was dried 27 minutes in an 80° C. convection air oven. Drying was done in accordance with the invention to produce uniformity of content in the resultant film and unit doses cut therefrom. A 22×11 mm strip of the film weighed 51 mg. A 22×11 strip of the film had a partial immersion dissolution rating (PID) at 37.2 C. of 18 seconds and lasted approximately 13.5 minutes in the buccal area of the mouth. The films were cut into 22×160 mm strips and were sealed in foil for use in the minipig study.

Example 14

Preparation of Fast Dissolving MI-NP-10-Insulin Film Strips for Mini Pig Study

The primary aims of this study were to test whether buccal preparations of insulin carried by gold nanoparticles embedded in the film matrix would reach systemic concentrations suitable for a therapeutic response and to determine the absorption of insulin through the buccal mucosa in order to establish an appropriate dose to be further investigated in humans.

Preparation of Insulin Gold Nanoparticles:
a) A solution of gold nanoparticles MI-NP-10-INS (13.041 mg gold) was made up to 49.68 mL of water.

Acetic acid was added to the final solution to obtain a pH=4.6.

55.7 mg of human insulin in 27.85 mL of Tris.HCl pH 7.5 was added.

The suspension was left 24 hours and after this time, was centrifuged 1 minute at 4500 g.

The supernatant was removed and stored for further insulin and gold content analysis. The precipitate was re-suspended in 3.220 mL of water to obtain a final insulin concentration of 500 units insulin/mL.

The size distribution of the insulin-gold nanoparticles was determined by DLS analysis. The insulin content was determined by BCA standard assay.

The final preparation of insulin gold NP was performed under laminar flow cabinet. All glass and plastic material and solvents used were autoclaved. All disposables are supplied pre-sterilized.

b) Insulin content:
The % of insulin binding to the nanoparticles was determined by the following formula:

$$\% \text{ insulin} = \frac{\text{insulin added} - \text{insulin supernatant}}{\text{insulin added}} \times 100$$

TABLE 3

| Sample | Insulin content | | | |
| --- | --- | --- | --- | --- |
| | Insulin added (mg) | Insulin supernatant (mg) | Insulin bound (mg) | % insulin bound |
| MI-NP-10 insulin | 55.700 | 1.308 | 54.4 | 97.65 |

Analysis Summary
Insulin: 54.4 mg Insulin
Gold: 13.041 mg of gold
Total volume: 3.23 mL water
Final insulin concentration: 16.8 mg insulin/mL=488 units/mL
Final gold concentration: 4.037 mg Au/mL.

c) Preparation of the Film Matrix Composition
1. 14.775 g (49.25%) PEO WSR N10 LEO (Colorcon)
2. 7.389 g (24.63%) HPMC E15 (Dow)
3. 4.924 g Maltitol syrup (Lycasin 80/55) (Roquette) containing 3.693 g (12.31%) solids and 1.231 g water
4. 3.693 g (12.31%) Natural Glycerin (Spectrum)
5. 0.15 g (0.50%) Glyceryl Monooleate (Spectrum)
6. 0.30 g (1.00%) Titanium dioxide (Brenntag)
7. 53.769 g Sterile water (Braun)

Components 3, 4, 5, 6, and 7 were added to a fabricated glass bowl. Then a blend of components 1 and 2 were added to the bowl. The solution was prepared as described below using the Degussa Dental Multivac Compact.

| 40 minutes | stirring = 100 rpm | vacuum = 60% (17 in Hg) |
| --- | --- | --- |
| 40 minutes | stirring = 100 rpm | vacuum = 90% (26 in Hg) |
| 12 minutes | stirring = 100 rpm | vacuum = 95% (27 in Hg) |
| 8 minutes | stirring = 100 rpm | vacuum = 98% (28 in Hg) |
| Added sterile water to obtain QS | | |
| 4 minutes | stirring = 100 rpm | vacuum = 100% (28.5 in Hg) |

Seventeen grams of this solution containing 6 grams of solids were added to a smaller fabricated bowl. Then 3 ml of MI-NP-10-Insulin containing 1500 IU insulin (Midatech) were added to the bowl. The solution was stirred 10 minutes at 125 rpm and vacuum=100% (28.5 in Hg) using the Degussa Dental Multivac Compact. The solution was cast into film using the K-Control Coater with the micrometer adjustable wedge bar set at 365 microns onto the non glossy HDPE side of 6330L paper. The film was dried 20 minutes in an 80° C. convection air oven. Drying was done in accordance with the invention to produce uniformity of content in the resultant film and unit doses cut therefrom. The film had a moisture content of 3.33. The film was cut into 7×18 mm strips which weighed 9 to 11 mg. The dry strip target weight was 10 mg with an acceptable weight range to yield+/−10% of target of 9 to 11 mg. The dosage of insulin per strip is 2.5 IU. The strips had a PID of 3 seconds. Ten foil pouches containing 2 strips at 2.5 IU insulin per strip or 5 IU insulin per pouch were labeled. Also ninety of the single strips containing 2.5 IU per strip were packaged in the bulk and were labeled.

Example 15

Lamination of the Fast Dissolving Insulin Film Strip onto the Slow Dissolving Occlusive Film Fast Dissolving Film Matrix Composition
Film strips (7×18 mm) of the fast dissolving insulin film made in Example 14 above were centered on strips (11×22 mm) of the slow dissolving occlusive film made in Example 10 above. The film strips were laminated by allowing the strips to pass twice through the GBC Heat Sealer H212 using a heat setting of 3.

Twenty four foil pouches containing 2 laminated strips at 2.5 IU insulin per strip or 5 IU insulin per pouch were labeled. The laminated films of this example were sent for use in the mini pig study:
Twenty Four foil pouches containing 2 laminated strips at 2.5 IU insulin per strip or 5 IU insulin per pouch.

Example 16

Preparation of Fast Dissolving Placebo Film Strips and Lamination to the Slow Dissolving Occlusive Film Stips for the Minipig Study Fast Dissolving Film Composition
1. 14.775 g (49.25%) PEO WSR N10 LEO (Colorcon)
2. 7.389 g (24.63%) HPMC E15 (Dow)
3. 4.924 g Maltitol syrup (Lycasin 80/55) (Roquette) containing 3.693 g (12.31%) solids and 1.231 g water
4. 3.693 g (12.31%) Natural Glycerin (Spectrum)
5. 0.15 g (0.50%) Glyceryl Monooleate (Spectrum)
6. 0.30 g (1.00%) Titanium dioxide (Brenntag)
7. 68.769 g Distilled water Components 3, 4, 5, 6, and 7 were added to a fabricated glass bowl. Then a blend of components 1 and 2 were added to the bowl. The solution was prepared as described below using the Degussa Dental Multivac Compact.

| 40 minutes | stirring = 100 rpm | vacuum = 60% (17 in Hg) |
| --- | --- | --- |
| 40 minutes | stirring = 100 rpm | vacuum = 90% (26 in Hg) |
| 12 minutes | stirring = 100 rpm | vacuum = 95% (27 in Hg) |
| 8 minutes | stirring = 100 rpm | vacuum = 98% (28 in Hg) |
| Added sterile water to obtain QS | | |
| 4 minutes | stirring = 100 rpm | vacuum = 100% (28.5 in Hg) |

The solution was cast into film using the K-Control Coater with the micrometer adjustable wedge bar set at 365 microns onto the non glossy HDPE side of 6330L paper. The film was dried 20 minutes in an 80° C. convection air oven. Drying was done in accordance with the invention to produce uniformity of content in the resultant film and unit doses cut therefrom. The moisture content of the film was 4.23% and the dry strip target weight was 10 mg.

Film strips (7×18 mm) of this fast dissolving placebo were centered on strips (11×22 mm) of the slow dissolving occlusive film strips made in Example 10. The strips were laminated by allowing to pass twice through the GBC Heat Sealer H212 using a heat setting of 3. Ten foil pouches containing 2 of the laminated placebo strips per pouch and were labeled.

Preparation of Negative and Positive Controls 2 solutions were prepared under flow laminar cabinet.
1. NEGATIVE CONTROL:
   To a solution sterile saline buffer (0.85% NaCl) 20 mL:
   Added:
   Phenol (40 μL, 0.2%) (Batch: 067K0765-Sigma-aldrich
   Bovine serum albumin (0.01 mg, 0.1%) (K40246318 936-Merck).
   The mix was stirred for 15 min, and then pH was adjusted to ~3 with 1N HCl. The solution was passed through a 0.22μ filter and filled in to a sterile 8 ml. vial and labelled.
2. POSITIVE CONTROL:
   To 10 mL of negative control (before to adjuste pH):
   Added
   Insulin (3.45 mg, 100 IU) (11 376 497 001-Roche).
   The mix was stirred for 15 min and the pH was adjusted to ~3.0 with 1N HCl.
   The solution was passed through a 0.22μ filter and filled in a sterile vial of 8 mL. The vial was then labelled.
3. Shipment for minipig study:
   a. 2 Vials Positive Control V=6 ml: Saline Buffer Insulin 0.06 mM
   b. 2 Vials Negative Control V=6 ml: Saline Buffer
   c. 10 Strips Placebo (Example 13)
   d. 24 Pouches Insulin MI-NP-10; each pouch contained 2 films and each film contained 2.5 IU insulin: (Example 12)

Protocol

Nanoparticle constructs that bind human insulin were synthesized as described above and were then incorporated into polymer filmstrip delivery systems. The film strips were dissolved in water and an aliquot was then injected into the peritoneal cavity of diabetic mice to test for biological activity. Following injection the blood glucose levels were monitored and the change in blood glucose plotted for each mouse.

Figure 22:
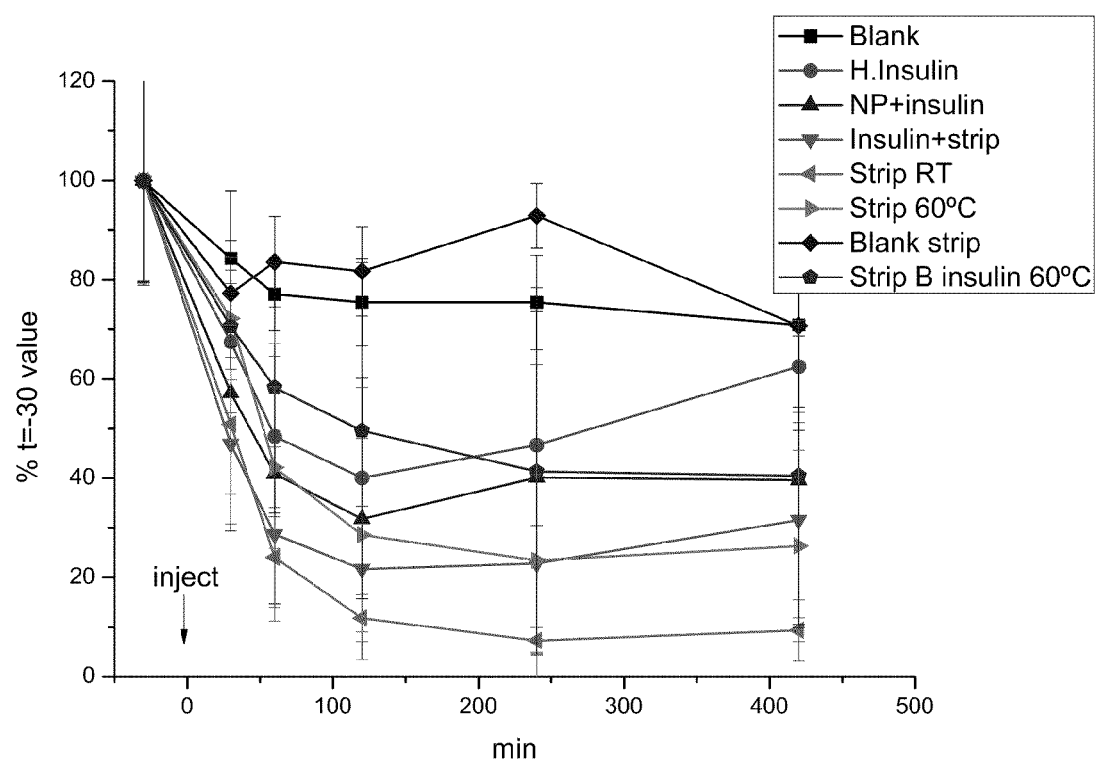
FIG. 22 shows plots of blood glucose levels in diabetic mice post-injection for the indicated injected samples and controls.

FIG. 22 shows the blood glucose levels plotted on a graph. Note that "IU"=International Unit. The following groups are plotted on the graph of FIG. 22:
Sample 1. Blank—water injection (Blank)
Sample 2. Pure human insulin at a dose of 1 IU/kg (H. insulin)
Sample 3. Pure human insulin attached to nanoparticles at dose of 1 IU/kg (NP-Insulin)
Sample 4. Human insulin (1 IU/kg) dissolved in solution from a blank strip. (Insulin plus strip from Example 13)
Sample 5. Human insulin attached to nanoparticles deposited on a blank strip at room temperature and then dissolved in water. (2 IU/kg) (Strip RT; NP-5-Insulin deposited on strips from Example 13.)
Sample 6. Human insulin attached to nanoparticles and manufactured into a strip at 60 degrees centigrade (1 IU/kg) and then dissolved in water. (Strip 60 (NP5-Insulin in strips))
Sample 7. Solution from a dissolved blank strip. (Blank strip; placebo film strip from Example 13)
Sample 8. Bovine insulin attached to a nanoparticle and manufactured into a strip at 60 degrees centigrade (1 IU/kg) and then dissolved in water. (Strip B; Bovine Insulin in Film Strips)

Conclusions on Samples 1-8

Controls
   Control (sample 1) shows that a water blank has no glucose lowering activity.
   Control (sample 2) shows that human insulin transiently dropped blood glucose to normoglycaemic values which then returned to hyperglycaemic values by 400 minutes.
   Control (sample 4) shows that the dissolved polymer formulation of the strips does not interfere with insulin activity.
   Control (sample 5) shows that nanoparticles containing human insulin that were deposited on strips (i.e. not incorporated into film) and shipped following production (shipping control) were still active.
   Control (sample 7) shows that the dissolved polymer blank from the strips had no glucose lowering activity.

Test Samples
   Sample 3 showed that nanoparticles with insulin attached were active in lowering blood glucose to normoglycaemic values. The activity remained at 400 minutes. Data indicate that nanoparticle-bound human insulin does not rapidly dissociate from the nanoparticles and provides a continuous delivery of insulin, in contrast to pure insulin which only has a short activity span.
   Sample 6 shows that nanoparticles with insulin attached and manufactured at 60 degrees centigrade were able to reduce blood glucose to normoglycaemic levels. The manufacturing process and temperature did not affect bioactivity of insulin bound to these nanoparticles indicating that insulin is stabilized when bound. Kinetics of activity was similar to sample 3 suggesting that the insulin is still bound to the nanoparticle after manufacture into a film at 60 degrees.
   Sample 8 shows that bovine insulin on nanoparticles and manufacture at 60 degrees centigrade and allowed to sit at room temperature for 2 months was still biologically active.

The above results confirm that it is possible to attach (or closely associated) human insulin to a nanoparticle and that the biological activity of the attached insulin is maintained during and after the manufacturing process. The data also suggests that the nanoparticle is critical in heat stabilization of the insulin during this process. The biological activity of the pure human insulin on a nanoparticle appears to be greater than for pure human insulin alone. Also the duration of action of the insulin nanoparticles is much longer than observed for pure human insulin. Pure human insulin has a tendency to form aggregates in solution and it is only the monomer forms of insulin that are active. These monomer forms are rapidly cleared by the kidney, and the effect of an injection of pure human insulin is normally over within 4 hours. The above results suggest that the insulin nanoparticle constructs are releasing insulin monomers slowly from the particle. By 400 minutes no loss of insulin activity was observed in the mice. However, the initial phase of activity was similar to pure human insulin. The nanoparticles release some insulin immediately (rapid acting) and then deliver a reserve of insulin. At 7 hours this reserve had not yet been depleted. Diabetic patients are normally given a mixture of rapid acting insulin (acts during first 6 hours) and slow acting insulin (starts after 6 hours and continues for up to 24 hours). Without wishing to be bound by any theory, it appears from this preliminary data that the insulin nanoparticles are behaving like a combination of fast and slow acting insulin. This kinetic behavior is also observed for the release of drugs from nanoparticles via glutathione (a rapid phase and then a slow release phase to 24 hours). It appears similar steric/chemical exchange mechanisms also apply to the release of peptides (insulin) from nanoparticles.

These results have significant implications for the use of nanoparticles for the delivery of peptides such as insulin using film delivery technology.

In Vivo Testing in Minipigs

A group of three minipigs were fasted overnight and then anaesthetized. They were then injected with 2 IU of Human insulin subcutaneously. A $4^{th}$ animal was used as a control and treated identically but injected with sterile buffer. Blood samples were taken at known intervals up to 180 minutes. Following this treatment the minipigs were given a one-week wash out period and the experiment repeated with the subcutaneous (sc) injection replaced with two polymer strips (Example 13) containing nanoparticles with coupled insulin at a concentration of 2.5 IU human insulin per strip for transbuccal (tb) administration. Blood samples were again taken at regular intervals up to a period of 180 minutes. Blood plasma was analysed for blood glucose levels, insulin and C-Peptide.

C-Peptide Levels

Figure 23A:
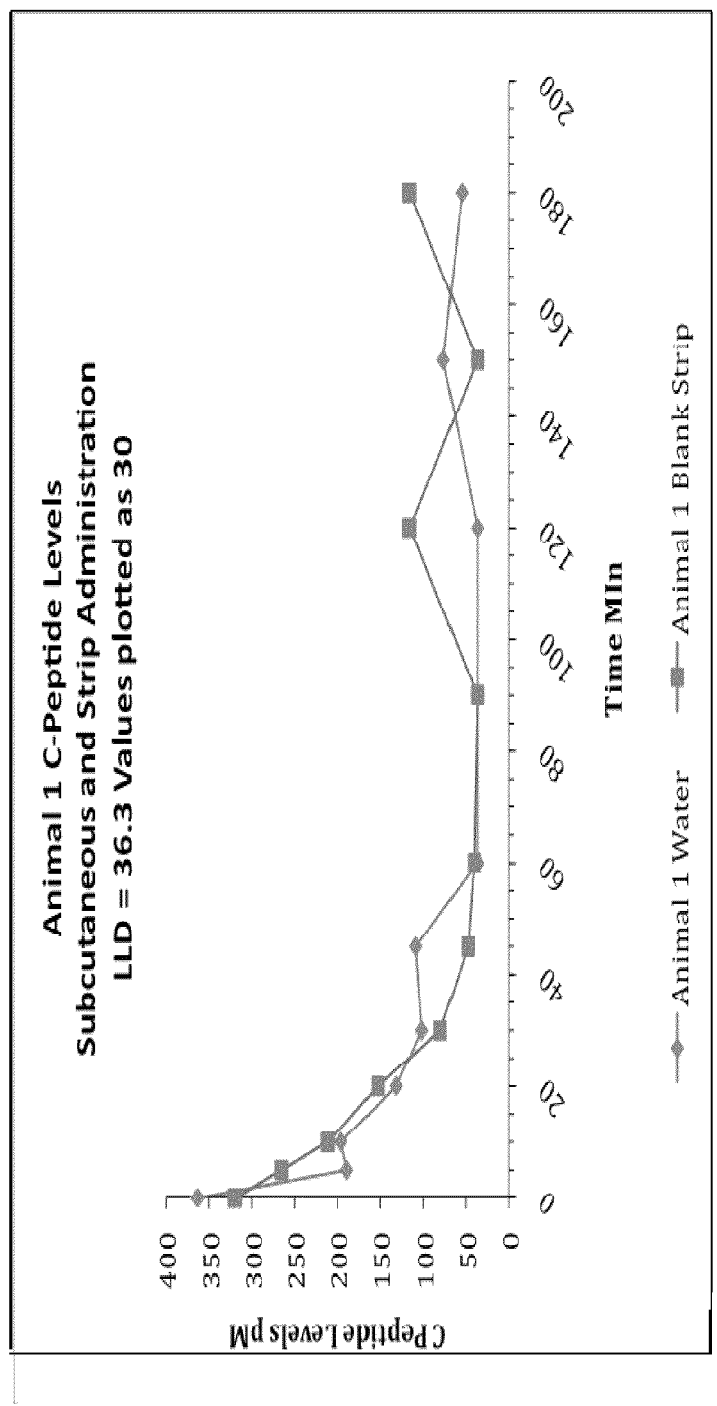
FIG. 23 shows A) plots of C-peptide levels over time for control minipig 1 following water (circles) and blank strip (squares) administration, B) plots of C-peptide levels over time for minipig 2 following subcutaneous (circles) and transbuccal (squares) administration of sample.
Figure 23B:
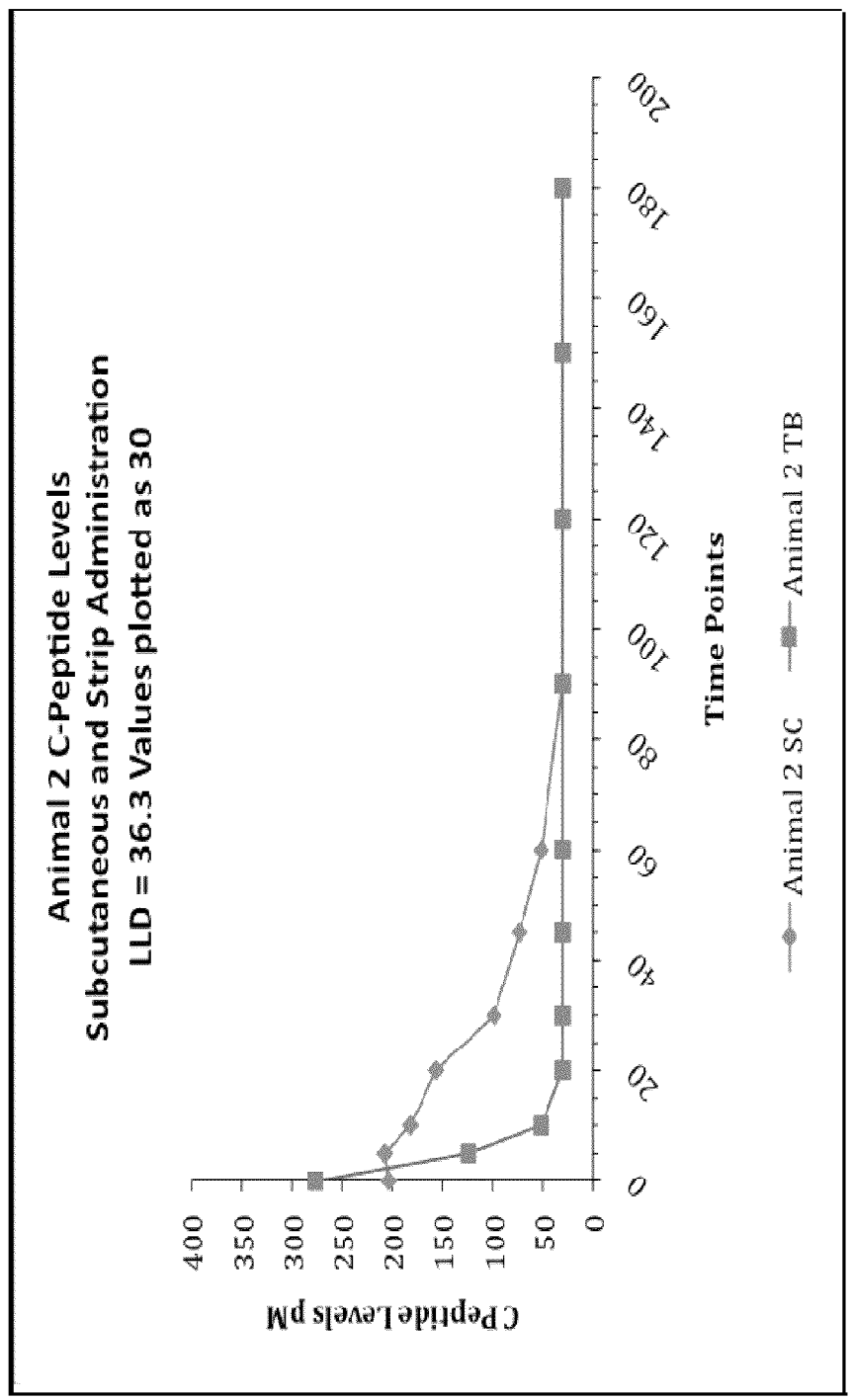

Results are shown in FIG. 23. The measurement of human C-Peptide is common in diabetic patients. A reduced level of C-Peptide is taken to be an indication of increased levels of exogenous insulin leading to a reduction of endogenous insulin in the patient. In the case of our experiment, the plots of all animals are consistent with the suppression of endogenous insulin production. For pig 2 (see FIG. 23 B)), which had the highest dynamic range the data suggests that this response is more rapid than in the sc administration. The other animals were not informative as a result of their lower dynamic range. It should be noted that for all the treated animals the levels drop below the minimum detectable level (36.3 pM) while the control animal maintains measurable levels.

Blood Glucose Levels

Figure 24A:
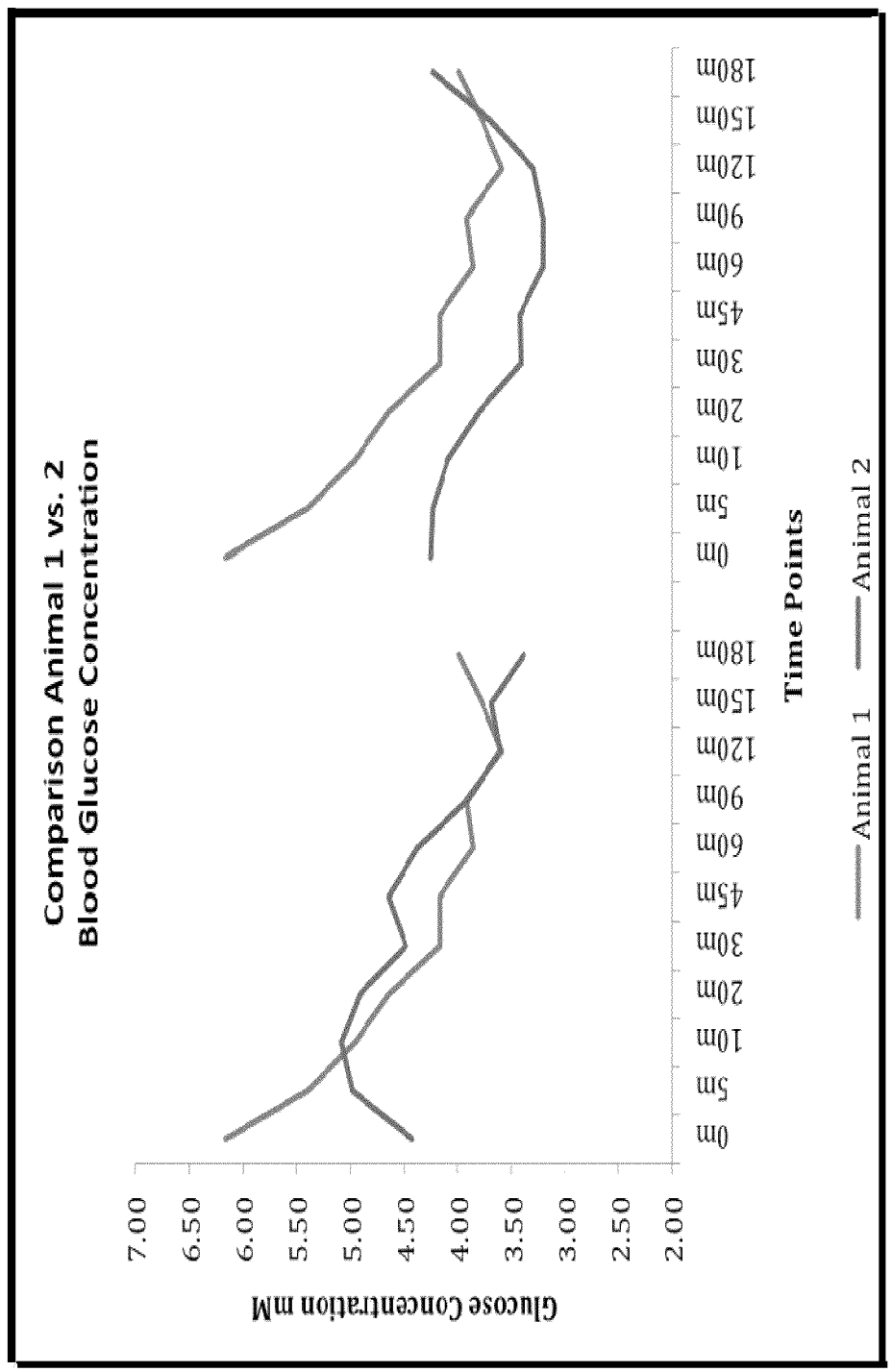
FIG. 24 shows blood glucose plots over time following subcutaneous (left) and transbuccal (right) administration for A) minipig 1 vs. 2. B) minipig 1 vs. 3 and C) minipig 1 vs. 4, where the plots were averaged over two experiments.
Figure 24B:
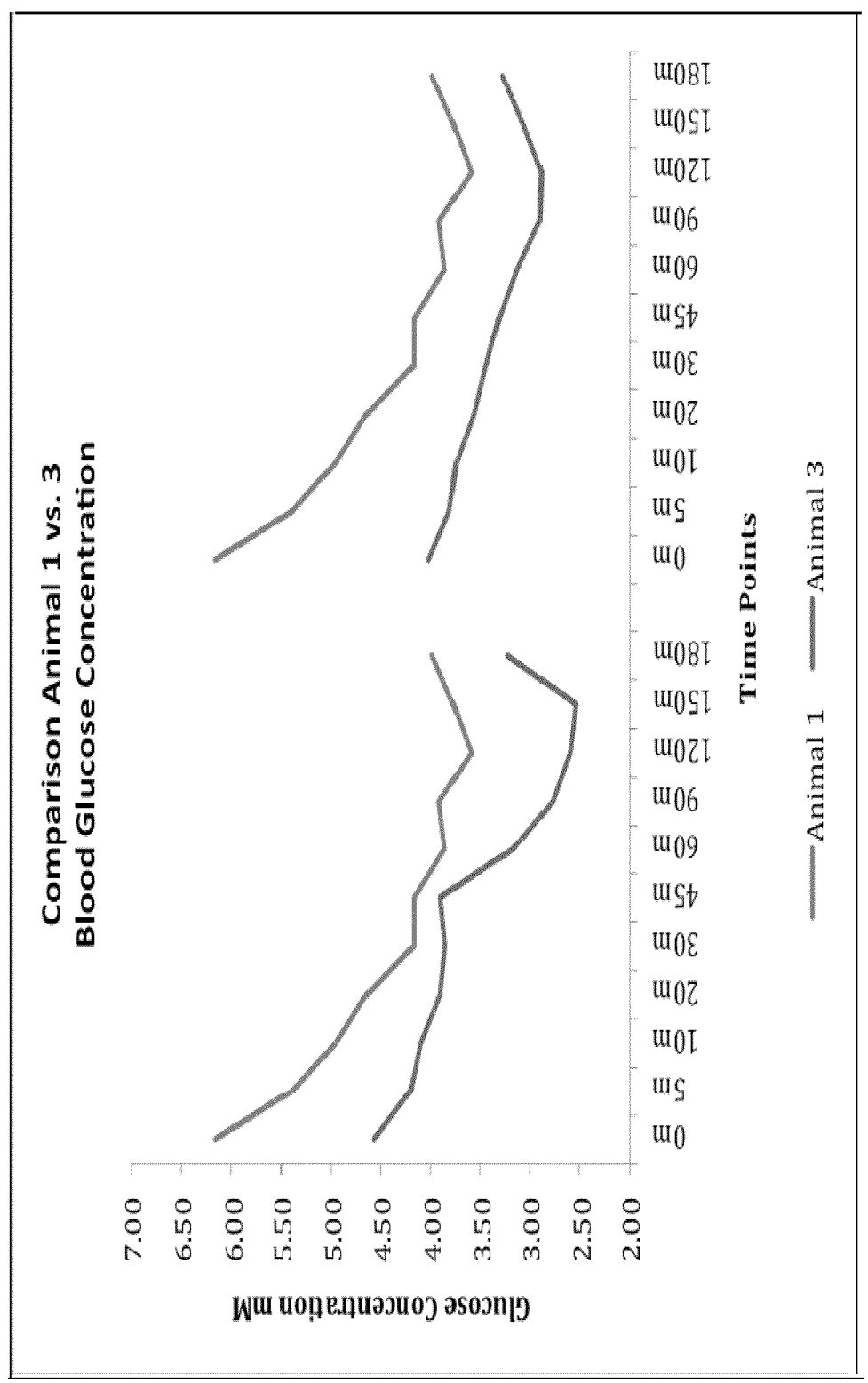
Figure 24C:
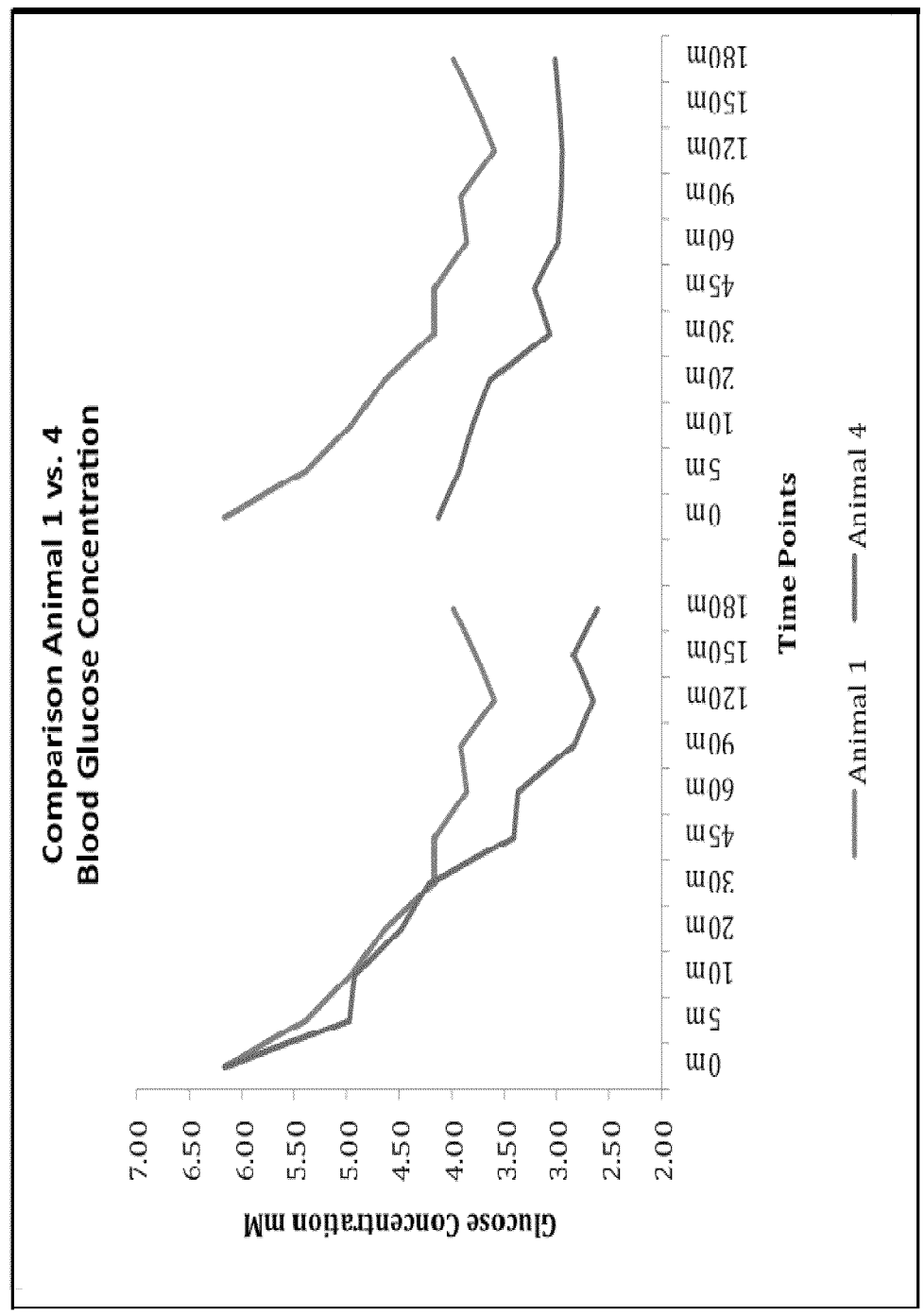

The data on blood glucose is plotted as absolute values and is shown in FIG. 24. Each graph shows the plots for the complete two runs, subcutaneous injection data on the left and transbuccal data on the right. The set of graphs of FIGS. 24 A)-C) have the control data averaged over the two experiments. This therefore represents a longitudinal study where each animal effectively acts as its own control, the left part of the graph showing how an animal responded to sc insulin and the right side how the same animal responded to the tb insulin seven days later. Comparison of left and right panels indicates difference in responses, both over time and in magnitude. As stated, the graphs are plotted against the control animal, which received sterile water for the first experiment and a blank strip in the second experiment.

A further consideration is that the literature suggests that in anaesthetised minipigs the insulin production is suppressed leading to significantly higher blood glucose levels. The implication here is that in non-anaesthetised animals we could expect to see an increased response not only to the sc insulin but also the transbuccally administered insulin via the strips.

Conclusions Regarding Blood Glucose Levels

1. Based on the longitudinal comparator to the positive control sc injection, lowering of blood glucose levels has been achieved in the tb animals that is consistent with the presence of insulin and to a degree as good as the sc administration.

2. That in the light of the response to the anaesthetic used as reported in the literature, where glucose levels have been seen to rise, the obtained results could be concluded to be even more significant than the measured levels indicate.

Insulin Levels

Figure 25A:
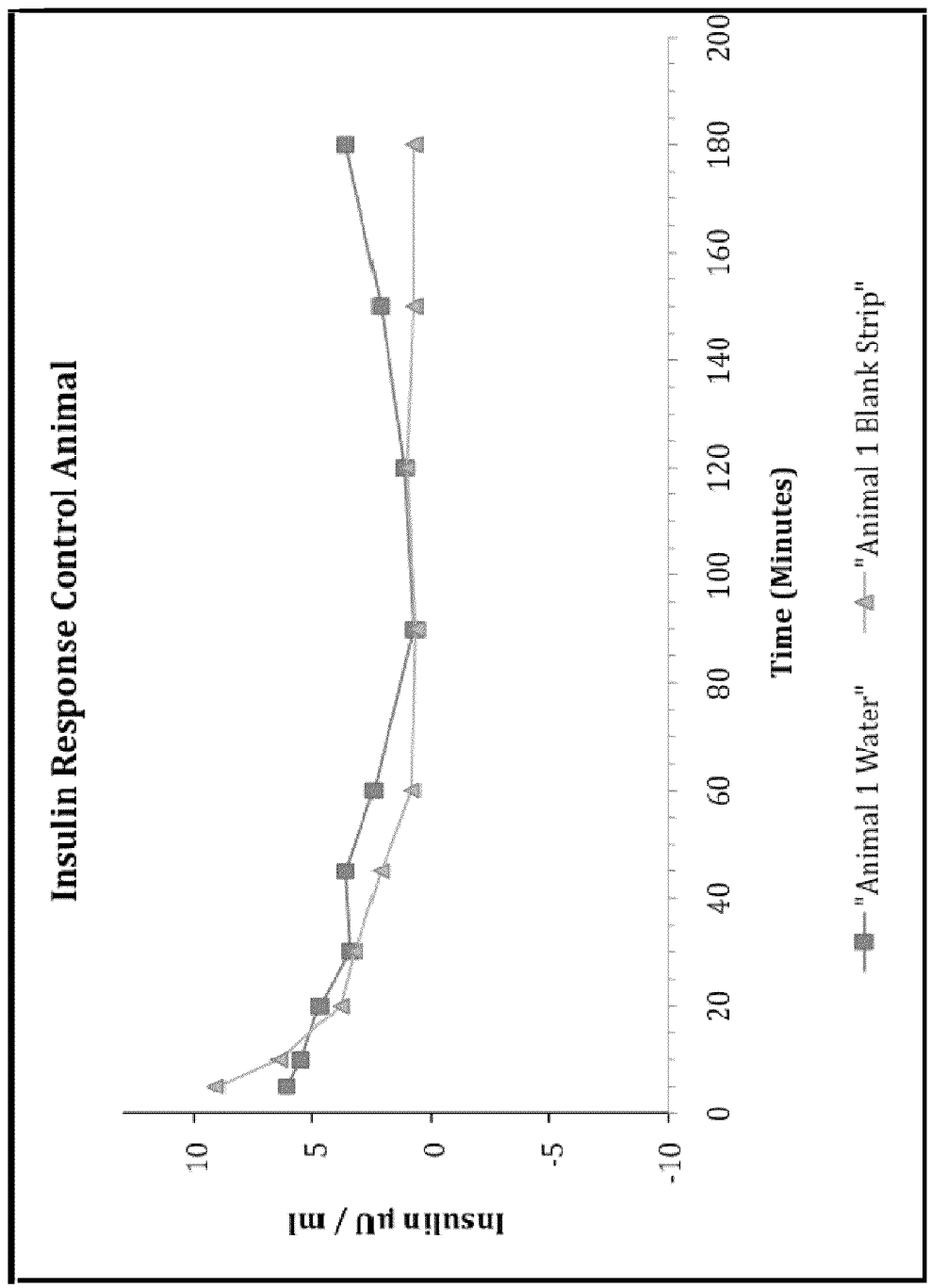
FIG. 25 shows plots of measured insulin A) shows insulin levels μU/ml for control minipig 1 during subcutaneous insulin experiment and transbuccal insulin experiment using water and blank strip controls; B) shows day 0 data insulin levels, μU/ml, present in minipigs 2, 3 and 4 after injection of 2.5 IU human insulin corrected for changes in background levels shown in A) (minipig 1 sc) plotted from 5 min point onward; C) shows day 7 data insulin levels μU/ml present in minipigs 2, 3 and 4 after transbuccal administration of 5 IU human insulin-strips corrected for changes in background levels of insulin shown in A) (minipig 1 tb)
Figure 25B:
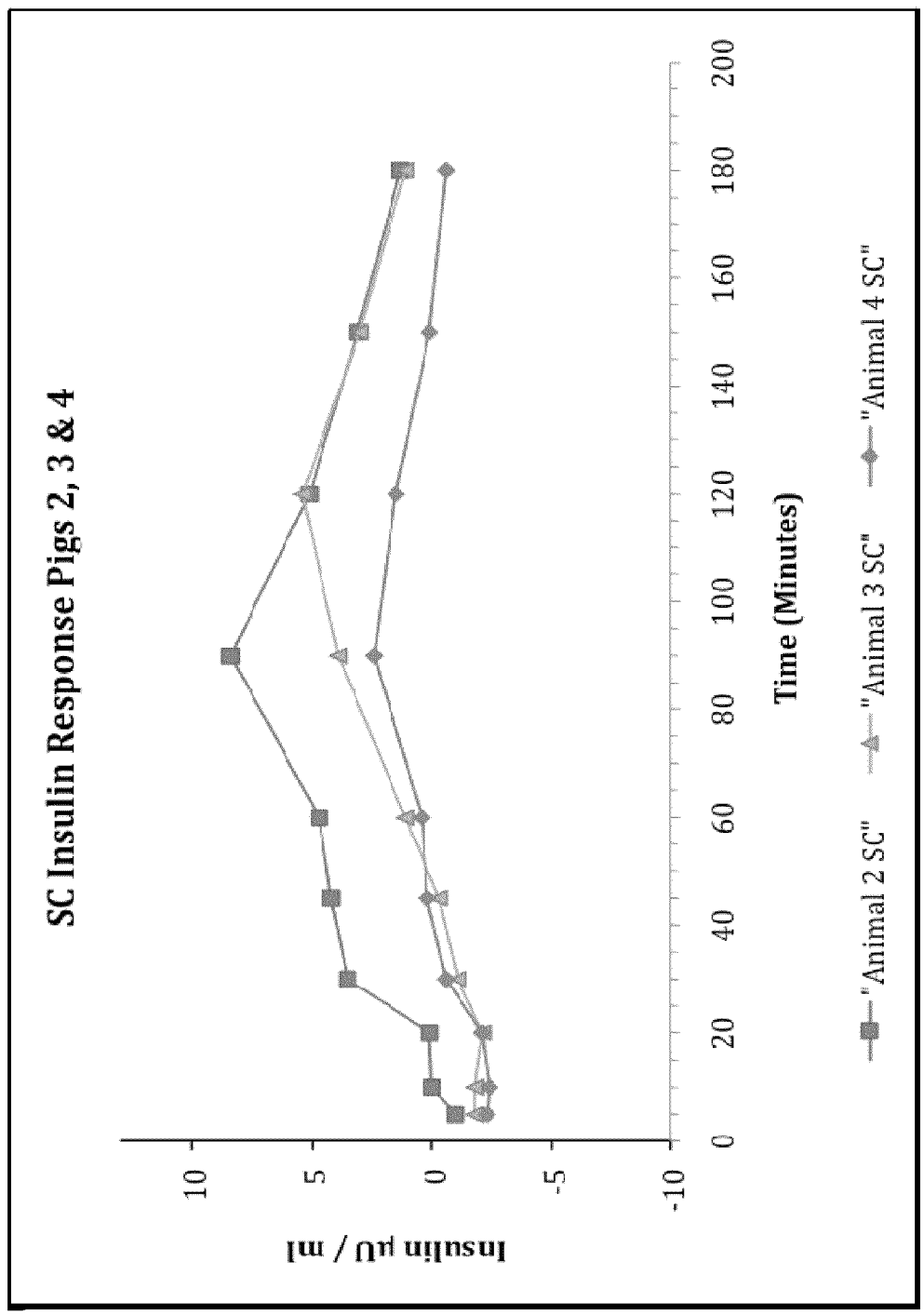
Figure 25C:
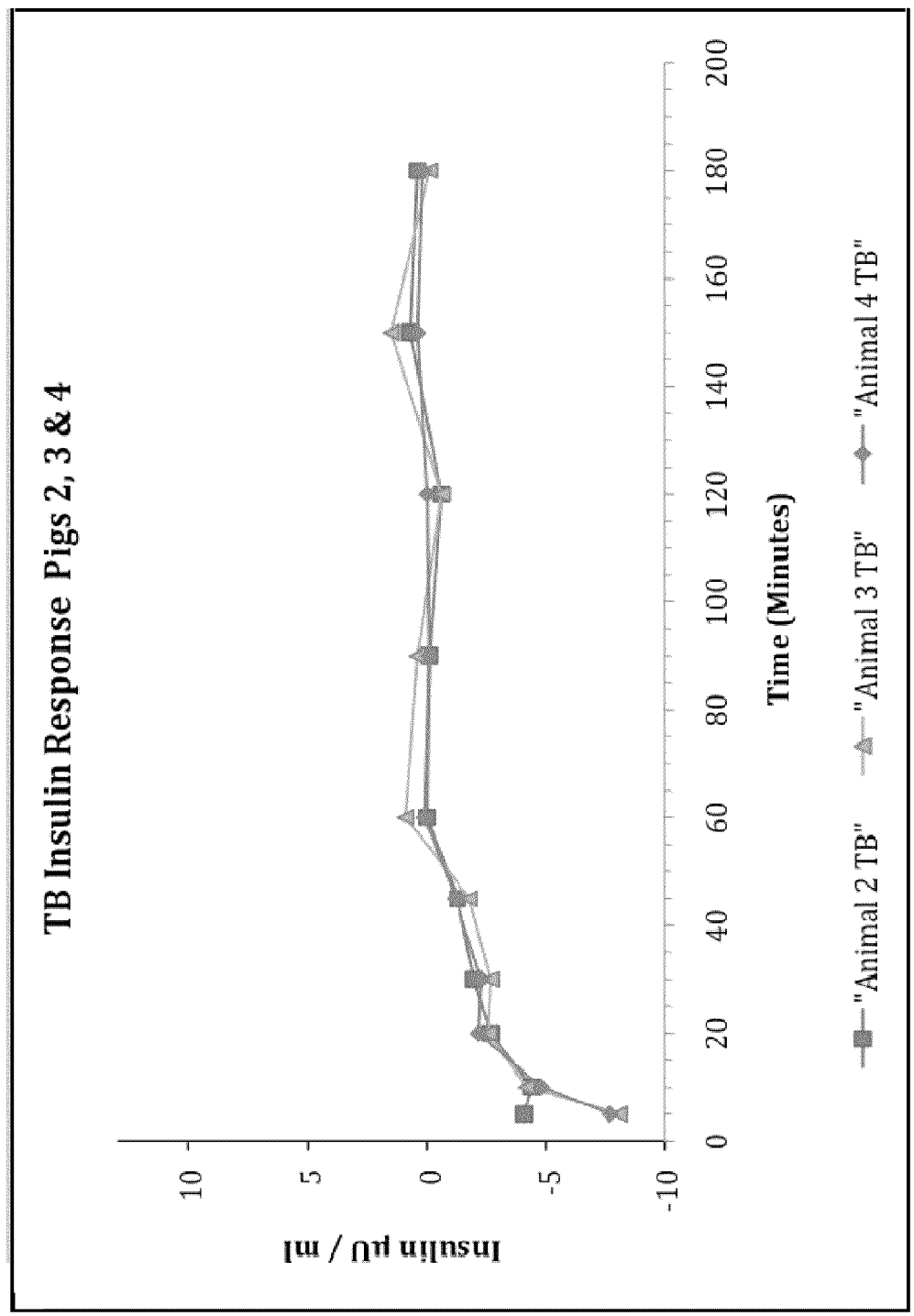

FIG. 25 shows the data obtained from the measurement of insulin in the samples.

FIG. 25 A) shows insulin levels μU/ml for control Minipig 1 during subcutaneous (sc) insulin experiment and transbuccal (tb) insulin experiment.

Figure 21:
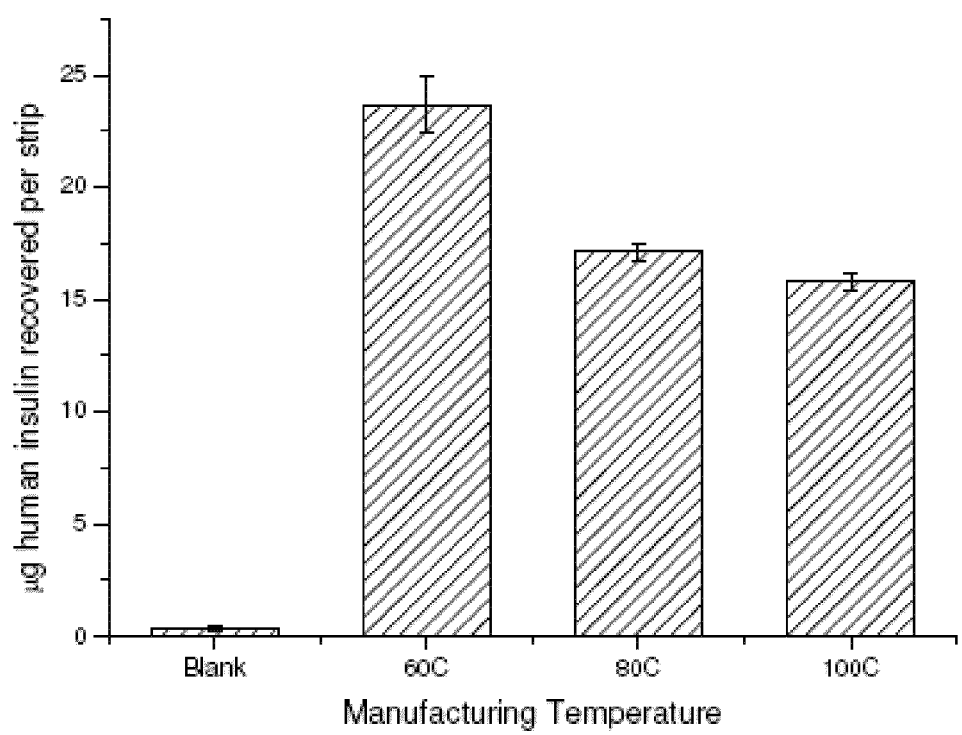
FIG. 21 shows plots of amount of human insulin in μg recovered from polymer strips at manufacturing temperatures 60° C., 80° C. and 100° C. compared with a blank (error bars are indicated)

FIG. 25 B) shows day 0 data insulin levels, μU/ml, present in Minipigs 2, 3 and 4 after injection of 2.5 IU human insulin. Data corrected for changes in background levels shown in FIG. 21 A) (Animal 1 sc) plotted from 5 min point onward.

FIG. 25 C) shows day 7 data insulin levels μU/ml present in Minipigs 2, 3 and 4 after transbuccal of 5 IU human insulin-strips. Data corrected for changes in background levels of insulin shown in FIG. 25 A) (Animal 1 tb).

Observations Regarding Insulin Levels:

1. Longitudinal analysis suggests that tb delivery was as good as sc insulin and perhaps had a more rapid onset in some of the minipigs.

2. The measurements of insulin available at this point (see above) appear to support the conclusion drawn from the blood glucose levels. Namely, that we have achieved absorption of human insulin from the strips across the buccal membrane.

3. C-Peptide measurements provide further support for conclusions 1. and 2.

4. Our dynamic range for response in this experiment is very small since the minipigs were starved and had low resting blood glucose levels. The data also show that even with the positive control sc insulin injections, the lowest values we can reasonably achieve is 2.5-3 mM blood glucose. These animals are tending towards hypoglycaemia and so the liver will produce glucose to prevent the levels going any lower.

5. The control pig also had a substantial drop in blood glucose, but on an absolute scale, the lowest levels are always above the insulin treated animals. The control pig also had higher fasting blood glucose but we understand that this is within the normal range of variability for this strain of mini-pig. All of the treated minipigs had similar starting points for the resting blood glucose.

The data obtained for blood glucose, insulin and C-Peptide levels show that we have achieved transbuccal absorption of insulin from the strips and that this has produced a biological response in the minipigs to a degree as effective as the control response from a 2 IU subcutaneous injection.

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

The invention claimed is:

1. A therapeutic or bioaffecting film delivery system comprising:
   (a) one or more film matrices comprising at least one polymer;
   (b) a plurality of nanoparticles incorporated in at least one of said film matrices, said nanoparticles comprising:
      (i) a core comprising a metal;
      (ii) a corona comprising a plurality of ligands covalently linked to the core, wherein at least one of said ligands comprises a carbohydrate moiety and at least one of said ligands is a non-carbohydrate ligand comprising an amine group; and
      (iii) at least one peptide is non-covalently bound to the corona.

2. The film delivery system according to claim 1, wherein the peptide is reversibly bound to the corona.

3. The film delivery system according to claim 1, wherein the peptide is bound to the corona such that at least a fraction of the bound peptide is released from the nanoparticle upon contacting the nanoparticle with a physiological solution.

4. The film delivery system according to claim 3, wherein said release comprises dissociation of bound peptide molecules from the nanoparticle rapidly within minutes followed by further sustained release over a period of at least 2 or more hours.

5. The film delivery system according to claim 3, wherein said release comprises dissociation of bound peptide molecules from the nanoparticle over a period of at least 4 or more hours.

6. The film delivery system according to claim 1, wherein the peptide is capable of stimulating a physiologic response in a mammalian subject.

7. The film delivery system according to claim 1, wherein the peptide is selected from the group consisting of: insulin, GLP-1, IGF1, IGF2, relaxin, INSL5, INSL6, INSL7, pancreatic polypeptide (PP), peptide tyrosine tyrosine (PTT), neuropeptide Y, oxytocin, vasopressin, GnRH, TRH, CRH, GHRH/somatostatin, FSH, LH, TSH, CGA, prolactin, ClIP, ACTH, MSH, enorphins, lipotropin, GH, calcitonin, PTH, inhibin, relaxin, hCG, HPL, glucagons, somatostatin, melatonin, thymosin, thmulin, gastrin, ghrelin, thymopoietin, CCK, GIP secretin, motin VIP, enteroglucagon, IGF-1,IGF-2, leptin, adiponectin, resistin Osteocalcin, renin, EPO, calicitrol, ANP, BNP, chemokines, cytokines, adipokines and biologically active analogs thereof.

8. The film delivery system according to claim 6, wherein the peptide is capable of stimulating a reduction in blood glucose levels in a mammalian subject.

9. The film delivery system according to claim 7, wherein the peptide comprises monomeric and/or dimeric human insulin.

10. The film delivery system according to claim 1, wherein the carbohydrate moiety comprises a monosaccharide and/or a disaccharide.

11. The film delivery system according to claim 10, wherein the carbohydrate moiety comprises a glycoside of galactose, glucose, glucosamine, N-acetylglucosamine, mannose, fucose and/or lactose.

12. The film delivery system according to claim 11, wherein the carbohydrate moiety comprises a galactopyranoside and/or a glucopyranoside.

13. The film delivery system according to claim 1, wherein the carbohydrate moiety is covalently linked to the core via a linker selected from the group consisting of: sulphur-containing linkers, amino-containing linkers, phosphate-containing linkers and oxygen-containing linkers.

14. The film delivery system according to claim 13, wherein the linker comprises an alkyl chain of at least two carbons.

15. The film delivery system according to claim 1, wherein said at least one ligand comprising a carbohydrate moiety is selected from the group consisting of: 2'-thioethyl-α-D-galactopyranoside, 2'-thioethyl-β-D-glucopyranoside, 2'-thioethyl-2-acetamido-2-deoxy-β-D-glucopyranoside, 5'-thiopentanyl-2-deoxy-2-imidazolacetamido-α,β-D-glucopyranoside and 2'-thioethyl-α-D-glucopyranoside, and wherein said at least one ligand comprising a carbohydrate moiety is covalently linked to the core via the thiol sulphur.

16. The film delivery system according to claim 1, wherein said at least one non-carbohydrate ligand comprises 1-amino-17-mercapto-3,6,9,12,15,-pentaoxa-heptadecanol covalently linked to the core via the thiol sulphur.

17. The film delivery system according to claim 1, wherein said at least one ligand comprising a carbohydrate moiety and said at least one non-carbohydrate ligand are different and are present on the nanoparticle in a ratio of 1:40 to 40:1.

18. The film delivery system according to claim 17, wherein in the ratio is 1:10 to 10:1.

19. The film delivery system according to claim 18, wherein the ratio is 1:2 to 2:1.

20. The film delivery system according to claim 1, wherein the corona comprises at least 5 ligands per core.

21. The film delivery system according to claim 20, wherein the corona comprises about 10 to about 1000 ligands per core.

22. The film delivery system according to claim 21, wherein the corona comprises 44-106 ligands per core.

23. The film delivery system according to claim 1, wherein at least 5 or more peptide molecules are bound per core.

24. The film delivery system according to claim 1, wherein the core comprises a metal selected from the group consisting of: Au, Ag, Cu, Pt, Pd, Fe, Co, Gd, Zn or any combination thereof.

25. The film delivery system according to claim 24, wherein the core comprises a passive metal selected from the group consisting of: Au, Ag, Pt, Pd and Cu, or any combination thereof.

26. The film delivery system according to claim 24, wherein the core comprises a combination of metals selected from the group consisting of: Au/Fe, Au/Ag, Au/Cu, Au/Ag/Cu, Au/Pt, Au/Pd, Au/Ag/Cu/Pd, Au/Gd, Au/Fe/Cu, Au/Fe/Gd, Au/Fe/Cu/Gd.

27. The film delivery system according to claim 1, wherein the core is magnetic.

28. The film delivery system according to claim 1, wherein the core further comprises an NMR active atom selected from the group consisting of: $Mn^{2+}$, $Gd^{3+}$, $Eu^{2+}$, $Cu^{2+}$, $V^{2+}$, $Co^{2+}$, $Ni^{2+}$, $Fe^{2+}$, $Fe^{3+}$ and lanthanides$^{3+}$.

29. The film delivery system according to claim 1, wherein the core further comprises a semiconductor.

30. The film delivery system according to claim 29, wherein the semiconductor is selected from the group consisting of: cadmium selenide, cadmium sulphide, cadmium tellurium and zinc sulphide.

31. The film delivery system according to claim 1, wherein the core comprises a metal oxide coated with a metal selected from the group consisting of: Au, Ag, Cu, Pt, Pd and Zn, or any combination thereof.

32. The film delivery system according to claim 31, wherein said metal oxide is of the formula $XFe_2O_4$, where X is a metal selected from the group consisting of: Fe, Mn and Co.

33. The film delivery system according to claim 1, wherein the nanoparticle cores have an average diameter in the range of about 0.5 nm to about 50 nm.

34. The film delivery system according to claim 33, wherein said average diameter is in the range of about 1 nm to about 10 nm.

35. The film delivery system according to claim 33, wherein said average diameter is in the range of about 1.5 nm to about 2 nm.

36. The film delivery system according to claim 1, wherein the nanoparticle core comprises a divalent component.

37. The film delivery system according to claim 36, wherein said divalent component is present in the corona of the nanoparticle.

38. The film delivery system according to claim 36, wherein said divalent component is selected from the group consisting of divalent metals, divalent metal compounds or other components having a divalent state.

39. The film delivery system according to claim 36, wherein said divalent component is selected from the group consisting of zinc, magnesium, copper, nickel, cobalt, cadmium, or calcium, their oxides and salts thereof.

40. The film delivery system according to claim 39, wherein said zinc is selected from: $Zn^{2+}$ and ZnO.

41. The film delivery system according to claim 40, wherein the zinc comprises $ZnCl_2$.

42. The film delivery system according to claim 36, wherein said divalent component is present in an amount sufficient to produce a stabilizing effect.

43. The film delivery system according to claim 42, wherein said divalent component is present in an amount of about 0.5 to about 2.0 equivalents of said metal in said core.

44. The film delivery system according to claim 42, wherein said divalent component is present in an amount of about 0.75 to about 1.5 equivalents of said metal in said core.

45. The film delivery system according to claim 1, wherein the one or more film matrices are formed by evaporating a solvent carrier from the matrices to form a visco-elastic film within about the first 10 minutes of applying heat or radiation energy whereby the nanoparticles are locked in or substantially prevented from migrating within the matrices to provide a film delivery system with a uniform distribution of the nanoparticles.

46. The film delivery system according to claim 45, divided into individual dosage units, each dosage unit having an appropriate amount of peptide for administration, wherein said uniform distribution of the nanoparticles is such that the amount of peptide in each dosage unit does not vary more than 10% from said appropriate amount.

47. The film delivery system according to claim 1, wherein the one or more film matrices comprise two film layers having different release properties.

48. The film delivery system according to claim 1, wherein the one or more film matrices comprise at least one water soluble or water swellable polymer.

49. The film delivery system according to claim 48, wherein the at least one water soluble or water swellable polymer is selected from the group consisting of polyethylene oxide, cellulose, a cellulose derivative, pullulan, polyvinyl pyrrolidone, polyvinyl alcohol, polyethylene glycol, carboxyvinyl copolymers, hydroxypropylmethyl cellulose, hydroxyethyl cellulose, hydroxypropyl cellulose, carboxymethyl cellulose, sodium alginate, xanthan gum, tragancanth gum, guar gum, acacia gum, arabic gum, polyacrylic acid, methylmethacrylate copolymer, carboxyvinyl copolymers, starch, gelatin, and combinations thereof, alone or in combination with polyethylene oxide.

50. The film delivery system of claim 49, wherein said polymer further comprises a polymer selected from the group consisting of sodium alginate, xanthan gum, tragancanth gum, guar gum, acacia gum, arabic gum, starch, gelatin, carageenan, locust bean gum, dextran, gellan gum, pullulan and combinations thereof.

51. The film delivery system of claim 49, wherein said polymer further comprises a polymer selected from the group consisting of ethylcellulose, hydroxypropyl ethyl cellulose, cellulose acetate phthalate, hydroxypropyl methyl cellulose phthalate, polyvinylacetatephthalates, phthalated gelatin, crosslinked gelatin, poly(lactic acid)/poly(glycolic acid)/polyethyleneglycol copolymers, polycaprolactone, methylmethacrylate copolymer, polyacrylic acid polymer, poly(glycolic acid) (PGA), poly(lactic acid) (PLA), poly(lactic acid)/poly(glycolic acid)/polyethyleneglycol copolymers, polydioxanoes, polyoxalates, poly (α-esters), polyanhydrides, polyacetates, polycaprolactones, poly(orthoesters), polyamino acides, polyaminocarbonates, polyurethanes, polycarbonates, polyamides, poly(alkyl cyanoacrylates), sodium alginate, xanthan gum, tragancanth gum, guar gum, acacia gum, arabic gum, starch, gelatin, carageenan, locust bean gum, dextran, gellan gum and combinations thereof.

52. The film delivery system of claim 49, wherein said solvent is selected from the group consisting of water, polar organic solvent, and combinations thereof.

53. The film delivery system of claim 48, wherein the at least one water soluble or water swellable polymer is selected from the group consisting of ethylcellulose, hydroxypropyl ethyl cellulose, cellulose acetate phthalate, hydroxypropyl methyl cellulose phthalate, polyvinylacetatephthalates, phthalated gelatin, crosslinked gelatin, poly(lactic acid)/poly(glycolic acid)/polyethyleneglycol copolymers, polycaprolactone and combinations thereof.

54. The film delivery system of claim 48, wherein the at least one water soluble or water swellable polymer is selected from the group consisting selected from the group consisting of methylmethacrylate copolymer, polyacrylic acid polymer, poly(glycolic acid) (PGA), poly(lactic acid) (PLA), poly(lactic acid)/poly(glycolic acid)/polyethyleneglycol copolymers, polydioxanoes, polyoxalates, poly (α-esters), polyanhydrides, polyacetates, polycaprolactones, poly(orthoesters), polyamino acides, polyaminocarbonates, polyurethanes, polycarbonates, polyamides, poly(alkyl cyanoacrylates), and mixtures and copolymers thereof.

55. The film delivery system according to claim 1, wherein the nanoparticles are uniformly distributed within the at least one or more film matrices.

56. The film delivery system according to claim 1, where in the total water content is about 10% or less by weight of the delivery system.

57. The film delivery system according to claim 1, wherein the nanoparticles are incorporated or deposited on the surface of the one or more film matrices.

58. The film delivery system according to claim 1, further comprising a permeation and/or penetration enhancing agent.

59. The film delivery system of claim 58, wherein the permeation or penetration enhancing agent is selected from the group consisting of medium chain mono and diacylglycerol fatty acid derivatives, synthetic and natural surfactants, medium chain fatty acids and salts and esters thereof, bile salts, chelating agents, detergents, phospholipids, lecithins, cetomacrogels, glycerol and polyalkylene glycols and their esters, salicylates, polysorbates, alkylsulfoxides, alkanols, fatty acids and their corresponding esters and alcohols, urea and cyclic ureas, pyrrolidone derivatives, alkyl and cyclic amides, anionic surfactants, cationic surfactants, non-ionic surfactants, ketones, alkyl oxides, cycloalkene oxides, oils, alkyl glycosides, zonula occuludens, alcohols, and combinations thereof.

60. The film delivery system according to claim 58, wherein the permeation enhancing agent is coupled to the nanoparticle core and/or the nanoparticle corona.

61. The film delivery system according to claim 1, divided into individual dosage units, each dosage unit having an appropriate amount of peptide for administration, wherein the amount of peptide in each dosage unit does not vary more than 10% from said appropriate amount.

62. An insulin-containing film delivery system comprising:
  (a) one or more film matrices comprising at least one polymer;
  (b) a plurality of nanoparticles incorporated in at least one of said film matrices, said nanoparticles comprising:
    (i) a core comprising a gold;
    (ii) a plurality of ligands covalently attached to the core and forming a corona around the core, wherein the ligands comprise 2"-thioethyl-α-D-galactopyranoside and 1-amino-17-mercapto-3,6,9,12,15,-pentaoxa-heptadecanol each bonded to the core via their respective sulphur atoms, and wherein the nanoparticles have an average of at least five insulin monomers non-covalently bound to the corona per nanoparticle core.

63. A therapeutic or bioaffecting film delivery system comprising:
  (a) one or more film matrices comprising at least one polymer;
  (b) a plurality of nanoparticles incorporated in at least one of said film matrices, said nanoparticles comprising:
    (i) a core comprising a metal;
    (ii) a corona comprising a plurality of ligands covalently linked to the core, wherein at least one of said ligands comprises a carbohydrate moiety and at least one of said ligands is a non-carbohydrate ligand; and
    (iii) at least one peptide is non-covalently bound to the corona, wherein said at least one ligand comprising a carbohydrate moiety and said at least one non-carbohydrate ligand are present on the nanoparticle in a ratio of 1:40 to 40:1.

64. The film delivery system according to claim 63, wherein the peptide is reversibly bound to the corona.

65. The film delivery system according to claim 63, wherein the peptide is bound to the corona such that at least a fraction of the bound peptide is released from the nanoparticle upon contacting the nanoparticle with a physiological solution.

66. The film delivery system according to claim 65, wherein said release comprises dissociation of bound peptide molecules from the nanoparticle rapidly within minutes followed by further sustained release over a period of at least 2 or more hours.

67. The film delivery system according to claim 65, wherein said release comprises dissociation of bound peptide molecules from the nanoparticle over a period of at least 4 or more hours.

68. The film delivery system according to claim 63, wherein the peptide is capable of stimulating a physiologic response in a mammalian subject.

69. The film delivery system according to claim 68, wherein the peptide is capable of stimulating a reduction in blood glucose levels in a mammalian subject.

70. The film delivery system according to claim 63, wherein the peptide is selected from the group consisting of: insulin, GLP-1, IGF1, IGF2, relaxin, INSL5, INSL6, INSL7, pancreatic polypeptide (PP), peptide tyrosine tyrosine (PTT), neuropeptide Y, oxytocin, vasopressin, GnRH, TRH, CRH, GHRH/somatostatin, FSH, LH, TSH, CGA, prolactin, CIIP, ACTH, MSH, enorphins, lipotropin, GH, calcitonin, PTH, inhibin, relaxin, hCG, HPL, glucagons, somatostatin, melatonin, thymosin, thmulin, gastrin, ghrelin, thymopoietin, CCK, GIP secretin, motin VIP, enteroglucagon, IGF-1,IGF-2, leptin, adiponectin, resistin Osteocalcin, renin, EPO, calicitrol, ANP, BNP, chemokines, cytokines, adipokines and biologically active analogs thereof.

71. The film delivery system according to claim 70, wherein the peptide comprises monomeric and/or dimeric human insulin.

72. The film delivery system according to claim 63, wherein the carbohydrate moiety comprises a monosaccharide and/or a disaccharide.

73. The film delivery system according to claim 72, wherein the carbohydrate moiety comprises a glycoside of galactose, glucose, glucosamine, N-acetylglucosamine, mannose, fucose and/or lactose.

74. The film delivery system according to claim 72, wherein the carbohydrate moiety comprises a galactopyranoside and/or a glucopyranoside.

75. The film delivery system according to claim 63, wherein the carbohydrate moiety is covalently linked to the core via a linker selected from the group consisting of: sulphur-containing linkers, amino-containing linkers, phosphate-containing linkers and oxygen-containing linkers.

76. The film delivery system according to claim 75, wherein the linker comprises an alkyl chain of at least two carbons.

77. The film delivery system according to claim 63, wherein said at least one ligand comprising a carbohydrate moiety is selected from the group consisting of: 2"-thioethyl-α-D-galactopyranoside, 2'-thioethyl-β-D-glucopyranoside, 2'-thioethyl-2-acetamido-2-deoxy-β-D-glucopyranoside, 5'-thiopentanyl-2-deoxy-2-imidazolacetamido-α,β-D-glucopyranoside and 2'-thioethyl-α-D-glucopyranoside, and wherein said at least one ligand comprising a carbohydrate moiety is covalently linked to the core via the thiol sulphur.

78. The film delivery system according to claim 63, wherein said at least one non-carbohydrate ligand comprises an amine group.

79. The film delivery system according to claim 78, wherein said at least one non-carbohydrate ligand comprises 1-amino-17-mercapto-3,6,9,12,15,-pentaoxa-heptadecanol covalently linked to the core via the thiol sulphur.

80. The film delivery system according to claim 63, wherein in the ratio is 1:10 to 10:1.

81. The film delivery system according to claim 63, wherein the ratio is 1:2 to 2:1.

82. The film delivery system according to claim 63, wherein the corona comprises at least 5 ligands per core.

83. The film delivery system according to claim 82, wherein the corona comprises about 10 to about 1000 ligands per core.

84. The film delivery system according to claim 82, wherein the corona comprises 44-106 ligands per core.

85. The film delivery system according to claim 63, wherein at least 5 or more peptide molecules are bound per core.

86. The film delivery system according to claim 63, wherein the core comprises a metal selected from the group consisting of: Au, Ag, Cu, Pt, Pd, Fe, Co, Gd, Zn or any combination thereof.

87. The film delivery system according to claim 86, wherein the core comprises a passive metal selected from the group consisting of: Au, Ag, Pt, Pd and Cu, or any combination thereof.

88. The film delivery system according to claim 86, wherein the core comprises a combination of metals selected from the group consisting of: Au/Fe, Au/Ag, Au/Cu, Au/Ag/Cu, Au/Pt, Au/Pd, Au/Ag/Cu/Pd, Au/Gd, Au/Fe/Cu, Au/Fe/Gd, Au/Fe/Cu/Gd.

89. The film delivery system according to claim 63, wherein the core is magnetic.

90. The film delivery system according to claim 63, wherein the core further comprises an NMR active atom selected from the group consisting of: $Mn^{2+}$, $Gd^{3+}$, $Eu^{2+}$, $Cu^{2+}$, $V^{2+}$, $Co^{2+}$, $Ni^{2+}$, $Fe^{2+}$, $Fe^{3+}$ and lanthanides$^{3+}$.

91. The film delivery system according to claim 63, wherein the core further comprises a semiconductor.

92. The film delivery system according to claim 91, wherein the semiconductor is selected from the group consisting of: cadmium selenide, cadmium sulphide, cadmium tellurium and zinc sulphide.

93. The film delivery system according to claim 63, wherein the core comprises a metal oxide coated with a metal selected from the group consisting of: Au, Ag, Cu, Pt, Pd and Zn, or any combination thereof.

94. The film delivery system according to claim 93, wherein said metal oxide is of the formula $XFe_2O_4$, where X is a metal selected from the group consisting of: Fe, Mn and Co.

95. The film delivery system according to claim 63, wherein the nanoparticle cores have an average diameter in the range of about 0.5 nm to about 50 nm.

96. The film delivery system according to claim 95, wherein said average diameter is in the range of about 1 nm to about 10 nm.

97. The film delivery system according to claim 95, wherein said average diameter is in the range of about 1.5 nm to about 2 nm.

98. The film delivery system according to claim 63, wherein the nanoparticle core comprises a divalent component.

99. The film delivery system according to claim 98, wherein said divalent component is present in the corona of the nanoparticle.

100. The film delivery system according to claim 98, wherein said divalent component is selected from the group consisting of divalent metals, divalent metal compounds or other components having a divalent state.

101. The film delivery system according to claim 98, wherein said divalent component is selected from the group consisting of zinc, magnesium, copper, nickel, cobalt, cadmium, or calcium, their oxides and salts thereof.

102. The film delivery system according to claim 101, wherein said zinc is selected from: $Zn^{2+}$ and ZnO.

103. The film delivery system according to claim 102, wherein the zinc comprises $ZnCl_2$.

104. The film delivery system according to claim 98, wherein said divalent component is present in an amount sufficient to produce a stabilizing effect.

105. The film delivery system according to claim 104, wherein said divalent component is present in an amount of about 0.5 to about 2.0 equivalents of said metal in said core.

106. The film delivery system according to claim 104, wherein said divalent component is present in an amount of about 0.75 to about 1.5 equivalents of said metal in said core.

107. The film delivery system according to claim 63, wherein the one or more film matrices are formed by evaporating a solvent carrier from the matrices to form a viscoelastic film within about the first 10 minutes of applying heat or radiation energy whereby the nanoparticles are locked in or substantially prevented from migrating within the matrices to provide a film delivery system with a uniform distribution of the nanoparticles.

108. The film delivery system according to claim 107, divided into individual dosage units, each dosage unit having an appropriate amount of peptide for administration, wherein said uniform distribution of the nanoparticles is such that the amount of peptide in each dosage unit does not vary more than 10% from said appropriate amount.

109. The film delivery system according to claim 63, wherein the one or more film matrices comprise two film layers having different release properties.

110. The film delivery system according to claim 63, wherein the one or more film matrices comprise at least one water soluble or water swellable polymer.

111. The film delivery system according to claim 110, wherein the at least one water soluble or water swellable polymer is selected from the group consisting of polyethylene oxide, cellulose, a cellulose derivative, pullulan, polyvinyl pyrrolidone, polyvinyl alcohol, polyethylene glycol, carboxyvinyl copolymers, hydroxypropylmethyl cellulose, hydroxyethyl cellulose, hydroxypropyl cellulose, carboxymethyl cellulose, sodium alginate, xanthan gum, tragancanth gum, guar gum, acacia gum, arabic gum, polyacrylic acid, methylmethacrylate copolymer, carboxyvinyl copolymers, starch, gelatin, and combinations thereof, alone or in combination with polyethylene oxide.

112. The film delivery system of claim 111, wherein said polymer further comprises a polymer selected from the group consisting of sodium alginate, xanthan gum, tragancanth gum, guar gum, acacia gum, arabic gum, starch, gelatin, carageenan, locust bean gum, dextran, gellan gum, pullulan and combinations thereof.

113. The film delivery system of claim 111, wherein said polymer further comprises a polymer selected from the group consisting of ethylcellulose, hydroxypropyl ethyl cellulose, cellulose acetate phthalate, hydroxypropyl methyl cellulose phthalate, polyvinylacetatephthalates, phthalated gelatin, crosslinked gelatin, poly(lactic acid)/poly(glycolic acid)/polyethyleneglycol copolymers, polycaprolactone, methylmethacrylate copolymer, polyacrylic acid polymer, poly(glycolic acid) (PGA), poly(lactic acid) (PLA), poly(lactic acid)/poly(glycolic acid)/polyethyleneglycol copolymers, polydioxanoes, polyoxalates, poly (α-esters), polyanhydrides, polyacetates, polycaprolactones, poly(orthoesters), polyamino acides, polyaminocarbonates, polyurethanes, polycarbonates, polyamides, poly(alkyl cyanoacrylates), sodium alginate, xanthan gum, tragancanth gum, guar gum, acacia gum, arabic gum, starch, gelatin, carageenan, locust bean gum, dextran, gellan gum and combinations thereof.

114. The film delivery system of claim 111, wherein said solvent is selected from the group consisting of water, polar organic solvent, and combinations thereof.

115. The film delivery system of claim 110, wherein the at least one water soluble or water swellable polymer is selected from the group consisting of ethylcellulose, hydroxypropyl ethyl cellulose, cellulose acetate phthalate, hydroxypropyl methyl cellulose phthalate, polyvinylacetatephthalates, phthalated gelatin, crosslinked gelatin, poly(lactic acid)/poly(glycolic acid)/polyethyleneglycol copolymers, polycaprolactone and combinations thereof.

116. The film delivery system of claim 110, wherein the at least one water soluble or water swellable polymer is selected from the group consisting selected from the group consisting of methylmethacrylate copolymer, polyacrylic acid polymer, poly(glycolic acid) (PGA), poly(lactic acid) (PLA), poly(lactic acid)/poly(glycolic acid)/polyethyleneglycol copolymers, polydioxanoes, polyoxalates, poly (α-esters), polyanhydrides, polyacetates, polycaprolactones, poly(orthoesters), polyamino acides, polyaminocarbonates, polyurethanes, polycarbonates, polyamides, poly(alkyl cyanoacrylates), and mixtures and copolymers thereof.

117. The film delivery system according to claim 63, wherein the nanoparticles are uniformly distributed within the at least one or more film matrices.

118. The film delivery system according to claim 63, where in the total water content is about 10% or less by weight of the delivery system.

119. The film delivery system according to claim 63, wherein the nanoparticles are incorporated or deposited on the surface of the one or more film matrices.

120. The film delivery system according to claim 63, further comprising a permeation and/or penetration enhancing agent.

121. The film delivery system of claim 120, wherein the permeation or penetration enhancing agent is selected from the group consisting of medium chain mono and diacylglycerol fatty acid derivatives, synthetic and natural surfactants, medium chain fatty acids and salts and esters thereof, bile salts, chelating agents, detergents, phospholipids, lecithins, cetomacrogels, glycerol and polyalkylene glycols and their esters, salicylates, polysorbates, alkylsulfoxides, alkanols, fatty acids and their corresponding esters and alcohols, urea and cyclic ureas, pyrrolidone derivatives, alkyl and cyclic amides, anionic surfactants, cationic surfactants, non-ionic surfactants, ketones, alkyl oxides, cycloalkene oxides, oils, alkyl glycosides, zonula occuludens, alcohols, and combinations thereof.

122. The film delivery system according to claim 120, wherein the permeation enhancing agent is coupled to the nanoparticle core and/or the nanoparticle corona.

123. The film delivery system according to claim 63, divided into individual dosage units, each dosage unit having an appropriate amount of peptide for administration, wherein the amount of peptide in each dosage unit does not vary more than 10% from said appropriate amount.

\* \* \* \* \*

UNITED STATES PATENT AND TRADEMARK OFFICE
CERTIFICATE OF CORRECTION

| | | |
|---|---|---|
| PATENT NO. | : 8,974,826 B2 | Page 1 of 1 |
| APPLICATION NO. | : 13/157836 | |
| DATED | : March 10, 2015 | |
| INVENTOR(S) | : Alexander M. Schobel et al. | |

It is certified that error appears in the above-identified patent and that said Letters Patent is hereby corrected as shown below:

In the specification

At column 23, line 6, replace "non-limitin useful combinations" with -- non-limiting useful combinations --.

At column 25, line 15, replace "the drying step also be a contributing" with -- the drying step can also be a contributing --.

At column 35, line 39, replace "and the precipitated was dissolved" with -- and the precipitate was dissolved --.

At column 41, line 17, replace "film using the a K-Control coater" with -- film using the K-Control coater --.

Signed and Sealed this
Thirteenth Day of October, 2015

Michelle K. Lee
*Director of the United States Patent and Trademark Office*